United States Patent [19]
Reznikoff et al.

[11] Patent Number: 5,948,622
[45] Date of Patent: Sep. 7, 1999

[54] SYSTEM FOR IN VITRO TRANSPOSITION

[75] Inventors: William S. Reznikoff, Maple Bluff; Igor Yu Goryshin, Madison; Dona L. York, Wisconsin Dells; Hong Zhou, Madison, all of Wis.

[73] Assignee: Wisconsin Alumni Research Foundation, Madison, Wis.

[21] Appl. No.: 08/944,916

[22] Filed: Oct. 6, 1997

Related U.S. Application Data

[63] Continuation-in-part of application No. 08/850,880, May 2, 1997, which is a continuation-in-part of application No. 08/814,877, Sep. 9, 1996.

[51] Int. Cl.$^6$ .............................. C12Q 1/68; C12N 15/74; C12N 15/63; C07H 21/04
[52] U.S. Cl. ........................ 435/6; 435/473; 435/320.1; 536/23.1; 536/24.1
[58] Field of Search ..................... 435/6, 172.3, 320.1, 435/473; 536/23.1, 24.1

[56] References Cited

PUBLICATIONS

Ahmed, Asad, "Use of Transposon–Promoted Deletions in DNA Sequence Analysis", *Letter to Editor in J.Mol. Biol.,* 178:941–948 (1984).

Benjamin, Howard W., "Excisionof Tn10 from the donor site during transposition occurs by flush double–strand cleavages at the transposon termini," *Proc. Natl. Acad. Sci. USA,* 89:4648–4652 (May 1992).

Craigie, Robert, et al., "A defined system for the DNA strand–transfer reaction at the initiation of bacteriophage Mu transposition: Protein and DNA substrate requirements," *Proc. Natl. Acad. Sci. USA,* 82:7570–7574 (Nov. 1985).

de la Cruz, Norberto, B., et al., "Characterization of the TN5 Transposase and Inhibitor Proteins: a Model for the Inhibition of Transposition," *Journal of Bacterioilogy,* 175(21):6932–6938 (Nov. 1993).

Devine et al., "Efficient Integration of Artificial Transposons into Plasmid Target in vitro: a Useful Tool for DNA Mapping, Sequencing and Genetic Analysis", *Nucleic Acid Research,* 22 No. 18:3765–3772 (1994).

Devine et al., "A Transposon–base Strategy for Sequencing Repetitive DNA in Eukaryotic Genomes", *In Press, Genome Research* (1998).

Hattori et al., "A Novel Method for Making Nested Deletions and Its Application for Sequencing of a 300 kb Region of Human APP Locus", *Nucleic Acids Research,* 25 No. 9: 1802–1808 (1997).

Henikoff, Steven, "Unidirectional Digestion with Exonuclease III Creates Targeted Breakpoints for DNA Sequencing", *Gene,* 28:351–359 (1984).

Jilk, Ross A., et al., "The Organization of the Outside End of Transposon Tn5," *Journal of Bacteriology,* 178(6):1671–1679 (Mar. 1996).

Jilk et al., "Implications of Tn5–Associated Adjacent Deletions", *J. of Bacteriology,* 175: 1264–1271 (1993).

Krishnan et al., "Construction of a Genomic DNA 'Feature Map' by Sequencing from Nested Deletions: Application to the HLA Class I Region", *Nucleic Acids Research,* 23 No. 1: 117–122 (1995).

Lavoie, B.D., et al., "Transposition of Phage Mu DNA," Dept. of Biochemistry, U. of Western Ontario.

Lu et al., "Characterization of the Interaction Between the Tn7 Transposase (TnsA+B) and the Transposase Regulator TnsC", *Keystone Symposia: Transposition and Site–Specific Recombination,* Santa Fe (1997).

Mizuuchi, Kiyoshi, "In Vitro Transposition of Bacteriophage Mu: A Biochemical Approach to a Novel Replication Reaction," *Cell,* 35:785–794 (1983).

Morisata, Donald, et al., "TN10 Transposition and Circle Formation In Vitro," *Cell,* 51:101–111 (1987).

Morita et al., "Nested Deletions from a Fixed Site as an Aid to Nucleotide Sequencing: An in vitro System Using Tn3 Transposase", *DNA Research,* 3:431–433 (1996).

Pues et al., "Construction of a Deletion Library Using a Mixture of 5'–Truncated Primers for Inverse PCR (IPCR)", *Nucleic Acids Research,* 25(6): 1303–1304 (1997).

Sakai, Janice, et al., "Identification and characterization of a pre–cleavage synaptic complex that is an early intermediate in TN10 transposition," *The EMBO Journal,* 14(17):4374–4383 (1995).

Strathmann et al., "Transposon–facilitated DNA Sequencing", *Proc. Natl. Acad. Sci.,* 88: 1247–1250 (1991).

Tomacsanyi et al., "Intramolecular Transposition by a Synthetic IS50 (Tn5) Derivative", *J. Bacteriology,* 172(11):6348–6354 (1990).

Wang et al., "Inversions and Deletions Generated by a Mini–γδ (Tn1000) Transposon", *J. of Bacteriology,* 176(5): 6348–6354 (1990).

Wang et al., "pDUAL: A Transposon–Based Cosmid Cloning Vector for Generating Nested Deletions and DNA Sequencing Templated in vivo", *Proc. Natl. Acad. Sci.,* 90: 7874–7878 (1993).

Weinreich, Michael D., "A Functional Analysis of the TN5 Transposase: Identification of Domains Required for DNA Binding and Multimerization," *J. Mol. Biol.,* 241:166–177 (1994).

Yohda et al., "Solid–Phase Nested Deletion: A New Subcloning–less Method for Generating Nested Deletions", *DNA Research,* 2: 175–181 (1995).

(List continued on next page.)

*Primary Examiner*—Nancy Degen
*Assistant Examiner*—William Sandals
*Attorney, Agent, or Firm*—Quarles & Brady LLP

[57] ABSTRACT

A system for in vitro transposition includes a donor DNA that includes a transposable element flanked by a pair of bacterial transposon Tn5 outside end repeat sequences, a target DNA into which the transposable element can transpose, and a modified Tn5 transposase having higher binding avidity to the outside end repeat sequences and being less likely to assume an inactive multimer form than wild type Tn5 transposase.

20 Claims, 12 Drawing Sheets

OTHER PUBLICATIONS

Zhu and Marshall, "Rapid Construction of Nested Deletions of Recombinant Plasmid DNA for Dideoxy Sequencing", *BioTechniques*, 18(2): 222–224 (1995).

Delong et al., "Trans–acting Transposase Mutant from Tn5" *Proc. Natl. Acad. Sci. USA* 88(14):6072–6076 (1991).

Johnson et al., "DNA Sequences at the Ends of Transposon Tn5 Required for Transposition", *Nature* 304(21):280–282 (1983).

Wiegand et al., "Characterization of Two Hypertransposing Tn5 Mutants", *J. Bacteriol.* 174(4):1229–1239 (1992).

Wiegand et al., "Transposase Mutants That Increase the Transposition Frequency of Tn5", PhD Thesis (Abstract) University of Wisconsin–Madison (1993).

Zhou et al., "Three Types of Novel Mutations in the NH–2–Terminus of Tn5 Transposase: Structure–function of Transposase", Keystone Symposium on Transposition and Site–Specific Recombination: Mechanism and Biology (Abstract) Jan. 1994. J. of Cell Biochem. Suppl. O(18B) (1994).

a a

5,948,622

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1534 base pairs (B) TYPE: nucleic acid
        (C) STRANDEDNESS: double
        (D) TOPOLOGY: linear (ii) MOLECULE TYPE: other nucleic acid
        (A) DESCRIPTION: /desc = "Gene encoding modified Tn5
            transposase enzyme"

(ix) FEATURE:
        (A) NAME/KEY: CDS
        (B) LOCATION: 93..1523

(xi) SEQUENCE DESCRIPTION: SEQ ID NO:1:

```
CTGACTCTTA TACACAAGTA GCGTCCTGAA CGGAACCTTT CCCGTTTTCC AGGATCTGAT            60

CTTCCATGTG ACCTCCTAAC ATGGTAACGT TC ATG ATA ACT TCT GCT CTT CAT           113
                                   Met Ile Thr Ser Ala Leu His
                                     1               5

CGT GCG GCC GAC TGG GCT AAA TCT GTG TTC TCT TCG GCG GCG CTG GGT           161
Arg Ala Ala Asp Trp Ala Lys Ser Val Phe Ser Ser Ala Ala Leu Gly
         10                  15                  20

GAT CCT CGC CGT ACT GCC CGC TTG GTT AAC GTC GCC GCC CAA TTG GCA           209
Asp Pro Arg Arg Thr Ala Arg Leu Val Asn Val Ala Ala Gln Leu Ala
 25                  30                  35

AAA TAT TCT GGT AAA TCA ATA ACC ATC TCA TCA GAG GGT AGT AAA GCC           257
Lys Tyr Ser Gly Lys Ser Ile Thr Ile Ser Ser Glu Gly Ser Lys Ala
 40                  45                  50                  55

GCC CAG GAA GGC GCT TAC CGA TTT ATC CGC AAT CCC AAC GTT TCT GCC           305
Ala Gln Glu Gly Ala Tyr Arg Phe Ile Arg Asn Pro Asn Val Ser Ala
                 60                  65                  70

GAG GCG ATC AGA AAG GCT GGC GCC ATG CAA ACA GTC AAG TTG GCT CAG           353
Glu Ala Ile Arg Lys Ala Gly Ala Met Gln Thr Val Lys Leu Ala Gln
             75                  80                  85

GAG TTT CCC GAA CTG CTG GCC ATT GAG GAC ACC ACC TCT TTG AGT TAT           401
Glu Phe Pro Glu Leu Leu Ala Ile Glu Asp Thr Thr Ser Leu Ser Tyr
         90                  95                 100

CGC CAC CAG GTC GCC GAA GAG CTT GGC AAG CTG GGC TCT ATT CAG GAT           449
Arg His Gln Val Ala Glu Glu Leu Gly Lys Leu Gly Ser Ile Gln Asp
105                 110                 115

AAA TCC CGC GGA TGG TGG GTT CAC TCC GTT CTC TTG CTC GAG GCC ACC           497
Lys Ser Arg Gly Trp Trp Val His Ser Val Leu Leu Leu Glu Ala Thr
120                 125                 130                 135

ACA TTC CGC ACC GTA GGA TTA CTG CAT CAG GAG TGG TGG ATG CGC CCG           545
Thr Phe Arg Thr Val Gly Leu Leu His Gln Glu Trp Trp Met Arg Pro
                140                 145                 150

GAT GAC CCT GCC GAT GCG GAT GAA AAG GAG AGT GGC AAA TGG CTG GCA           593
Asp Asp Pro Ala Asp Ala Asp Glu Lys Glu Ser Gly Lys Trp Leu Ala
            155                 160                 165

GCG GCC GCA ACT AGC CGG TTA CGC ATG GGC AGC ATG ATG AGC AAC GTG           641
Ala Ala Ala Thr Ser Arg Leu Arg Met Gly Ser Met Met Ser Asn Val
        170                 175                 180

ATT GCG GTC TGT GAC CGC GAA GCC GAT ATT CAT GCT TAT CTG CAG GAC           689
Ile Ala Val Cys Asp Arg Glu Ala Asp Ile His Ala Tyr Leu Gln Asp
185                 190                 195

AGG CTG GCG CAT AAC GAG CGC TTC GTG GTG CGC TCC AAG CAC CCA CGC           737
Arg Leu Ala His Asn Glu Arg Phe Val Val Arg Ser Lys His Pro Arg
200                 205                 210                 215

AAG GAC GTA GAG TCT GGG TTG TAT CTG ATC GAC CAT CTG AAG AAC CAA           785
Lys Asp Val Glu Ser Gly Leu Tyr Leu Ile Asp His Leu Lys Asn Gln
                220                 225                 230

CCG GAG TTG GGT GGC TAT CAG ATC AGC ATT CCG CAA AAG GGC GTG GTG           833
Pro Glu Leu Gly Gly Tyr Gln Ile Ser Ile Pro Gln Lys Gly Val Val
            235                 240                 245
```

| | | |
|---|---|---|
| GAT AAA CGC GGT AAA CGT AAA AAT CGA CCA GCC CGC AAG GCG AGC TTG | | 881 |
| Asp Lys Arg Gly Lys Arg Lys Asn Arg Pro Ala Arg Lys Ala Ser Leu | | |
| 250 255 260 | | |
| | | |
| AGC CTG CGC AGT GGG CGC ATC ACG CTA AAA CAG GGG AAT ATC ACG CTC | | 929 |
| Ser Leu Arg Ser Gly Arg Ile Thr Leu Lys Gln Gly Asn Ile Thr Leu | | |
| 265 270 275 | | |
| | | |
| AAC GCG GTG CTG GCC GAG GAG ATT AAC CCG CCC AAG GGT GAG ACC CCG | | 977 |
| Asn Ala Val Leu Ala Glu Glu Ile Asn Pro Pro Lys Gly Glu Thr Pro | | |
| 280 285 290 295 | | |
| | | |
| TTG AAA TGG TTG TTG CTG ACC GGC GAA CCG GTC GAG TCG CTA GCC CAA | | 1025 |
| Leu Lys Trp Leu Leu Leu Thr Gly Glu Pro Val Glu Ser Leu Ala Gln | | |
| 300 305 310 | | |
| | | |
| GCC TTG CGC GTC ATC GAC ATT TAT ACC CAT CGC TGG CGG ATC GAG GAG | | 1073 |
| Ala Leu Arg Val Ile Asp Ile Tyr Thr His Arg Trp Arg Ile Glu Glu | | |
| 315 320 325 | | |
| | | |
| TTC CAT AAG GCA TGG AAA ACC GGA GCA GGA GCC GAG AGG CAA CGC ATG | | 1121 |
| Phe His Lys Ala Trp Lys Thr Gly Ala Gly Ala Glu Arg Gln Arg Met | | |
| 330 335 340 | | |
| | | |
| GAG GAG CCG GAT AAT CTG GAG CGG ATG GTC TCG ATC CTC TCG TTT GTT | | 1169 |
| Glu Glu Pro Asp Asn Leu Glu Arg Met Val Ser Ile Leu Ser Phe Val | | |
| 345 350 355 | | |
| | | |
| GCG GTC AGG CTG TTA CAG CTC AGA GAA AGC TTC ACG CCG CCG CAA GCA | | 1217 |
| Ala Val Arg Leu Leu Gln Leu Arg Glu Ser Phe Thr Pro Pro Gln Ala | | |
| 360 365 370 375 | | |
| | | |
| CTC AGG GCG CAA GGG CTG CTA AAG GAA GCG GAA CAC GTA GAA AGC CAG | | 1265 |
| Leu Arg Ala Gln Gly Leu Leu Lys Glu Ala Glu His Val Glu Ser Gln | | |
| 380 385 390 | | |
| | | |
| TCC GCA GAA ACG GTG CTG ACC CCG GAT GAA TGT CAG CTA CTG GGC TAT | | 1313 |
| Ser Ala Glu Thr Val Leu Thr Pro Asp Glu Cys Gln Leu Leu Gly Tyr | | |
| 395 400 405 | | |
| | | |
| CTG GAC AAG GGA AAA CGC AAG CGC AAA GAG AAA GCA GGT AGC TTG CAG | | 1361 |
| Leu Asp Lys Gly Lys Arg Lys Arg Lys Glu Lys Ala Gly Ser Leu Gln | | |
| 410 415 420 | | |
| | | |
| TGG GCT TAC ATG GCG ATA GCT AGA CTG GGC GGT TTT ATG GAC AGC AAG | | 1409 |
| Trp Ala Tyr Met Ala Ile Ala Arg Leu Gly Gly Phe Met Asp Ser Lys | | |
| 425 430 435 | | |
| | | |
| CGA ACC GGA ATT GCC AGC TGG GGC GCC CTC TGG GAA GGT TGG GAA GCC | | 1457 |
| Arg Thr Gly Ile Ala Ser Trp Gly Ala Leu Trp Glu Gly Trp Glu Ala | | |
| 440 445 450 455 | | |
| | | |
| CTG CAA AGT AAA CTG GAT GGC TTT CTT GCC GCC AAG GAT CTG ATG GCG | | 1505 |
| Leu Gln Ser Lys Leu Asp Gly Phe Leu Ala Ala Lys Asp Leu Met Ala | | |
| 460 465 470 | | |
| | | |
| CAG GGG ATC AAG ATC TGA TCAAGAGACA G | | 1534 |
| Gln Gly Ile Lys Ile * | | |
| 475 | | |

(2) INFORMATION FOR SEQ ID NO:2:

(i) SEQUENCE CHARACTERISTICS:
        (A) LENGTH: 476 amino acids
        (B) TYPE: amino acid
        (D) TOPOLOGY: linear (ii) MOLECULE TYPE: protein (xi) SEQUENCE DESCRIPTION: SEQ ID NO:2:

Met Ile Thr Ser Ala Leu His Arg Ala Ala Asp Trp Ala Lys Ser Val
1               5                   10                  15

Phe Ser Ser Ala Ala Leu Gly Asp Pro Arg Arg Thr Ala Arg Leu Val
            20                  25                  30

Asn Val Ala Ala Gln Leu Ala Lys Tyr Ser Gly Lys Ser Ile Thr Ile
        35                  40                  45

-continued

```
Ser Ser Glu Gly Ser Lys Ala Ala Gln Glu Gly Ala Tyr Arg Phe Ile
    50              55                  60
Arg Asn Pro Asn Val Ser Ala Glu Ala Ile Arg Lys Ala Gly Ala Met
65                  70                  75                  80
Gln Thr Val Lys Leu Ala Gln Glu Phe Pro Glu Leu Leu Ala Ile Glu
                85                  90                  95
Asp Thr Thr Ser Leu Ser Tyr Arg His Gln Val Ala Glu Glu Leu Gly
            100                 105                 110
Lys Leu Gly Ser Ile Gln Asp Lys Ser Arg Gly Trp Trp Val His Ser
            115                 120                 125
Val Leu Leu Leu Glu Ala Thr Thr Phe Arg Thr Val Gly Leu Leu His
    130                 135                 140
Gln Glu Trp Trp Met Arg Pro Asp Asp Pro Ala Asp Ala Asp Glu Lys
145                 150                 155                 160
Glu Ser Gly Lys Trp Leu Ala Ala Ala Thr Ser Arg Leu Arg Met
                165                 170                 175
Gly Ser Met Met Ser Asn Val Ile Ala Val Cys Asp Arg Glu Ala Asp
            180                 185                 190
Ile His Ala Tyr Leu Gln Asp Arg Leu Ala His Asn Glu Arg Phe Val
    195                 200                 205
Val Arg Ser Lys His Pro Arg Lys Asp Val Glu Ser Gly Leu Tyr Leu
    210                 215                 220
Ile Asp His Leu Lys Asn Gln Pro Glu Leu Gly Gly Tyr Gln Ile Ser
225                 230                 235                 240
Ile Pro Gln Lys Gly Val Val Asp Lys Arg Gly Lys Arg Lys Asn Arg
                245                 250                 255
Pro Ala Arg Lys Ala Ser Leu Ser Leu Arg Ser Gly Arg Ile Thr Leu
            260                 265                 270
Lys Gln Gly Asn Ile Thr Leu Asn Ala Val Leu Ala Glu Glu Ile Asn
            275                 280                 285
Pro Pro Lys Gly Glu Thr Pro Leu Lys Trp Leu Leu Leu Thr Gly Glu
            290                 295                 300
Pro Val Glu Ser Leu Ala Gln Ala Leu Arg Val Ile Asp Ile Tyr Thr
305                 310                 315                 320
His Arg Trp Arg Ile Glu Glu Phe His Lys Ala Trp Lys Thr Gly Ala
                325                 330                 335
Gly Ala Glu Arg Gln Arg Met Glu Glu Pro Asp Asn Leu Glu Arg Met
            340                 345                 350
Val Ser Ile Leu Ser Phe Val Ala Val Arg Leu Leu Gln Leu Arg Glu
            355                 360                 365
Ser Phe Thr Pro Pro Gln Ala Leu Arg Ala Gln Gly Leu Leu Lys Glu
    370                 375                 380
Ala Glu His Val Glu Ser Gln Ser Ala Glu Thr Val Leu Thr Pro Asp
385                 390                 395                 400
Glu Cys Gln Leu Leu Gly Tyr Leu Asp Lys Gly Lys Arg Lys Arg Lys
                405                 410                 415
Glu Lys Ala Gly Ser Leu Gln Trp Ala Tyr Met Ala Ile Ala Arg Leu
            420                 425                 430
Gly Gly Phe Met Asp Ser Lys Arg Thr Gly Ile Ala Ser Trp Gly Ala
            435                 440                 445
Leu Trp Glu Gly Trp Glu Ala Leu Gln Ser Lys Leu Asp Gly Phe Leu
    450                 455                 460
```

```
Ala Ala Lys Asp Leu Met Ala Gln Gly Ile Lys Ile
465                 470                 475

(2) INFORMATION FOR SEQ ID NO:3:

(i) SEQUENCE CHARACTERISTICS:
        (A) LENGTH: 5838 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid DNA"

(vii) IMMEDIATE SOURCE:
        (B) CLONE: pRZTL1

(ix) FEATURE:
        (A) NAME/KEY: insertion_seq
        (B) LOCATION: 1..19

(ix) FEATURE:
        (A) NAME/KEY: CDS
        (B) LOCATION: 77..1267
        (D) OTHER INFORMATION: /function= "tetracycline
            resistance"

(ix) FEATURE:
        (A) NAME/KEY: CDS
        (B) LOCATION: complement (2301..2960)
        (D) OTHER INFORMATION: /function= "chloramphenicol
            resistance"

(ix) FEATURE:
        (A) NAME/KEY: insertion_seq
        (B) LOCATION: 4564..4582

(ix) FEATURE:
        (A) NAME/KEY: CDS
        (B) LOCATION: 4715..5530
        (D) OTHER INFORMATION: /function= "kanamycin resistance"

(xi) SEQUENCE DESCRIPTION: SEQ ID NO:3:
```

| | |
|---|---|
| CTGACTCTTA TACACAAGTA AGCTTTAATG CGGTAGTTTA TCACAGTTAA ATTGCTAACG | 60 |
| CAGTCAGGCA CCGTGT ATG AAA TCT AAC AAT GCG CTC ATC GTC ATC CTC<br>              Met Lys Ser Asn Asn Ala Leu Ile Val Ile Leu<br>                                       480                 485 | 109 |
| GGC ACC GTC ACC CTG GAT GCT GTA GGC ATA GGC TTG GTT ATG CCG GTA<br>Gly Thr Val Thr Leu Asp Ala Val Gly Ile Gly Leu Val Met Pro Val<br>    490                 495                 500 | 157 |
| CTG CCG GGC CTC TTG CGG GAT ATC GTC CAT TCC GAC AGC ATC GCC AGT<br>Leu Pro Gly Leu Leu Arg Asp Ile Val His Ser Asp Ser Ile Ala Ser<br>505                 510                 515                 520 | 205 |
| CAC TAT GGC GTG CTG CTA GCG CTA TAT GCG TTG ATG CAA TTT CTA TGC<br>His Tyr Gly Val Leu Leu Ala Leu Tyr Ala Leu Met Gln Phe Leu Cys<br>                    525                 530                 535 | 253 |
| GCA CCC GTT CTC GGA GCA CTG TCC GAC CGC TTT GGC CGC CGC CCA GTC<br>Ala Pro Val Leu Gly Ala Leu Ser Asp Arg Phe Gly Arg Arg Pro Val<br>                540                 545                 550 | 301 |
| CTG CTC GCT TCG CTA CTT GGA GCC ACT ATC GAC TAC GCG ATC ATG GCG<br>Leu Leu Ala Ser Leu Leu Gly Ala Thr Ile Asp Tyr Ala Ile Met Ala<br>            555                 560                 565 | 349 |
| ACC ACA CCC GTC CTG TGG ATC CTC TAC GCC GGA CGC ATC GTG GCC GGC<br>Thr Thr Pro Val Leu Trp Ile Leu Tyr Ala Gly Arg Ile Val Ala Gly<br>        570                 575                 580 | 397 |
| ATC ACC GGC GCC ACA GGT GCG GTT GCT GGC GCC TAT ATC GCC GAC ATC<br>Ile Thr Gly Ala Thr Gly Ala Val Ala Gly Ala Tyr Ile Ala Asp Ile<br>585                 590                 595                 600 | 445 |

-continued

| | |
|---|---|
| ACC GAT GGG GAA GAT CGG GCT CGC CAC TTC GGG CTC ATG AGC GCT TGT<br>Thr Asp Gly Glu Asp Arg Ala Arg His Phe Gly Leu Met Ser Ala Cys<br>       605              610              615 | 493 |
| TTC GGC GTG GGT ATG GTG GCA GGC CCC GTG GCC GGG GGA CTG TTG GGC<br>Phe Gly Val Gly Met Val Ala Gly Pro Val Ala Gly Gly Leu Leu Gly<br>         620              625              630 | 541 |
| GCC ATC TCC TTG CAT GCA CCA TTC CTT GCG GCG GCG GTG CTC AAC GGC<br>Ala Ile Ser Leu His Ala Pro Phe Leu Ala Ala Ala Val Leu Asn Gly<br>         635              640              645 | 589 |
| CTC AAC CTA CTA CTG GGC TGC TTC CTA ATG CAG GAG TCG CAT AAG GGA<br>Leu Asn Leu Leu Leu Gly Cys Phe Leu Met Gln Glu Ser His Lys Gly<br>     650              655              660 | 637 |
| GAG CGT CGA CCG ATG CCC TTG AGA GCC TTC AAC CCA GTC AGC TCC TTC<br>Glu Arg Arg Pro Met Pro Leu Arg Ala Phe Asn Pro Val Ser Ser Phe<br>665              670              675              680 | 685 |
| CGG TGG GCG CGG GGC ATG ACT ATC GTC GCC GCA CTT ATG ACT GTC TTC<br>Arg Trp Ala Arg Gly Met Thr Ile Val Ala Ala Leu Met Thr Val Phe<br>             685              690              695 | 733 |
| TTT ATC ATG CAA CTC GTA GGA CAG GTG CCG GCA GCG CTC TGG GTC ATT<br>Phe Ile Met Gln Leu Val Gly Gln Val Pro Ala Ala Leu Trp Val Ile<br>         700              705              710 | 781 |
| TTC GGC GAG GAC CGC TTT CGC TGG AGC GCG ACG ATG ATC GGC CTG TCG<br>Phe Gly Glu Asp Arg Phe Arg Trp Ser Ala Thr Met Ile Gly Leu Ser<br>         715              720              725 | 829 |
| CTT GCG GTA TTC GGA ATC TTG CAC GCC CTC GCT CAA GCC TTC GTC ACT<br>Leu Ala Val Phe Gly Ile Leu His Ala Leu Ala Gln Ala Phe Val Thr<br>     730              735              740 | 877 |
| GGT CCC GCC ACC AAA CGT TTC GGC GAG AAG CAG GCC ATT ATC GCC GGC<br>Gly Pro Ala Thr Lys Arg Phe Gly Glu Lys Gln Ala Ile Ile Ala Gly<br>745              750              755              760 | 925 |
| ATG GCG GCC GAC GCG CTG GGC TAC GTC TTG CTG GCG TTC GCG ACG CGA<br>Met Ala Ala Asp Ala Leu Gly Tyr Val Leu Leu Ala Phe Ala Thr Arg<br>             765              770              775 | 973 |
| GGC TGG ATG GCC TTC CCC ATT ATG ATT CTT CTC GCT TCC GGC GGC ATC<br>Gly Trp Met Ala Phe Pro Ile Met Ile Leu Leu Ala Ser Gly Gly Ile<br>         780              785              790 | 1021 |
| GGG ATG CCC GCG TTG CAG GCC ATG CTG TCC AGG CAG GTA GAT GAC GAC<br>Gly Met Pro Ala Leu Gln Ala Met Leu Ser Arg Gln Val Asp Asp Asp<br>         795              800              805 | 1069 |
| CAT CAG GGA CAG CTT CAA GGA TCG CTC GCG GCT CTT ACC AGC CTA ACT<br>His Gln Gly Gln Leu Gln Gly Ser Leu Ala Ala Leu Thr Ser Leu Thr<br>     810              815              820 | 1117 |
| TCG ATC ACT GGA CCG CTG ATC GTC ACG GCG ATT TAT GCC GCC TCG GCG<br>Ser Ile Thr Gly Pro Leu Ile Val Thr Ala Ile Tyr Ala Ala Ser Ala<br>825              830              835              840 | 1165 |
| AGC ACA TGG AAC GGG TTG GCA TGG ATT GTA GGC GCC GCC CTA TAC CTT<br>Ser Thr Trp Asn Gly Leu Ala Trp Ile Val Gly Ala Ala Leu Tyr Leu<br>             845              850              855 | 1213 |
| GTC TGC CTC CCC GCG TTG CGT CGC GGT GCA TGG AGC CGG GCC ACC TCG<br>Val Cys Leu Pro Ala Leu Arg Arg Gly Ala Trp Ser Arg Ala Thr Ser<br>         860              865              870 | 1261 |
| ACC TGA ATGGAAGCCG GCGGCACCTC GCTAACGGAT TCACCACTCC AAGAATTGGA<br>Thr  * | 1317 |
| GCCAATCAAT TCTTGCGGAG AACTGTGAAT GCGCAAACCA ACCCTTGGCA GAACATATCC | 1377 |
| ATCGCGTCCG CCATCTCCAG CAGCCGCACG CGGCGCATCT CGGGCAGCGT TGGGTCCTGG | 1437 |
| CCACGGGTGC GCATGATCGT GCTCCTGTCG TTGAGGACCC GGCTAGGCTG GCGGGGTTGC | 1497 |
| CTTACTGGTT AGCAGAATGA ATCACCGATA CGCGAGCGAA CGTGAAGCGA CTGCTGCTGC | 1557 |
| AAAACGTCTG CGACCTGAGC AACAACATGA ATGGTCTTCG GTTTCCGTGT TTCGTAAAGT | 1617 |

```
CTGGAAACGC GGAAGTCCCC TACGTGCTGC TGAAGTTGCC CGCAACAGAG AGTGGAACCA    1677
ACCGGTGATA CCACGATACT ATGACTGAGA GTCAACGCCA TGAGCGGCCT CATTTCTTAT    1737
TCTGAGTTAC AACAGTCCGC ACCGCTGTCC GGTAGCTCCT TCCGGTGGGC GCGGGGCATG    1797
ACTATCGTCG CCGCACTTAT GACTGTCTTC TTTATCATGC AACTCGTAGG ACAGGTGCCG    1857
GCAGCGCCCA ACAGTCCCCC GGCCACGGGG CCTGCCACCA TACCCACGCC GAAACAAGCG    1917
CCCTGCACCA TTATGTTCCG GATCTGCATC GCAGGATGCT GCTGGCTACC CTGTGGAACA    1977
CCTACATCTG TATTAACGAA GCGCTAACCG TTTTTATCAG GCTCTGGGAG GCAGAATAAA    2037
TGATCATATC GTCAATTATT ACCTCCACGG GGAGAGCCTG AGCAAACTGG CCTCAGGCAT    2097
TTGAGAAGCA CACGGTCACA CTGCTTCCGG TAGTCAATAA ACCGGTAAAC CAGCAATAGA    2157
CATAAGCGGC TATTTAACGA CCCTGCCCTG AACCGACGAC CGGGTCGAAT TGCTTTCGA     2217
ATTTCTGCCA TTCATCCGCT TATTATCAAT TATTCAGGCG TAGCACCAGG CGTTTAAGGG    2277
CACCAATAAC TGCCTTAAAA AAATTACGCC CCGCCCTGCC ACTCATCGCA GTACTGTTGT    2337
AATTCATTAA GCATTCTGCC GACATGGAAG CCATCACAGA CGGCATGATG AACCTGAATC    2397
GCCAGCGGCA TCAGCACCTT GTCGCCTTGC GTATAATATT TGCCCATGGT GAAAACGGGG    2457
GCGAAGAAGT TGTCCATATT GGCCACGTTT AAATCAAAAC TGGTGAAACT CACCCAGGGA    2517
TTGGCTGAGA CGAAAAACAT ATTCTCAATA AACCCTTTAG GGAAATAGGC CAGGTTTTCA    2577
CCGTAACACG CCACATCTTG CGAATATATG TGTAGAAACT GCCGGAAATC GTCGTGGTAT    2637
TCACTCCAGA GCGATGAAAA CGTTTCAGTT TGCTCATGGA AAACGGTGTA ACAAGGGTGA    2697
ACACTATCCC ATATCACCAG CTCACCGTCT TCATTGCCA TACGGAATTC CGGATGAGCA    2757
TTCATCAGGC GGGCAAGAAT GTGAATAAAG GCCGGATAAA ACTTGTGCTT ATTTTTCTTT    2817
ACGGTCTTTA AAAAGGCCGT AATATCCAGC TGAACGGTCT GGTTATAGGT ACATTGAGCA    2877
ACTGACTGAA ATGCCTCAAA ATGTTCTTTA CGATGCCATT GGGATATATC AACGGTGGTA    2937
TATCCAGTGA TTTTTTTCTC CATTTTAGCT TCCTTAGCTC CTGAAAATCT CGATAACTCA    2997
AAAAATACGC CCGGTAGTGA TCTTATTTCA TTATGGTGAA AGTTGGAACC TCTTACGTGC    3057
CGATCAACGT CTCATTTTCG CCAAAAGTTG GCCCAGGGCT TCCCGGTATC AACAGGGACA    3117
CCAGGATTTA TTTATTCTGC GAAGTGATCT TCCGTCACAG GTATTTATTC GGCGCAAAGT    3177
GCGTCGGGTG ATGCTGCCAA CTTACTGATT TAGTGTATGA TGGTGTTTTT GAGGTGCTCC    3237
AGTGGCTTCT GTTTCTATCA GCTGTCCCTC CTGTTCAGCT ACTGACGGGG TGGTGCGTAA    3297
CGGCAAAAGC ACCGCCGGAC ATCAGCGCTA GCGGAGTGTA TACTGGCTTA CTATGTTGGC    3357
ACTGATGAGG GTGTCAGTGA AGTGCTTCAT GTGGCAGGAG AAAAAAGGCT GCACCGGTGC    3417
GTCAGCAGAA TATGTGATAC AGGATATATT CCGCTTCCTC GCTCACTGAC TCGCTACGCT    3477
CGGTCGTTCG ACTGCGGCGA GCGGAAATGG CTTACGAACG GGGCGGAGAT TTCCTGGAAG    3537
ATGCCAGGAA GATACTTAAC AGGGAAGTGA GAGGGCCGCG GCAAAGCCGT TTTTCCATAG    3597
GCTCCGCCCC CCTGACAAGC ATCACGAAAT CTGACGCTCA AATCAGTGGT GGCGAAACCC    3657
GACAGGACTA TAAAGATACC AGGCGTTTCC CCTGGCGGCT CCCTCGTGCG CTCTCCTGTT    3717
CCTGCCTTTC GGTTTACCGG TGTCATTCCG CTGTTATGGC CGCGTTTGTC TCATTCCACG    3777
CCTGACACTC AGTTCCGGGT AGGCAGTTCG CTCCAAGCTG GACTGTATGC ACGAACCCCC    3837
CGTTCAGTCC GACCGCTGCG CCTTATCCGG TAACTATCGT CTTGAGTCCA ACCCGGAAAG    3897
ACATGCAAAA GCACCACTGG CAGCAGCCAC TGGTAATTGA TTTAGAGGAG TTAGTCTTGA    3957
AGTCATGCGC CGGTTAAGGC TAAACTGAAA GGACAAGTTT TGGTGACTGC GCTCCTCCAA    4017
```

```
GCCAGTTACC TCGGTTCAAA GAGTTGGTAG CTCAGAGAAC CTTCGAAAAA CCGCCCTGCA    4077

AGGCGGTTTT TTCGTTTTCA GAGCAAGAGA TTACGCGCAG ACCAAAACGA TCTCAAGAAG    4137

ATCATCTTAT TAATCAGATA AAATATTTCT AGAGGTGAAC CATCACCCTA ATCAAGTTTT    4197

TTGGGGTCGA GGTGCCGTAA AGCACTAAAT CGGAACCCTA AAGGGATGCC CCGATTTAGA    4257

GCTTGACGGG GAAAGCCGGC GAACGTGGCG AGAAAGGAAG GGAAGAAAGC GAAAGGAGCG    4317

GGCGCTAGGG CGCTGGCAAG TGTAGCGGTC ACGCTGCGCG TAACCACCAC ACCCGCCGCG    4377

CTTAATGCGC CGCTACAGCG CCATTCGCCA TTCAGGCTGC GCAACTGTTG GAAGGGCGA    4437

TCGGTGCGGG CCTCTTCGCT ATTACGCCAG CTGGCGAAAG GGGGATGTGC TGCAAGGCGA    4497

TTAAGTTGGG TAACGCCAGG GTTTTCCCAG TCACGACGTT GTAAAACGAC GGCCAGTGCC    4557

AAGCTTACTT GTGTATAAGA GTCAGTCGAC CTGCAGGGGG GGGGGGGAAA GCCACGTTGT    4617

GTCTCAAAAT CTCTGATGTT ACATTGCACA AGATAAAAAT ATATCATCAT GAACAATAAA    4677

ACTGTCTGCT TACATAAACA GTAATACAAG GGGTGTT ATG AGC CAT ATT CAA CGG    4732
                                          Met Ser His Ile Gln Arg
                                           1               5

GAA ACG TCT TGC TCG AGG CCG CGA TTA AAT TCC AAC ATG GAT GCT GAT    4780
Glu Thr Ser Cys Ser Arg Pro Arg Leu Asn Ser Asn Met Asp Ala Asp
            10                  15                  20

TTA TAT GGG TAT AAA TGG GCT CGC GAT AAT GTC GGG CAA TCA GGT GCG    4828
Leu Tyr Gly Tyr Lys Trp Ala Arg Asp Asn Val Gly Gln Ser Gly Ala
        25                  30                  35

ACA ATC TAT CGA TTG TAT GGG AAG CCC GAT GCG CCA GAG TTG TTT CTG    4876
Thr Ile Tyr Arg Leu Tyr Gly Lys Pro Asp Ala Pro Glu Leu Phe Leu
    40                  45                  50

AAA CAT GGC AAA GGT AGC GTT GCC AAT GAT GTT ACA GAT GAG ATG GTC    4924
Lys His Gly Lys Gly Ser Val Ala Asn Asp Val Thr Asp Glu Met Val
55                  60                  65                  70

AGA CTA AAC TGG CTG ACG GAA TTT ATG CCT CTT CCG ACC ATC AAG CAT    4972
Arg Leu Asn Trp Leu Thr Glu Phe Met Pro Leu Pro Thr Ile Lys His
                75                  80                  85

TTT ATC CGT ACT CCT GAT GAT GCA TGG TTA CTC ACC ACT GCG ATC CCC    5020
Phe Ile Arg Thr Pro Asp Asp Ala Trp Leu Leu Thr Thr Ala Ile Pro
            90                  95                 100

GGG AAA ACA GCA TTC CAG GTA TTA GAA GAA TAT CCT GAT TCA GGT GAA    5068
Gly Lys Thr Ala Phe Gln Val Leu Glu Glu Tyr Pro Asp Ser Gly Glu
        105                 110                 115

AAT ATT GTT GAT GCG CTG GCA GTG TTC CTG CGC CGG TTG CAT TCG ATT    5116
Asn Ile Val Asp Ala Leu Ala Val Phe Leu Arg Arg Leu His Ser Ile
    120                 125                 130

CCT GTT TGT AAT TGT CCT TTT AAC AGC GAT CGC GTA TTT CGT CTC GCT    5164
Pro Val Cys Asn Cys Pro Phe Asn Ser Asp Arg Val Phe Arg Leu Ala
135                 140                 145                 150

CAG GCG CAA TCA CGA ATG AAT AAC GGT TTG GTT GAT GCG AGT GAT TTT    5212
Gln Ala Gln Ser Arg Met Asn Asn Gly Leu Val Asp Ala Ser Asp Phe
                155                 160                 165

GAT GAC GAG CGT AAT GGC TGG CCT GTT GAA CAA GTC TGG AAA GAA ATG    5260
Asp Asp Glu Arg Asn Gly Trp Pro Val Glu Gln Val Trp Lys Glu Met
            170                 175                 180

CAT AAG CTT TTG CCA TTC TCA CCG GAT TCA GTC GTC ACT CAT GGT GAT    5308
His Lys Leu Leu Pro Phe Ser Pro Asp Ser Val Val Thr His Gly Asp
        185                 190                 195

TTC TCA CTT GAT AAC CTT ATT TTT GAC GAG GGG AAA TTA ATA GGT TGT    5356
Phe Ser Leu Asp Asn Leu Ile Phe Asp Glu Gly Lys Leu Ile Gly Cys
    200                 205                 210
```

```
ATT GAT GTT GGA CGA GTC GGA ATC GCA GAC CGA TAC CAG GAT CTT GCC    5404
Ile Asp Val Gly Arg Val Gly Ile Ala Asp Arg Tyr Gln Asp Leu Ala
215                 220                 225                 230

ATC CTA TGG AAC TGC CTC GGT GAG TTT TCT CCT TCA TTA CAG AAA CGG    5452
Ile Leu Trp Asn Cys Leu Gly Glu Phe Ser Pro Ser Leu Gln Lys Arg
            235                 240                 245

CTT TTT CAA AAA TAT GGT ATT GAT AAT CCT GAT ATG AAT AAA TTG CAG    5500
Leu Phe Gln Lys Tyr Gly Ile Asp Asn Pro Asp Met Asn Lys Leu Gln
        250                 255                 260

TTT CAT TTG ATG CTC GAT GAG TTT TTC TAA TCAGAATTGG TTAATTGGTT      5550
Phe His Leu Met Leu Asp Glu Phe Phe *
    265                 270

GTAACACTGG CAGAGCATTA CGCTGACTTG ACGGGACGGC GGCTTTGTTG AATAAATCGA  5610

ACTTTTGCTG AGTTGAAGGA TCAGATCACG CATCTTCCCG ACAACGCAGA CCGTTCCGTG  5670

GCAAAGCAAA AGTTCAAAAT CACCAACTGG TCCACCTACA ACAAAGCTCT CATCAACCGT  5730

GGCTCCCTCA CTTTCTGGCT GGATGATGGG GCGATTCAGG CCTGGTATGA GTCAGCAACA  5790

CCTTCTTCAC GAGGCAGACC TCAGCGCCCC CCCCCCCCTG CAGGTCGA               5838

(2) INFORMATION FOR SEQ ID NO:4:

(i) SEQUENCE CHARACTERISTICS:
        (A) LENGTH:  396 amino acids
        (B) TYPE: amino acid
        (D) TOPOLOGY: linear (ii) MOLECULE TYPE: protein (xi) SEQUENCE DESCRIPTION: SEQ ID NO:4:

Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Gly Leu Leu Gly Ala Ile Ser Leu His
145                 150                 155                 160

Ala Pro Phe Leu Ala Ala Val Leu Asn Gly Leu Asn Leu Leu
                165                 170                 175

Gly Cys Phe Leu Met Gln Glu Ser His Lys Gly Glu Arg Arg Pro Met
        180                 185                 190

Pro Leu Arg Ala Phe Asn Pro Val Ser Ser Phe Arg Trp Ala Arg Gly
    195                 200                 205

Met Thr Ile Val Ala Ala Leu Met Thr Val Phe Phe Ile Met Gln Leu
210                 215                 220
```

```
Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285

Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
        355                 360                 365

Leu Ala Trp Ile Val Gly Ala Ala Leu Tyr Leu Val Cys Leu Pro Ala
    370                 375                 380

Leu Arg Arg Gly Ala Trp Ser Arg Ala Thr Ser Thr
385                 390                 395
```

(2) INFORMATION FOR SEQ ID NO:5:

(i) SEQUENCE CHARACTERISTICS:
        (A) LENGTH: 219 amino acids
        (B) TYPE: amino acid
        (D) TOPOLOGY: linear (ii) MOLECULE TYPE: protein (xi) SEQUENCE DESCRIPTION: SEQ ID NO:5:

```
Met Glu Lys Lys Ile Thr Gly Tyr Thr Thr Val Asp Ile Ser Gln Trp
1               5                   10                  15

His Arg Lys Glu His Phe Glu Ala Phe Gln Ser Val Ala Gln Cys Thr
                20                  25                  30

Tyr Asn Gln Thr Val Gln Leu Asp Ile Thr Ala Phe Leu Lys Thr Val
            35                  40                  45

Lys Lys Asn Lys His Lys Phe Tyr Pro Ala Phe Ile His Ile Leu Ala
        50                  55                  60

Arg Leu Met Asn Ala His Pro Glu Phe Arg Met Ala Met Lys Asp Gly
65                  70                  75                  80

Glu Leu Val Ile Trp Asp Ser Val His Pro Cys Tyr Thr Val Phe His
                85                  90                  95

Glu Gln Thr Glu Thr Phe Ser Ser Leu Trp Ser Glu Tyr His Asp Asp
            100                 105                 110

Phe Arg Gln Phe Leu His Ile Tyr Ser Gln Asp Val Ala Cys Tyr Gly
        115                 120                 125

Glu Asn Leu Ala Tyr Phe Pro Lys Gly Phe Ile Glu Asn Met Phe Phe
    130                 135                 140

Val Ser Ala Asn Pro Trp Val Ser Phe Thr Ser Phe Asp Leu Asn Val
145                 150                 155                 160

Ala Asn Met Asp Asn Phe Phe Ala Pro Val Phe Thr Met Gly Lys Tyr
                165                 170                 175

Tyr Thr Gln Gly Asp Lys Val Leu Met Pro Leu Ala Ile Gln Val His
            180                 185                 190
```

His Ala Val Cys Asp Gly Phe His Val Gly Arg Met Leu Asn Glu Leu
        195                 200                 205

Gln Gln Tyr Cys Asp Glu Trp Gln Gly Gly Ala
210                 215                 220

(2) INFORMATION FOR SEQ ID NO:6:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:6:

Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
            20                  25                  30

Val Gly Gln Ser Gly Ala Thr Ile Tyr Arg Leu Tyr Gly Lys Pro Asp
        35                  40                  45

Ala Pro Glu Leu Phe Leu Lys His Gly Lys Gly Ser Val Ala Asn Asp
    50                  55                  60

Val Thr Asp Glu Met Val Arg Leu Asn Trp Leu Thr Glu Phe Met Pro
65                  70                  75                  80

Leu Pro Thr Ile Lys His Phe Ile Arg Thr Pro Asp Asp Ala Trp Leu
                85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
225                 230                 235                 240

Pro Ser Leu Gln Lys Arg Leu Phe Gln Lys Tyr Gly Ile Asp Asn Pro
                245                 250                 255

Asp Met Asn Lys Leu Gln Phe His Leu Met Leu Asp Glu Phe Phe
            260                 265                 270

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid (A) DESCRIPTION: /desc = "Tn5 wild type outside end"

(xi) SEQUENCE DESCRIPTION: SEQ ID NO:7:

CTGACTCTTA TACACAAGT                                                      19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 mutant outside end"

(xi) SEQUENCE DESCRIPTION: SEQ ID NO:8:

CTGTCTCTTA TACACATCT                                                      19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 mutant outside end"

(xi) SEQUENCE DESCRIPTION: SEQ ID NO:9:

CTGTCTCTTA TACAGATCT                                                      19

(2) INFORMATION FOR SEQ ID NO:10:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: other nucleic acid
        (A) DESCRIPTION: /desc = "Tn5 wild type inside end"

(xi) SEQUENCE DESCRIPTION: SEQ ID NO:10:

CTGTCTCTTG ATCAGATCT                                                      19

(2) INFORMATION FOR SEQ ID NO:11:

(i) SEQUENCE CHARACTERISTICS:
        (A) LENGTH: 19182 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid pRZ4196"

(ix) FEATURE:
        (A) NAME/KEY: repeat_unit
        (B) LOCATION: 94..112
        (D) OTHER INFORMATION: /note= "Wild type OE sequence"

(ix) FEATURE:
        (A) NAME/KEY: repeat_unit
        (B) LOCATION: 12184..12225
        (D) OTHER INFORMATION: /note= "Cassette IE"

(xi) SEQUENCE DESCRIPTION: SEQ ID NO:11:

TTCCTGTAAC AATAGCAATA CCCCAAATAC CTAATGTAGT TCCAGCAAGC AAGCTAAAAA          60

-continued

```
GTAAAGCAAC AACATAACTC ACCCCTGCAT CTGCTGACTC TTATACACAA GTAGCGTCCC     120

GGGATCGGGA TCCCGTCGTT TTACAACGTC GTGACTGGGA AAACCCTGGC GTTACCCAAC     180

TTAATCGCCT TGCAGCACAT CCCCCTTTCG CCAGCTGGCG TAATAGCGAA GAGGCCCGCA     240

CCGATCGCCC TTCCCAACAG TTGCGCAGCC TGAATGGCGA ATGGCGCTTT GCCTGGTTTC     300

CGGCACCAGA AGCGGTGCCG GAAAGCTGGC TGGAGTGCGA TCTTCCTGAG GCCGATACTG     360

TCGTCGTCCC CTCAAACTGG CAGATGCACG GTTACGATGC GCCCATCTAC ACCAACGTAA     420

CCTATCCCAT TACGGTCAAT CCGCCGTTTG TTCCCACGGA GAATCCGACG GGTTGTTACT     480

CGCTCACATT TAATGTTGAT GAAAGCTGGC TACAGGAAGG CCAGACGCGA ATTATTTTTG     540

ATGGCGTTAA CTCGGCGTTT CATCTGTGGT GCAACGGGCG CTGGGTCGGT TACGGCCAGG     600

ACAGTCGTTT GCCGTCTGAA TTTGACCTGA GCGCATTTTT ACGCGCCGGA GAAAACCGCC     660

TCGCGGTGAT GGTGCTGCGT TGGAGTGACG GCAGTTATCT GGAAGATCAG GATATGTGGC     720

GGATGAGCGG CATTTTCCGT GACGTCTCGT TGCTGCATAA ACCGACTACA CAAATCAGCG     780

ATTTCCATGT TGCCACTCGC TTTAATGATG ATTTCAGCCG CGCTGTACTG GAGGCTGAAG     840

TTCAGATGTG CGGCGAGTTG CGTGACTACC TACGGGTAAC AGTTTCTTTA TGGCAGGGTG     900

AAACGCAGGT CGCCAGCGGC ACCGCGCCTT TCGGCGGTGA AATTATCGAT GAGCGTGGTG     960

GTTATGCCGA TCGCGTCACA CTACGTCTGA ACGTCGAAAA CCCGAAACTG TGGAGCGCCG    1020

AAATCCCGAA TCTCTATCGT GCGGTGGTTG AACTGCACAC CGCCGACGGC ACGCTGATTG    1080

AAGCAGAAGC CTGCGATGTC GGTTTCCGCG AGGTGCGGAT TGAAAATGGT CTGCTGCTGC    1140

TGAACGGCAA GCCGTTGCTG ATTCGAGGCG TTAACCGTCA CGAGCATCAT CCTCTGCATG    1200

GTCAGGTCAT GGATGAGCAG ACGATGGTGC AGGATATCCT GCTGATGAAG CAGAACAACT    1260

TTAACGCCGT GCGCTGTTCG CATTATCCGA ACCATCCGCT GTGGTACACG CTGTGCGACC    1320

GCTACGGCCT GTATGTGGTG GATGAAGCCA ATATTGAAAC CCACGGCATG GTGCCAATGA    1380

ATCGTCTGAC CGATGATCCG CGCTGGCTAC CGGCGATGAG CGAACGCGTA ACGCGAATGG    1440

TGCAGCGCGA TCGTAATCAC CCGAGTGTGA TCATCTGGTC GCTGGGGAAT GAATCAGGCC    1500

ACGGCGCTAA TCACGACGCG CTGTATCGCT GGATCAAATC TGTCGATCCT TCCCGCCCGG    1560

TGCAGTATGA AGGCGGCGGA GCCGACACCA CGGCCACCGA TATTATTTGC CCGATGTACG    1620

CGCGCGTGGA TGAAGACCAG CCCTTCCCGG CTGTGCCGAA ATGGTCCATC AAAAAATGGC    1680

TTTCGCTACC TGGAGAGACG CGCCCGCTGA TCCTTTGCGA ATACGCCCAC GCGATGGGTA    1740

ACAGTCTTGG CGGTTTCGCT AAATACTGGC AGGCGTTTCG TCAGTATCCC CGTTTACAGG    1800

GCGGCTTCGT CTGGGACTGG GTGGATCAGT CGCTGATTAA ATATGATGAA AACGGCAACC    1860

CGTGGTCGGC TTACGGCGGT GATTTTGGCG ATACGCCGAA CGATCGCCAG TTCTGTATGA    1920

ACGGTCTGGT CTTTGCCGAC CGCACGCCGC ATCCAGCGCT GACGGAAGCA AAACACCAGC    1980

AGCAGTTTTT CCAGTTCCGT TTATCCGGGC AAACCATCGA AGTGACCAGC GAATACCTGT    2040

TCCGTCATAG CGATAACGAG CTCCTGCACT GGATGGTGGC GCTGGATGGT AAGCCGCTGG    2100

CAAGCGGTGA AGTGCCTCTG GATGTCGCTC CACAAGGTAA ACAGTTGATT GAACTGCCTG    2160

AACTACCGCA GCCGGAGAGC GCCGGGCAAC TCTGGCTCAC AGTACGCGTA GTGCAACCGA    2220

ACGCGACCGC ATGGTCAGAA GCCGGGCACA TCAGCGCCTG GCAGCAGTGG CGTCTGGCGG    2280

AAAACCTCAG TGTGACGCTC CCCGCCGCGT CCCACGCCAT CCCGCATCTG ACCACCAGCG    2340

AAATGGATTT TTGCATCGAG CTGGGTAATA AGCGTTGGCA ATTTAACCGC CAGTCAGGCT    2400

TTCTTTCACA GATGTGGATT GGCGATAAAA AACAACTGCT GACGCCGCTG CGCGATCAGT    2460
```

```
TCACCCGTGC ACCGCTGGAT AACGACATTG GCGTAAGTGA AGCGACCCGC ATTGACCCTA    2520

ACGCCTGGGT CGAACGCTGG AAGGCGGCGG GCCATTACCA GGCCGAAGCA GCGTTGTTGC    2580

AGTGCACGGC AGATACACTT GCTGATGCGG TGCTGATTAC GACCGCTCAC GCGTGGCAGC    2640

ATCAGGGGAA AACCTTATTT ATCAGCCGGA AAACCTACCG GATTGATGGT AGTGGTCAAA    2700

TGGCGATTAC CGTTGATGTT GAAGTGGCGA GCGATACACC GCATCCGGCG CGGATTGGCC    2760

TGAACTGCCA GCTGGCGCAG GTAGCAGAGC GGGTAAACTG GCTCGGATTA GGGCCGCAAG    2820

AAAACTATCC CGACCGCCTT ACTGCCGCCT GTTTTGACCG CTGGGATCTG CCATTGTCAG    2880

ACATGTATAC CCCGTACGTC TTCCCGAGCG AAAACGGTCT GCGCTGCGGG ACGCGCGAAT    2940

TGAATTATGG CCCACACCAG TGGCGCGGCG ACTTCCAGTT CAACATCAGC CGCTACAGTC    3000

AACAGCAACT GATGGAAACC AGCCATCGCC ATCTGCTGCA CGCGGAAGAA GGCACATGGC    3060

TGAATATCGA CGGTTTCCAT ATGGGGATTG GTGGCGACGA CTCCTGGAGC CCGTCAGTAT    3120

CGGCGGATTC CAGCTGAGCG CCGGTCGCTA CCATTACCAG TTGGTCTGGT GTCAAAAATA    3180

ATAATAACCG GGCAGGCCAT GTCTGCCCGT ATTTCGCGTA AGGAAATCCA TTATGTACTA    3240

TTTAAAAAAC ACAAACTTTT GGATGTTCGG TTTATTCTTT TTCTTTTACT TTTTTATCAT    3300

GGGAGCCTAC TTCCCGTTTT TCCCGATTTG GCTACATGAC ATCAACCATA TCAGCAAAAG    3360

TGATACGGGT ATTATTTTTG CCGCTATTTC TCTGTTCTCG CTATTATTCC AACCGCTGTT    3420

TGGTCTGCTT TCTGACAAAC TCGGGCTGCG CAAATACCTG CTGTGGATTA TTACCGGCAT    3480

GTTAGTGATG TTTGCGCCGT TCTTTATTTT TATCTTCGGG CCACTGTTAC AATACAACAT    3540

TTTAGTAGGA TCGATTGTTG GTGGTATTTA TCTAGGCTTT TGTTTAACG CCGGTGCGCC    3600

AGCAGTAGAG GCATTTATTG AGAAAGTCAG CCGTCGCAGT AATTTCGAAT TTGGTCGCGC    3660

GCGGATGTTT GGCTGTGTTG GCTGGGCGCT GTGTGCCTCG ATTGTCGGCA TCATGTTCAC    3720

CATCAATAAT CAGTTTGTTT TCTGGCTGGG CTCTGGCTGT GCACTCATCC TCGCCGTTTT    3780

ACTCTTTTTC GCCAAAACGG ATGCGCCCTC TTCTGCCACG GTTGCCAATG CGGTAGGTGC    3840

CAACCATTCG GCATTTAGCC TTAAGCTGGC ACTGGAACTG TTCAGACAGC CAAAACTGTG    3900

GTTTTTGTCA CTGTATGTTA TTGGCGTTTC CTGCACCTAC GATGTTTTTG ACCAACAGTT    3960

TGCTAATTTC TTTACTTCGT TCTTTGCTAC CGGTGAACAG GGTACGCGGG TATTTGGCTA    4020

CGTAACGACA ATGGGCGAAT TACTTAACGC CTCGATTATG TTCTTTGCGC CACTGATCAT    4080

TAATCGCATC GGTGGGAAAA ACGCCCTGCT GCTGGCTGGC ACTATTATGT CTGTACGTAT    4140

TATTGGCTCA TCGTTCGCCA CCTCAGCGCT GGAAGTGGTT ATTCTGAAAA CGCTGCATAT    4200

GTTTGAAGTA CCGTTCCTGC TGGTGGGCTG CTTTAAATAT ATTACCAGCC AGTTTGAAGT    4260

GCGTTTTTCA GCGACGATTT ATCTGGTCTG TTTCTGCTTC TTTAAGCAAC TGGCGATGAT    4320

TTTTATGTCT GTACTGGCGG GCAATATGTA TGAAAGCATC GGTTTCCAGG GCGCTTATCT    4380

GGTGCTGGGT CTGGTGGCGC TGGGCTTCAC CTTAATTTCC GTGTTCACGC TTAGCGGCCC    4440

CGGCCCGCTT TCCCTGCTGC GTCGTCAGGT GAATGAAGTC GCTTAAGCAA TCAATGTCGG    4500

ATGCGGCGCG ACGCTTATCC GACCAACATA TCATAACGGA GTGATCGCAT TGAACATGCC    4560

AATGACCGAA AGAATAAGAG CAGGCAAGCT ATTTACCGAT ATGTGCGAAG GCTTACCGGA    4620

AAAAAGACTT CGTGGGAAAA CGTTAATGTA TGAGTTTAAT CACTCGCATC CATCAGAAGT    4680

TGAAAAAGA GAAAGCCTGA TTAAAGAAAT GTTTGCCACG GTAGGGGAAA ACGCCTGGGT    4740

AGAACCGCCT GTCTATTTCT CTTACGGTTC CAACATCCAT ATAGGCCGCA ATTTTTATGC    4800

AAATTTCAAT TTAACCATTG TCGATGACTA CACGGTAACA ATCGGTGATA ACGTACTGAT    4860
```

```
TGCACCCAAC GTTACTCTTT CCGTTACGGG ACACCCTGTA CACCATGAAT TGAGAAAAAA    4920
CGGCGAGATG TACTCTTTTC CGATAACGAT TGGCAATAAC GTCTGGATCG AAGTCATGT     4980
GGTTATTAAT CCAGGCGTCA CCATCGGGGA TAATTCTGTT ATTGGCGCGG GTAGTATCGT    5040
CACAAAAGAC ATTCCACCAA ACGTCGTGGC GGCTGGCGTT CCTTGTCGGG TTATTCGCGA    5100
AATAAACGAC CGGGATAAGC ACTATTATTT CAAAGATTAT AAAGTTGAAT CGTCAGTTTA    5160
AATTATAAAA ATTGCCTGAT ACGCTGCGCT TATCAGGCCT ACAAGTTCAG CGATCTACAT    5220
TAGCCGCATC CGGCATGAAC AAAGCGCAGG AACAAGCGTC GCATCATGCC TCTTTGACCC    5280
ACAGCTGCGG AAAACGTACT GGTGCAAAAC GCAGGGTTAT GATCATCAGC CCAACGACGC    5340
ACAGCGCATG AAATGCCCAG TCCATCAGGT AATTGCCGCT GATACTACGC AGCACGCCAG    5400
AAAACCACGG GGCAAGCCCG GCGATGATAA AACCGATTCC CTGCATAAAC GCCACCAGCT    5460
TGCCAGCAAT AGCCGGTTGC ACAGAGTGAT CGAGCGCCAG CAGCAAACAG AGCGGAAACG    5520
CGCCGCCCAG ACCTAACCCA CACACCATCG CCCACAATAC CGGCAATTGC ATCGGCAGCC    5580
AGATAAAGCC GCAGAACCCC ACCAGTTGTA ACACCAGCGC CAGCATTAAC AGTTTGCGCC    5640
GATCCTGATG GCGAGCCATA GCAGGCATCA GCAAAGCTCC TGCGGCTTGC CCAAGCGTCA    5700
TCAATGCCAG TAAGGAACCG CTGTACTGCG CGCTGGCACC AATCTCAATA TAGAAAGCGG    5760
GTAACCAGGC AATCAGGCTG GCGTAACCGC CGTTAATCAG ACCGAAGTAA ACACCCAGCG    5820
TCCACGCGCG GGGAGTGAAT ACCACGCGAA CCGGAGTGGT TGTTGTCTTG TGGGAAGAGG    5880
CGACCTCGCG GGCGCTTTGC CACCACCAGG CAAAGAGCGC AACAACGGCA GGCAGCGCCA    5940
CCAGGCGAGT GTTTGATACC AGGTTTCGCT ATGTTGAACT AACCAGGGCG TTATGGCGGC    6000
ACCAAGCCCA CCGCCGCCCA TCAGAGCCGC GGACCACAGC CCCATCACCA GTGGCGTGCG    6060
CTGCTGAAAC CGCCGTTTAA TCACCGAAGC ATCACCGCCT GAATGATGCC GATCCCCACC    6120
CCACCAAGCA GTGCGCTGCT AAGCAGCAGC GCACTTTGCG GGTAAAGCTC ACGCATCAAT    6180
GCACCGACGG CAATCAGCAA CAGACTGATG GCGACACTGC GACGTTCGCT GACATGCTGA    6240
TGAAGCCAGC TTCCGGCCAG CGCCAGCCCG CCCATGGTAA CCACCGGCAG AGCGGTCGAC    6300
CCGGACGGGA CGCTCCTGCG CCTGATACAG AACGAATTGC TTGCAGGCAT CTCATGAGTG    6360
TGTCTTCCCG TTTTCCGCCT GAGGTCACTG CGTGGATGGA GCGCTGGCGC CTGCTGCGCG    6420
ACGGCGAGCT GCTCACCACC CACTCGAGCT GGATACTTCC CGTCCGCCAG GGGGACATGC    6480
CGGCGATGCT GAAGGTCGCG CGCATTCCCG ATGAAGAGGC CGGTTACCGC CTGTTGACCT    6540
GGTGGGACGG GCAGGGCGCC GCCCGAGTCT TCGCCTCGGC GGCGGGCGCT CTGCTCATGG    6600
AGCGCGCGTC CGGGGCCGGG GACCTTGCAC AGATAGCGTG GTCCGGCCAG GACGACGAGG    6660
CTTGCAGGAT CTATGATTCC CTTTGTCAAC AGCAATGGAT CACTGAAAAT GGTTCAATGA    6720
TCACATTAAG TGGTATTCAA TATTTTCATG AAATGGGAAT TGACGTTCCT TCCAAACATT    6780
CACGTAAAAT CTGTTGTGCG TGTTTAGATT GGAGTGAACG CCGTTTCCAT TTAGGTGGGT    6840
ACGTTGGAGC CGCATTATTT TCGCTTTATG AATCTAAAGG GTGGTTAACT CGACATCTTG    6900
GTTACCGTGA AGTTACCATC ACGGAAAAAG GTTATGCTGC TTTTAAGACC CACTTTCACA    6960
TTTAAGTTGT TTTTCTAATC CGCATATGAT CAATTCAAGG CCGAATAAGA AGGCTGGCTC    7020
TGCACCTTGG TGATCAAATA ATTCGATAGC TTGTCGTAAT AATGGCGGCA TACTATCAGT    7080
AGTAGGTGTT TCCCTTTCTT CTTTAGCGAC TTGATGCTCT TGATCTTCCA ATACGCAACC    7140
TAAAGTAAAA TGCCCCACAG CGCTGAGTGC ATATAATGCA TTCTCTAGTG AAAAACCTTG    7200
TTGGCATAAA AAGGCTAATT GATTTTCGAG AGTTTCATAC TGTTTTTCTG TAGGCCGTGT    7260
```

```
ACCTAAATGT ACTTTTGCTC CATCGCGATG ACTTAGTAAA GCACATCTAA AACTTTTAGC    7320

GTTATTACGT AAAAAATCTT GCCAGCTTTC CCCTTCTAAA GGGCAAAAGT GAGTATGGTG    7380

CCTATCTAAC ATCTCAATGG CTAAGGCGTC GAGCAAAGCC CGCTTATTTT TTACATGCCA    7440

ATACAATGTA GGCTGCTCTA CACCTAGCTT CTGGGCGAGT TTACGGGTTG TTAAACCTTC    7500

GATTCCGACC TCATTAAGCA GCTCTAATGC GCTGTTAATC ACTTTACTTT TATCTAATCT    7560

AGACATCATT AATTCCTAAT TTTTGTTGAC ACTCTATCAT TGATAGAGTT ATTTTACCAC    7620

TCCCTATCAG TGATAGAGAA AAGTGAAATG AATAGTTCGA CAAAGATCGC ATTGGTAATT    7680

ACGTTACTCG ATGCCATGGG GATTGGCCTT ATCATGCCAG TCTTGCCAAC GTTATTACGT    7740

GAATTTATTG CTTCGGAAGA TATCGCTAAC CACTTTGGCG TATTGCTTGC ACTTTATGCG    7800

TTAATGCAGG TTATCTTTGC TCCTTGGCTT GGAAAAATGT CTGACCGATT TGGTCGGCGC    7860

CCAGTGCTGT TGTTGTCATT AATAGGCGCA TCGCTGGATT ACTTATTGCT GGCTTTTTCA    7920

AGTGCGCTTT GGATGCTGTA TTTAGGCCGT TTGCTTTCAG GGATCACAGG AGCTACTGGG    7980

GCTGTCGCGG CATCGGTCAT TGCCGATACC ACCTCAGCTT CTCAACGCGT GAAGTGGTTC    8040

GGTTGGTTAG GGGCAAGTTT TGGGCTTGGT TTAATAGCGG GGCCTATTAT TGGTGGTTTT    8100

GCAGGAGAGA TTTCACCGCA TAGTCCCTTT TTTATCGCTG CGTTGCTAAA TATTGTCACT    8160

TTCCTTGTGG TTATGTTTTG GTTCCGTGAA ACCAAAAATA CACGTGATAA TACAGATACC    8220

GAAGTAGGGG TTGAGACGCA ATCGAATTCG GTATACATCA CTTTATTTAA AACGATGCCC    8280

ATTTTGTTGA TTATTTATTT TTCAGCGCAA TTGATAGGCC AAATTCCCGC AACGGTGTGG    8340

GTGCTATTTA CCGAAAATCG TTTTGGATGG AATAGCATGA TGGTTGGCTT TTCATTAGCG    8400

GGTCTTGGTC TTTTACACTC AGTATTCCAA GCCTTTGTGG CAGGAAGAAT AGCCACTAAA    8460

TGGGGCGAAA AAACGGCAGT ACTGCTCGAA TTTATTGCAG ATAGTAGTGC ATTTGCCTTT    8520

TTAGCGTTTA TATCTGAAGG TTGGTTAGAT TTCCCTGTTT TAATTTTATT GGCTGGTGGT    8580

GGGATCGCTT TACCTGCATT ACAGGGAGTG ATGTCTATCC AAACAAAGAG TCATGAGCAA    8640

GGTGCTTTAC AGGGATTATT GGTGAGCCTT ACCAATGCAA CCGGTGTTAT TGGCCCATTA    8700

CTGTTTACTG TTATTTATAA TCATTCACTA CCAATTTGGG ATGGCTGGAT TTGGATTATT    8760

GGTTTAGCGT TTTACTGTAT TATTATCCTG CTATCGATGA CCTTCATGTT AACCCCTCAA    8820

GCTCAGGGGA GTAAACAGGA GACAAGTGCT TAGTTATTTC GTCACCAAAT GATGTTATTC    8880

CGCGAAATAT AATGACCCTC TTGATAACCC AAGAGGGCAT TTTTTACGAT AAAGAAGATT    8940

TAGCTTCAAA TAAAACCTAT CTATTTTATT TATCTTTCAA GCTCAATAAA AAGCCGCGGT    9000

AAATAGCAAT AAATTGGCCT TTTTTATCGG CAAGCTCTTT TAGGTTTTTC GCATGTATTG    9060

CGATATGCAT AAACCAGCCA TTGAGTAAGT TTTTAAGCAC ATCACTATCA TAAGCTTTAA    9120

GTTGGTTCTC TTGGATCAAT TTGCTGACAA TGGCGTTTAC CTTACCAGTA ATGTATTCAA    9180

GGCTAATTTT TTCAAGTTCA TTCCAACCAA TGATAGGCAT CACTTCTTGG ATAGGGATAA    9240

GGTTTTTATT ATTATCAATA ATATAATCAA GATAATGTTC AAATATACTT TCTAAGGCAG    9300

ACCAACCATT TGTTAAATCA GTTTTTGTTG TGATGTAGGC ATCAATCATA ATTAATTGCT    9360

GCTTATAACA GGCACTGAGT AATTGTTTTT TATTTTTAAA GTGATGATAA AAGGCACCTT    9420

TGGTCACCAA CGCTTTTCCC GAGATCCTCT GCGACACCGC CGCTCGTCTG CACGCGCCGC    9480

GGTCCGGACC GCCGCCCGAT CTCCATCCGC TACAGGAATG GTTCCAGCCG CTTTTCCGGT    9540

TGGCCGCTGA GCACGCGGCA CTTGCGCCCG CCGCAGCGT AGCGCGCCAA CTTCTGGCGG    9600

CGCCGCGCGA GGTGTGCCCG CTCCACGGCG ACCTGCACCA CGAGAACGTG CTCGACTTCG    9660
```

```
GCGACCGCGG CTGGCTGGCC ATCGACCCGC ACGGACTGCT CGGCGAGCGC ACCTTCGACT    9720

ATGCCAACAT CTTCACGAAT CCCGATCTCA GCGACCCCGG TCGCCCGCTT GCGATCCTGC    9780

CGGGCAGGCT GGAGGCTCGA CTCAGCATTG TGGTCGCGAC GACCGGGTTT GAGCCCGAAC    9840

GGCTTCTTCG CTGGATCATT GCATGGACGG GCTTGTCGGC AGCCTGGTTC ATCGGCGACG    9900

GCGACGGCGA GGGCGAGGGC GCTGCGATTG ATCTGGCCGT AAACGCCATG GCACGCCGGT    9960

TGCTTGACTA GCGCGGTCAC CGATCTCACC TGGTCGTCGA GCTAGGTCAG GCCGTGTCGG    10020

GCGTGATCCG CTGGAAGTCG TTGCGGGCCA CACCCGCCGC CTCGAAGCCC TGCACCAGGC    10080

CGGCATCGTG GTGTGCGTGG CCGAGGGACT ATGGAAGGTG CCGGACGATC TGCCCGAGCA    10140

GGGCCGCCGC TATGACGCCC AGCGTCTTGG TGGCGTGACG GTGGAGCTGA AATCGCACCT    10200

GCCCATCGAG CGGCAGGCCC GCGTGATCGG TGCCACCTGG CTTGACCAGC AGTTGATCGA    10260

CGGTGGCTCG GGCTTGGGCG ACCTGGGCTT TAGCAGTGAG GCCAAGTAGG CGATACAGCA    10320

GCGCGCGGAC TTCCTGGCCG AACAGGGACT GGCCGAGCGG CGCGGGCAGC GCGTGATCCT    10380

CACCGGAATC TGCTGGGCAG CAGCGGGCTC GGGAACTGGC GCAGGCCGCG AAGGACATTG    10440

CCGCCGATAC CGGCCTGGAG CATCGCCCCG TGGCCGACGG CCAGCGCGTT GCCGGCGTCT    10500

ACCGGCGCCC CGTCATGCTC GCCAGCGGGC GAAATGGGAT GCTTGATGAC GCCAAGGGGT    10560

CCAGCCTCGT GCGGTGGAAG CCCATCGAAC AGCGGCTTGG GGAGCAGCTC GCCGCGACGG    10620

TGCGCGGTGG CGGCGTGTCT TGGGAGATTG GACGACAGCG TGGGCCGGCC CCTGTCTCTT    10680

GATCAGATCT TGATCCCCTG CGCCATCAGA TCCTTGGCGG CAAGAAAGCC ATCCAGTTTA    10740

CTTTGCAGGG CTTCCCAACC TTCCCAGAGG GCGCCCCAGC TGGCAATTCC GGTTCGCTTG    10800

CTGTCCATAA AACCGCCCAG TCTAGCTATC GCCATGTAAG CCCACTGCAA GCTACCTGCT    10860

TTCTCTTTGC GCTTGCGTTT TCCCTTGTCC AGATAGCCCA GTAGCTGACA TTCATCCGGG    10920

GTCAGCACCG TTTCTGCGGA CTGGCTTTCT ACGTGTTCCG CTTCCTTTAG CAGCCCTTGC    10980

GCCCTGAGTG CTTGCGGCAG CGTGAAGCTT TCTCTGAGCT GTAACAGCCT GACCGCAACA    11040

AACGAGAGGA TCGAGACCAT CCGCTCCAGA TTATCCGGCT CCTCCATGCG TTGCCTCTCG    11100

GCTCCTGCTC CGGTTTTCCA TGCCTTATGG AACTCCTCGA TCCGCCAGCG ATGGGTATAA    11160

ATGTCGATGA CGCGCAAGGC TTGGGCTAGC GACTCGACCG GTTCGCCGGT CAGCAACAAC    11220

CATTTCAACG GGGTCTCACC CTTGGGCGGG TTAATCTCCT CGGCCAGCAC CGCGTTGAGC    11280

GTGATATTCC CCTGTTTTAG CGTGATGCGC CCACTGCGCA GGCTCAAGCT CGCCTTGCGG    11340

GCTGGTCGAT TTTTACGTTT ACCGCGTTTA TCCACCACGC CCTTTTGCGG AATGCTGATC    11400

TGATAGCCAC CCAACTCCGG TTGGTTCTTC AGATGGTCGA TCAGATACAA CCCAGACTCT    11460

ACGTCCTTGC GTGGGTGCTT GGAGCGCACC ACGAAGCGCT CGTTATGCGC CAGCCTGTCC    11520

TGCAGATAAG CATGAATATC GGCTTCGCGG TCACAGACCG CAATCACGTT GCTCATCATG    11580

CTGCCCATGC GTAACCGGCT AGTTGCGGCC GCTGCCAGCC ATTTGCCACT CTCCTTTTCA    11640

TCCGCATCGG CAGGGTCATC CGGGCGCATC CACCACTCCT GATGCAGTAA TCCTACGGTG    11700

CGGAATGTGG TGGCCTCGAG CAAGAGAACG GAGTGAACCC ACCATCCGCG GGATTTATCC    11760

TGAATAGAGC CCAGCTTGCC AAGCTCTTCG GCGACCTGGT GGCGATAACT CAAAGAGGTG    11820

GTGTCCTCAA TGGCCAGCAG TTCGGGAAAC TCCTGAGCCA ACTTGACTGT TTGCATGGCG    11880

CCAGCCTTTC TGATCGCCTC GGCAGAAACG TTGGGATTGC GGATAAATCG GTAAGCGCCT    11940

TCCTGCATGG CTTCACTACC CTCTGATGAG ATGGTTATTG ATTTACCAGA ATATTTTGCC    12000

AATTGGGCGG CGACGTTAAC CAAGCGGGCA GTACGGCGAG GATCACCCAG CGCCGCCGAA    12060
```

```
GAGAACACAG ATTTAGCCCA GTCGGCCGCA CGATGAAGAG CAGAAGTTAT CATGAACGTT    12120

ACCATGTTAG GAGGTCACAT GGAAGATCAG ATCCTGGAAA ACGGGAAAGG TTCCGTTCGA    12180

ATTGCATGCG GATCCGGGAT CAAGATCTGA TCAAGAGACA GGTACCAATT GTTGAAGACG    12240

AAAGGGCCTC GTGATACGCC TATTTTTATA GGTTAATGTC ATGATAATAA TGGTTTCTTA    12300

GACGTCAGGT GGCACTTTTC GGGGAAATGT GCGCGGAACC CCTATTTGTT TATTTTTCTA    12360

AATACATTCA AATATGTATC CGCTCATGAG ACAATAACCC TGATAAATGC TTCAATAATA    12420

TTGAAAAAGG AAGAGTATGA GTATTCAACA TTTCCGTGTC GCCCTTATTC CCTTTTTTGC    12480

GGCATTTTGC CTTCCTGTTT TTGCTCACCC AGAAACGCTG GTGAAAGTAA AAGATGCTGA    12540

AGATCAGTTG GGTGCACGAG TGGGTTACAT CGAACTGGAT CTCAACAGCG GTAAGATCCT    12600

TGAGAGTTTT CGCCCCGAAG AACGTTTTCC AATGATGAGC ACTTTTAAAG TTCTGCTATG    12660

TGGCGCGGTA TTATCCCGTG TTGACGCCGG GCAAGAGCAA CTCGGTCGCC GCATACACTA    12720

TTCTCAGAAT GACTTGGTTG AGTACTTGGC AAACTGATCT AAATGTTTAG CCCAGTCATC    12780

ATACTTCACC GATGCCAACG CATTAAAAAT AGCATCACGA TCGGCTTTGC TGAATTTCTT    12840

ATTTAAAACA TCCTTGTATT TTTCAAAAGC AGCGAGAGCT TCATTCACAT TGCCGATTTT    12900

CTTACCTTTA GACTTATCAG CAAGTTCCTG TGCCATTTTC GAATATTTTT CACCATATTT    12960

TTCAGTCAGC GTTTGATAAA AGCTAACTGT TGCATCAACA GCATCCTTAA TCTGTGAATT    13020

AAGGAGATTA TTCTGTGCTT TTTTCAAATT TTCTTCAGCT TCATGAACAC GAGCGATACC    13080

GGCATTACGA TTATTACTGA CCTGAGAAAT AGCCTTCTGG ATCTGAGTTA TATCAGCATT    13140

TATCCGGTTA ATACGTGTTT CTGATGCTGT TACCTGTTTT TGTTTTTCTT CTCTAATCTT    13200

ACCGGCCCCA ACCCGTCGTC TGGTTGCTTC AAAAAAAGGA CGGTTCTGAA GCGGATCATT    13260

GGCTCTTGGT GATAGTTTTT TGACCAGCTC ATCCAGTTCT TTATATTTAG CGGATGCCTG    13320

AGCCAGTTCA TTTCGTTTTC CAGCGAGCGT TTTCATTTCT GCATCACGGG CATGGATACT    13380

GGAGCTTAAA CGAGAATTGA GAGTCTTAAT CTCTCCATCC ATTTTCACCA CTTCAGATTG    13440

TGCAGCAGAA AGTTTTTTTT GGGCGATCTC AACAGCTTTA GCTTCTTCAC TCAATGCAGC    13500

CAGTCGTTTC TCTTCAGCTT CAGCCAGTTT CAACTGGCGT TCTGTTTCAG CCTTCTCCCG    13560

TTCAATCTCT TTACGTCGTT GTTCTGCTTC CTGAAAAGCC TTTTCTGCTG CTTCCGCTTC    13620

TTTACGGGCT TTTTCTTCTG CTTTCGCAAG GCGCAAACGC TCTGCTTCCG CCTGCATAGC    13680

TGCATTATTA GCATGAGCAA GCTCTGTTGC TGAAGGCGTA CGTGAGGCAT TGTGACGAAG    13740

AGCCTCATTC ACGATATCCT TCAGGCGCTG AGTCAGCGCA TCCCTGTTTG CCTTTGCTTT    13800

CGCCTGTGCT TCCGCTGCAG CTTTTGCCCG GGCAGCCTGC TCTGCCTGTG TTTTCTTTAA    13860

TTGAGCAGTA GACCATTTAG CAGTTGCATG AATAGCTGCA GAACTTTCAC TTTTACTGCC    13920

TCCTTTTCCA CCTCCGCCGC CAGAGCCACT CCCGTCAGGA GTACCATTCA AAAGAGTAAT    13980

AATTACCTGT CCCTTATCAT CATAAGGAAC ACCATCTTTA TAGTACGCTA CCGCGGTTTC    14040

CATTATAAAA TCCTCTTTGA CTTTTAAAAC AATAAGTTAA AAATAAATAC TGTACATATA    14100

ACCACTGGTT TTATATACAG CATAAAAGCT ACGCCGCTGC ATTTTCCCTG TCAAGACTGT    14160

GGACTTCCAT TTTTGTGAAA CGATCAAAA AAACAGTCTT TCACACCACG CGCTATTCTC    14220

GCCCGATGCC ACAAAAACCA GCACAAACAT TACCGTTCTC AGACCTCATT ATGTTTTACT    14280

GAAACTATGA GATGAGACAT CTATGGGACA CTGTCACTTT ATGGCATGGC ACACACTCCG    14340

GGACGCACTA AAAATGACAG GCAGATCGCG TTCACAGTTT TACCGTGATA TGCGCGGAGG    14400

CCTTGTCAGT TACCGTACCG GCAGGGACGG ACGACGGGAG TTTGAAACCA GTGAACTGAT    14460
```

```
CCGGGCATAC GGCGAATTAA AGCAGAATGA GACACCAGAA AGGCACAGTG AGGGACATGC    14520

AGAAAATCCA CATGATCAGC AGACAGAACG CATTCTCCGG GAACTGAATG AGCTGAAACA    14580

ATGCCTGACG CTGATGCTTG AGGATAAACA GGCACAGGAT ATGGATCGCA GACGCCAGGA    14640

AGCAGAACGG GAACAGCTAC AAAATGAGAT AGCCCAGCTC AGGCAGGCAC TGGAACTGGA    14700

AAAGAAACGG GGATTCTGGT CCAGGTTGTT CGGTCGCTGA ACGCTGTCAG AGACTGATGA    14760

TAAAATAGTC TTCGGATAAT AACTCACCGA GAATAAATAC TTTAAGGTAG GGAGACACTC    14820

ATGAGACGTA CCGGAAACAA ACTTTGTCTT ATCGCCATGA TAACAGCAAC AGTAGCTCTC    14880

ACAGCCTGTA CCCCAAAGGG CAGCGTGGAA CAACATACCC GGCATTACGT ATATGCTTCT    14940

GATGACGGTT TTGATCCCAA CTTTTCCACC CAAAAAGCCG ACACAACACG AATGATGGTG    15000

CCTTTTTTTC GGCAGTTCTG GGATATGGGA GCTAAAGACA AAGCGACAGG AAAATCACGG    15060

AGTGATGTGC AACAACGCAT TCAGCAGTTT CACAGCCAAG AATTTTTAAA CTCACTCCGG    15120

GGCACAACTC AATTTGCGGG TACTGATTAC CGCAGCAAAG ACCTTACCCC GAAAAAATCC    15180

AGGCTGCTGG CTGACACGAT TTCTGCGGTT TATCTCGATG GCTACGAGGG CAGACAGTAA    15240

GTGGATTTAC CATAATCCCT TAATTGTACG CACCGCTAAA ACGCGTTCAG CGCGATCACG    15300

GCAGCAGACA GGTAAAAATG GCAACAAACC ACCCTAAAAA CTGCGCGATC GCGCCTGATA    15360

AATTTTAACC GTATGAATAC CTATGCAACC AGAGGGTACA GGCCACATTA CCCCCACTTA    15420

ATCCACTGAA GCTGCCATTT TTCATGGTTT CACCATCCCA GCGAAGGGCC ATCCAGCGTG    15480

CGTTCCTGTA TTTCCGGCTG ACGCTCCCGT TCTAGGGATA ACACATGTTC GCGCTCCTGT    15540

ATCAGCCGTT CCTCTCTTAT CTCCAGTTCT CGCTGTATAA CTGGCTCAAG CGTTCTGTCT    15600

GCTCGCTCAA GTGTTGCACC TGCTGACTCA ACTGCATGAC CCGCTCGTTC AGCATCGCGT    15660

TGTCCCGTTG CGTAAGCGAA AACATCTTCT GCAATTCCAC GAAGGCGCTC TCCCATTCGC    15720

TCAGCCGCTG CATATAGTCC TGTTGCAGCT GCTCTAAGGC GTTCAGCAAA TGTGTTTCCA    15780

GCTCTGTCAC TCTGTGTCAC TCCTTCAGAT GTACCCACTC TTTCCCCTGA AAGGGAATCA    15840

CCTCCGCTGA TTTCCCGTAC GGAAGGACAA GGAATTTCCT GTTCCCGTCC TGCACAAACT    15900

CCACGCCCCA TGTCTTCGCG TTCAGTTTCT GCAATGTCTC TTCCTGCTTC CTGATTTCTT    15960

CCAGGTTCGC CTGTATCCTC CCTCCAAGAT ACCAGAGCGT CCCGCCACTC GCGGTAAACA    16020

GGAGAAAGAC TATCCCCAGT AACATCATGC CCGTATTCCC TGCCAGCTTT AACACGTCCC    16080

TCCTGTGCTG CATCATCGCC TCTTTCACCC CTTCCCGGTG TTTTTCCAGC GATTCCTCTG    16140

TCGAGGCTGT GAACAGGGCT ATAGCGTCTC TGATTTTCGT CTCGTTTGAT GTCACAGCCT    16200

CGCTTACAGA TTCGCCGAGC CTCCTGAACT CGTTGTTCAG CATTTTCTCT GTAGATTCGG    16260

CTCTCTCTTT CAGCTTTTTC TCGAACTCCG CGCCCGTCTG CAAAAGATTG CTCATAAAAT    16320

GCTCCTTTCA GCCTGATATT CTTCCCGCCG TTCGGATCTG CAATGCTGAT ACTGCTTCGC    16380

GTCACCCTGA CCACTTCCAG CCCCGCCTCA GTGAGCGCCT GAATCACATC CTGACGGCCT    16440

TTTATCTCTC CGGCATGGTA AAGTGCATCT ATACCTCGCG TGACGCCCTC AGCAAGCGCC    16500

TGTTTCGTTT CAGGCAGGTT ATCAGGGAGT GTCAGCGTCC TGCGGTTCTC CGGGGCGTTC    16560

GGGTCATGCA GCCCGTAATG GTGATTTAAC AGCGTCTGCC AAGCATCAAT TCTAGGCCTG    16620

TCTGCGCGGT CGTAGTACGG CTGGAGGCGT TTTCCGGTCT GTAGCTCCAT GTTCGGAATG    16680

ACAAAATTCA GCTCAAGCCG TCCCTTGTCC TGGTGCTCCA CCCACAGGAT GCTGTACTGA    16740

TTTTTTTCGA GACCGGGCAT CAGTACACGC TCAAAGCTCG CCATCACTTT TTCACGTCCT    16800

CCCGGCGGCA GCTCCTTCTC CGCGAACGAC AGAACACCGG ACGTGTATTT CTTCGCAAAT    16860
```

```
GGCGTGGCAT CGATGAGTTC CCGGACTTCT TCCGGTATAC CCTGAAGCAC CGTTGCGCCT    16920

TCGCGGTTAC GCTCCCTCCC CAGCAGGTAA TCAACCGGAC CACTGCCACC ACCTTTTCCC    16980

CTGGCATGAA ATTTAACTAT CATCCCGCGC CCCCTGTTCC CTGACAGCCA GACGCAGCCG    17040

GCGCAGCTCA TCCCCGATGG CCATCAGTGC GGCCACCACC TGAACCCGGT CACCGGAAGA    17100

CCACTGCCCG CTGTTCACCT TACGGGCTGT CTGATTCAGG TTATTTCCGA TGGCGGCCAG    17160

CTGACGCAGT AACGGCGGTG CCAGTGTCGG CAGTTTTCCG GAACGGGCAA CCGGCTCCCC    17220

CAGGCAGACC CGCCGCATCC ATACCGCCAG TTGTTTACCC TCACAGCGTT CAAGTAACCG    17280

GGCATGTTCA TCATCAGTAA CCCGTATTGT GAGCATCCTC TCGCGTTTCA TCGGTATCAT    17340

TACCCCATGA ACAGAAATCC CCCTTACACG GAGGCATCAG TGACTAAACA GGAAAAAACC    17400

GCCCTTAACA TGGCCCGCTT TATCAGAAGC CAGACATTAA CGCTGCTGGA GAAGCTCAAC    17460

GAACTGGACG CAGATGAACA GGCCGATATT TGTGAATCGC TTCACGACCA CGCCGATGAG    17520

CTTTACCGCA GCTGCCTCGC ACGTTTCGGG GATGACGGTG AAAACCTCTG ACACATGCAG    17580

CTCCCGGAGA CGGTCACAGC TTGTCTGTGA GCGGATGCCG GGAGCTGACA AGCCCGTCAG    17640

GGCGCGTCAG CAGGTTTTAG CGGGTGTCGG GGCGCAGCCC TGACCCAGTC ACGTAGCGAT    17700

AGCGGAGTGT ATACTGGCTT AACCATGCGG CATCAGTGCG GATTGTATGA AAAGTACGCC    17760

ATGCCGGGTG TGAAATGCCG CACAGATGCG TAAGGAGAAA ATGCACGTCC AGGCGCTTTT    17820

CCGCTTCCTC GCTCACTGAC TCGCTACGCT CGGTCGTTCG ACTGCGGCGA GCGGTACTGA    17880

CTCACACAAA AACGGTAACA CAGTTATCCA CAGAATCAGG GGATAAGGCC GGAAAGAACA    17940

TGTGAGCAAA AGACCAGGAA CAGGAAGAAG GCCACGTAGC AGGCGTTTTT CCATAGGCTC    18000

CGCCCCCCTG ACGAGCATCA CAAAAATAGA CGCTCAAGTC AGAGGTGGCG AAACCCGACA    18060

GGACTATAAA GCTACCAGGC GTTTCCCCCT GGAAGCTCCC TCGTGCGCTC TCCTGTTCCG    18120

ACCCTGCCGC TTACCGGATA CCTGTCCGCC TTTCTCCCTT CGGGAAGCGT GGCGCTTTCT    18180

CATAGCTCAC GCTGTTGGTA TCTCAGTTCG GTGTAGGTCG TTCGCTCCAA GCTGGGCTGT    18240

GTGCACGAAC CCCCCGTTCA GCCCGACCGC TGCGCCTTAT CCGGTAACTA TCGTCTTGAG    18300

TCCAACCCGG TAAGGCACGC CTTAACGCCA CTGGCAGCAG CCACTGGTAA CCGGATTAGC    18360

AGAGCGATGA TGGCACAAAC GGTGCTACAG AGTTCTTGAA GTAGTGGCCC GACTACGGCT    18420

ACACTAGAAG GACAGTATTT GGTATCTGCG CTCTGCTGAA GCCAGTTACC TTCGGAAAAA    18480

GAGTTGGTAG CTCTTGATCC GGCAAACAAA CCACCGTTGG TAGCGGTGGT TTTTTTGTTT    18540

GCAAGCAGCA GATTACGCGC AGAAAAAAAG GATCTCAAGA AGATCCTTTA ATCTTTTCTA    18600

CTGAACCGCG ATCCCCGTCA GTTTAGAAGA GGAGGATGGT GCGATGGTCC CTCCCTGAAC    18660

ATCAGGTATA TAGTTAGCCT GACATCCAAC AAGGAGGTTT ATCGCGAATA TCCCACAAA    18720

AAATCTTTTC CTCATAACTC GATCCTTATA AAATGAAAAG AATATATGGC GAGGTTTAAT    18780

TTATGAGCTT AAGATACTAC ATAAAAAATA TTTTATTTGG CCTGTACTGC ACACTTATAT    18840

ATATATACCT TATAACAAAA AACAGCGAAG GGTATTATTT CCTTGTGTCA GATAAGATGC    18900

TATATGCAAT AGTGATAAGC ACTATTCTAT GTCCATATTC AAAATATGCT ATTGAATACA    18960

TAGCTTTTAA CTTCATAAAG AAAGATTTTT TCGAAAGAAG AAAAAACCTA AATAACGCCC    19020

CCGTAGCAAA ATTAAACCTA TTTATGCTAT ATAATCTACT TTGTTTGGTC CTAGCAATCC    19080

CATTTGGATT GCTAGGACTT TTTATATCAA TAAAGAATAA TTAAATCCCT AACACCTCAT    19140

TTATAGTATT AAGTTTATTC TTATCAATAT AGGAGCATAG AA                       19182

(2) INFORMATION FOR SEQ ID NO:12:
```

(i) SEQUENCE CHARACTERISTICS:
        (A) LENGTH: 3418 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Plasmid pRZ7075"

(xi) SEQUENCE DESCRIPTION: SEQ ID NO:12:

```
AATTCGAGCT CGGTACCCGG GGATCCTCTA GAGTCGACCT GCAGGCATGC TCACTCACTC      60

AAGATGTGTA TAAGAGACAG TCGACCTGCA GGGGGGGGGG GGAAAGCCAC GTTGTGTCTC     120

AAAATCTCTG ATGTTACATT GCACAAGATA AAAATATATC ATCATGAACA ATAAAACTGT     180

CTGCTTACAT AAACAGTAAT ACAAGGGGTG TTATGAGCCA TATTCAACGG GAAACGTCTT     240

GCTCGAGGCC GCGATTAAAT TCCAACATGG ATGCTGATTT ATATGGGTAT AAATGGGCTC     300

GCGATAATGT CGGGCAATCA GGTGCGACAA TCTATCGATT GTATGGGAAG CCCGATGCGC     360

CAGAGTTGTT TCTGAAACAT GGCAAAGGTA GCGTTGCCAA TGATGTTACA GATGAGATGG     420

TCAGACTAAA CTGGCTGACG GAATTTATGC CTCTTCCGAC CATCAAGCAT TTTATCCGTA     480

CTCCTGATGA TGCATGGTTA CTCACCACTG CGATCCCCGG GAAAACAGCA TTCCAGGTAT     540

TAGAAGAATA TCCTGATTCA GGTGAAAATA TTGTTGATGC GCTGGCAGTG TTCCTGCGCC     600

GGTTGCATTC GATTCCTGTT TGTAATTGTC CTTTTAACAG CGATCGCGTA TTTCGTCTCG     660

CTCAGGCGCA ATCACGAATG AATAACGGTT TGGTTGATGC GAGTGATTTT GATGACGAGC     720

GTAATGGCTG GCCTGTTGAA CAAGTCTGGA AAGAAATGCA TAAGCTTTTG CCATTCTCAC     780

CGGATTCAGT CGTCACTCAT GGTGATTTCT CACTTGATAA CCTTATTTTT GACGAGGGGA     840

AATTAATAGG TTGTATTGAT GTTGGACGAG TCGGAATCGC AGACCGATAC CAGGATCTTG     900

CCATCCTATG GAACTGCCTC GGTGAGTTTT CTCCTTCATT ACAGAAACGG CTTTTTCAAA     960

AATATGGTAT TGATAATCCT GATATGAATA AATTGCAGTT TCATTTGATG CTCGATGAGT    1020

TTTTCTAATC AGAATTGGTT AATTGGTTGT AACACTGGCA GAGCATTACG CTGACTTGAC    1080

GGGACGGCGG CTTTGTTGAA TAAATCGAAC TTTTGCTGAG TTGAAGGATC AGATCACGCA    1140

TCTTCCCGAC AACGCAGACC GTTCCGTGGC AAAGCAAAAG TTCAAAATCA CCAACTGGTC    1200

CACCTACAAC AAAGCTCTCA TCAACCGTGG CTCCCTCACT TTCTGGCTGG ATGATGGGGC    1260

GATTCAGGCC TGGTATGAGT CAGCAACACC TTCTTCACGA GGCAGACCTC AGCGCCCCCC    1320

CCCCCCTGCA GGTCGACTGT CTCTTATACA CATCTTGAGT GAGTGAGCAT GCCAAGCTTT    1380

AATGCGGTAG TTTATCACAG TTAAATTGCT AACGCAGTCA GGCACCGTGT ATGAAATCTA    1440

ACAATGCGCT CATCGTCATC CTCGGCACCG TCACCCTGGA TGCTGTAGGC ATAGGCTTGG    1500

TTATGCCGGT ACTGCCGGGC CTCTTGCGGG ATCATGTGAG CAAAAGGCCA GCAAAAGGCC    1560

AGGAACCGTA AAAAGGCCGC GTTGCTGGCG TTTTTCCATA GGCTCCGCCC CCCTGACGAG    1620

CATCACAAAA ATCGACGCTC AAGTCAGAGG TGGCGAAACC CGACAGGACT ATAAAGATAC    1680

CAGGCGTTTC CCCCTGGAAG CTCCCTCGTG CGCTCTCCTG TTCCGACCCT GCCGCTTACC    1740

GGATACCTGT CCGCCTTTCT CCCTTCGGGA AGCGTGGCGC TTTCTCATAG CTCACGCTGT    1800

AGGTATCTCA GTTCGGTGTA GGTCGTTCGC TCCAAGCTGG GCTGTGTGCA CGAACCCCCC    1860

GTTCAGCCCG ACCGCTGCGC CTTATCCGGT AACTATCGTC TTGAGTCCAA CCCGGTAAGA    1920

CACGACTTAT CGCCACTGGC AGCAGCCACT GGTAACAGGA TTAGCAGAGC GAGGTATGTA    1980

GGCGGTGCTA CAGAGTTCTT GAAGTGGTGG CCTAACTACG GCTACACTAG AAGGACAGTA    2040
```

-continued

```
TTTGGTATCT GCGCTCTGCT GAAGCCAGTT ACCTTCGGAA AAAGAGTTGG TAGCTCTTGA    2100

TCCGGCAAAC AAACCACCGC TGGTAGCGGT GGTTTTTTTG TTTGCAAGCA GCAGATTACG    2160

CGCAGAAAAA AAGGATCTCA AGAAGATCCT TTGATCTTTT CTACGGGGTC TGACGCTCAG    2220

TGGAACGAAA ACTCACGTTA AGGGATTTTG GTCATGAGAT TATCAAAAAG GATCTTCACC    2280

TAGATCCTTT TAAATTAAAA ATGAAGTTTT AAATCAATCT AAAGTATATA TGAGTAAACT    2340

TGGTCTGACA GTTACCAATG CTTAATCAGT GAGGCACCTA TCTCAGCGAT CTGTCTATTT    2400

CGTTCATCCA TAGTTGCCTG ACTCCCCGTC GTGTAGATAA CTACGATACG GGAGGGCTTA    2460

CCATCTGGCC CCAGTGCTGC AATGATACCG CGAGACCCAC GCTCACCGGC TCCAGATTTA    2520

TCAGCAATAA ACCAGCCAGC CGGAAGGGCC GAGCGCAGAA GTGGTCCTGC AACTTTATCC    2580

GCCTCCATCC AGTCTATTAA TTGTTGCCGG GAAGCTAGAG TAAGTAGTTC GCCAGTTAAT    2640

AGTTTGCGCA ACGTTGTTGC CATTGCTGCA GGCATCGTGG TGTCACGCTC GTCGTTTGGT    2700

ATGGCTTCAT TCAGCTCCGG TTCCCAACGA TCAAGGCGAG TTACATGATC CCCCATGTTG    2760

TGCAAAAAAG CGGTTAGCTC CTTCGGTCCT CCGATCGTTG TCAGAAGTAA GTTGGCCGCA    2820

GTGTTATCAC TCATGGTTAT GGCAGCACTG CATAATTCTC TTACTGTCAT GCCATCCGTA    2880

AGATGCTTTT CTGTGACTGG TGAGTACTCA ACCAAGTCAT TCTGAGAATA GTGTATGCGG    2940

CGACCGAGTT GCTCTTGCCC GGCGTCAACA CGGGATAATA CCGCGCCACA TAGCAGAACT    3000

TTAAAAGTGC TCATCATTGG AAAACGTTCT TCGGGGCGAA AACTCTCAAG GATCTTACCG    3060

CTGTTGAGAT CCAGTTCGAT GTAACCCACT CGTGCACCCA ACTGATCTTC AGCATCTTTT    3120

ACTTTCACCA GCGTTTCTGG GTGAGCAAAA ACAGGAAGGC AAAATGCCGC AAAAAAGGGA    3180

ATAAGGGCGA CACGGAAATG TTGAATACTC ATACTCTTCC TTTTTCAATA TTATTGAAGC    3240

ATTTATCAGG GTTATTGTCT CATGAGCGGA TACATATTTG AATGTATTTA GAAAAATAAA    3300

CAAATAGGGG TTCCGCGCAC ATTTCCCCGA AAAGTGCCAC CTGACGTCTA AGAAACCATT    3360

ATTATCATGA CATTAACCTA TAAAAATAGG CGTATCACGA GGCCCTTTCG TCTTCAAG     3418
```

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:13:

```
CGCAAGAGGC CCGGCAGTAC                                                 20
```

SYSTEM FOR IN VITRO TRANSPOSITION

CROSS-REFERENCE TO RELATED APPLICATION

This patent application is a continuation-in-part of patent application Ser. No. 08/850,880, entitled "System for In Vitro Transposition," filed May 2, 1997, which was a continuation-in-part of patent application Ser. No. 08/814,877, entitled "System for In Vitro Transposition," filed Mar. 11, 1997, and accorded a filing date of Sep. 9, 1996.

STATEMENT REGARDING FEDERALLY SPONSORED RESEARCH OR DEVELOPMENT

This invention was made with United States government support awarded by the following agencies:

NIH, Grant No.: GM50692

NSF, Grant Nos: BIR-9424074; MCB-9419784

The United States has certain rights in this invention.

BACKGROUND OF THE INVENTION

The present invention relates generally to the field of transposable nucleic acid and, more particularly to production and use of a modified transposase enzyme in a system for introducing genetic changes to nucleic acid.

Transposable genetic elements are DNA sequences, found in a wide variety of prokaryotic and eukaryotic organisms, that can move or transpose from one position to another position in a genome. In vivo, intra-chromosomal transpositions as well as transpositions between chromosomal and non-chromosomal genetic material are known. In several systems, transposition is known to be under the control of a transposase enzyme that is typically encoded by the transposable element. The genetic structures and transposition mechanisms of various transposable elements are summarized, for example, in "Transposable Genetic Elements" in "The Encyclopedia of Molecular Biology," Kendrew and Lawrence, Eds., Blackwell Science, Ltd., Oxford (1994), incorporated herein by reference.

In vitro transposition systems that utilize the particular transposable elements of bacteriophage Mu and bacterial transposon Tn10 have been described, by the research groups of Kiyoshi Mizuuchi and Nancy Kleckner, respectively.

The bacteriophage Mu system was first described by Mizuuchi, K., "In Vitro Transposition of Bacteria Phage Mu: A Biochemical Approach to a Novel Replication Reaction," *Cell*:785–794 (1983) and Craigie, R. et al., "A Defined System for the DNA Strand-Transfer Reaction at the Initiation of Bacteriophage Mu Transposition: Protein and DNA Substrate Requirements," *P.N.A.S. U.S.A.* 82:7570–7574 (1985). The DNA donor substrate (mini-Mu) for Mu in vitro reaction normally requires six Mu transposase binding sites (three of about 30 bp at each end) and an enhancer sequence located about 1 kb from the left end. The donor plasmid must be supercoiled. Proteins required are Mu-encoded A and B proteins and host-encoded HU and IHF proteins. Lavoie, B. D, and G. Chaconas, "Transposition of phage Mu DNA," *Curr. Topics Microbiol. Immunol.* 204:83–99 (1995). The Mu-based system is disfavored for in vitro transposition system applications because the Mu termini are complex and sophisticated and because transposition requires additional proteins above and beyond the transposase.

The Tn10 system was described by Morisato, D. and N. Kleckner, "Tn10 Transposition and Circle Formation in vitro," *Cell* 51:101–111 (1987) and by Benjamin, H. W. and N. Kleckner, "Excision Of Tn10 from the Donor Site During Transposition Occurs By Flush Double-Strand Cleavages at the Transposon Termini," *P.N.A.S. U.S.A.* 89:4648–4652 (1992). The Tn10 system involves the a supercoiled circular DNA molecule carrying the transposable element (or a linear DNA molecule plus *E. coli* IHF protein). The transposable element is defined by complex 42 bp terminal sequences with IHF binding site adjacent to the inverted repeat. In fact, even longer (81 bp) ends of Tn10 were used in reported experiments. Sakai, J. et al., "Identification and Characterization of Pre-Cleavage Synaptic Complex that is an Early Intermediate in Tn10 transposition," *E.M.B.O. J.* 14:4374–4383 (1995). In the Tn10 system, chemical treatment of the transposase protein is essential to support active transposition. In addition, the termini of the Tn10 element limit its utility in a generalized in vitro transposition system.

Both the Mu- and Tn10-based in vitro transposition systems are further limited in that they are active only on covalently closed circular, supercoiled DNA targets. What is desired is a more broadly applicable in vitro transposition system that utilizes shorter, more well defined termini and which is active on target DNA of any structure (linear, relaxed circular, and supercoiled circular DNA).

BRIEF SUMMARY OF THE INVENTION

The present invention is summarized in that an in vitro transposition system comprises a preparation of a suitably modified transposase of bacterial transposon Tn5, a donor DNA molecule that includes a transposable element, a target DNA molecule into which the transposable element can transpose, all provided in a suitable reaction buffer.

The transposable element of the donor DNA molecule is characterized as a transposable DNA sequence of interest, the DNA sequence of interest being flanked at its 5'- and 3'-ends by short repeat sequences that are acted upon in trans by Tn5 transposase.

The invention is further summarized in that the suitably modified transposase enzyme comprises two classes of differences from wild type Tn5 transposase, where each class has a separate measurable effect upon the overall transposition activity of the enzyme and where a greater effect is observed when both modifications are present. The suitably modified enzyme both (1) binds to the repeat sequences of the donor DNA with greater avidity than wild type Tn5 transposase ("class (1) mutation") and (2) is less likely than the wild type protein to assume an inactive multimeric form ("class (2) mutation"). A suitably modified Tn5 transposase of the present invention that contains both class (1) and class (2) modifications induces at least about 100-fold (±10%) more transposition than the wild type enzyme, when tested in combination in an in vivo conjugation assay as described by Weinreich, M. D., "Evidence that the cis Preference of the Tn5 Transposase is Caused by Nonproductive Multimerization," *Genes and Development* 8:2363–2374 (1994), incorporated herein by reference. Under optimal conditions, transposition using the modified transposase may be higher. A modified transposase containing only a class (1) mutation binds to the repeat sequences with sufficiently greater avidity than the wild type Tn5 transposase that such a Tn5 transposase induces about 5- to 50-fold more transposition than the wild type enzyme, when measured in vivo. A modified transposase containing only a class (2) mutation is sufficiently less likely than the wild type Tn5 transposase to assume the multimeric form that such a Tn5 transposase also induces about 5- to 50-fold more transposition than the wild type enzyme, when measured in vivo.

In another aspect, the invention is summarized in that a method for transposing the transposable element from the donor DNA into the target DNA in vitro includes the steps of mixing together the suitably modified Tn5 transposase protein, the donor DNA, and the target DNA in a suitable reaction buffer, allowing the enzyme to bind to the flanking repeat sequences of the donor DNA at a temperature greater than 0° C., but no higher than about 28° C., and then raising the temperature to physiological temperature (about 37° C.) whereupon cleavage and strand transfer can occur.

In yet another aspect, the invention is a simple and efficient method for intramolecular in vitro transposition to generate desirable inversions and nested deletions in a nucleic acid insert provided in the genetic construct. The inversion and nested deletion products can be generated in a one-step, one-enzyme in vitro reaction.

The products generated by the in vitro transposition method can be used as templates in standard nucleic acid sequencing reactions to reveal the nucleic acid sequences of the insert. Overlapping nucleic acid sequences located progressively further along the insert can be obtained in high-throughput sequence analysis of nested deletion products. Inversion products, in which a random portion of the insert is inverted relative to its original orientation, can be used as templates for obtaining nucleotide sequence data from both DNA strands.

The products can also be transcribed and translated in vivo or in vitro to produce polypeptides. If nested deletion products are used, polypeptides having amino- or carboxy-end truncations of increasing length can be produced. Such truncated polypeptides can be used for analyzing the relationship between protein structure and function.

In a related aspect, the invention is a genetic construct for use in the intramolecular in vitro transposition system.

It is an object of the present invention to provide a useful in vitro transposition system having few structural requirements and high efficiency.

It is another object of the present invention to provide a method that can be broadly applied in various ways, such as to create absolute defective mutants, to provide selective markers to target DNA, to provide portable regions of homology to a target DNA, to facilitate insertion of specialized DNA sequences into target DNA, to provide primer binding sites or tags for DNA sequencing, to facilitate production of genetic fusions for gene expression studies and protein domain mapping, as well as to bring together other desired combinations of DNA sequences (combinatorial genetics).

It is a feature of the present invention that the modified transposase enzyme binds more tightly to DNA than does wild type Tn5 transposase.

It is an advantage of the present invention that the modified transposase facilitates in vitro transposition reaction rates of at least about 100-fold higher than can be achieved using wild type transposase (as measured in vivo). It is noted that the wild-type Tn5 transposase shows no detectable in vitro activity in the system of the present invention. Thus, while it is difficult to calculate an upper limit to the increase in activity, it is clear that hundreds, if not thousands, of colonies are observed when the products of in vitro transposition are assayed in vivo.

It is another advantage of the present invention that in vitro transposition using this system can utilize donor DNA and target DNA that is circular or linear.

It is yet another advantage of the present invention that in vitro transposition using this system requires no outside high energy source and no other protein other than the modified transposase.

Other objects, features, and advantages of the present invention will become apparent upon consideration of the following detailed description.

DETAILED DESCRIPTION OF THE INVENTION

Figure 1:
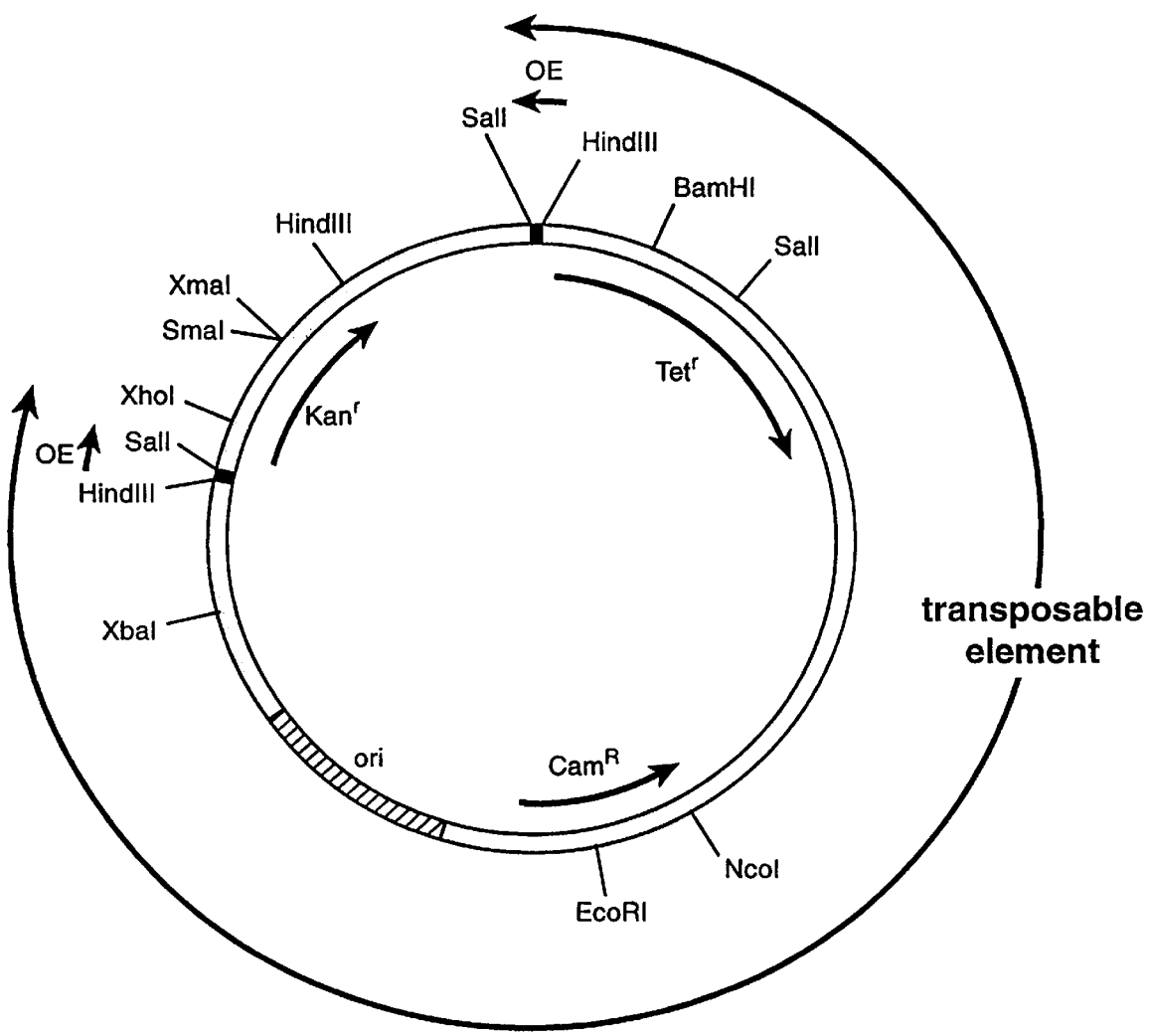
FIG. 1 depicts test plasmid pRZTL1, used herein to demonstrate transposition in vitro of a transposable element located between a pair of Tn5 outside end termini. Plasmid pRZTL1 is also shown and described in SEQ ID NO:3.

It will be appreciated that this technique provides a simple, in vitro system for introducing any transposable element from a donor DNA into a target DNA. It is generally accepted and understood that Tn5 transposition requires only a pair of OE termini, located to either side of the transposable element. These OE termini are generally thought to be 18 or 19 bases in length and are inverted repeats relative to one another. Johnson, R. C., and W. S. Reznikoff, *Nature* 304:280 (1983), incorporated herein by reference. The Tn5 inverted repeat sequences, which are referred to as "termini" even though they need not be at the termini of the donor DNA molecule, are well known and understood.

Apart from the need to flank the desired transposable element with standard Tn5 outside end ("OE") termini, few other requirements on either the donor DNA or the target DNA are envisioned. It is thought that Tn5 has few, if any, preferences for insertion sites, so it is possible to use the system to introduce desired sequences at random into target DNA. Therefore, it is believed that this method, employing the modified transposase described herein and a simple donor DNA, is broadly applicable to introduce changes into any target DNA, without regard to its nucleotide sequence. It will, thus, be applied to many problems of interest to those skilled in the art of molecular biology.

In the method, the modified transposase protein is combined in a suitable reaction buffer with the donor DNA and the target DNA. A suitable reaction buffer permits the transposition reaction to occur. A preferred, but not necessarily optimized, buffer contains spermidine to condense the DNA, glutamate, and magnesium, as well as a detergent, which is preferably 3-[(3-cholamidopropyl) dimethyl-ammonio]-1-propane sulfonate ("CHAPS"). The mixture can be incubated at a temperature greater than 0° C. and as high as about 28° C. to facilitate binding of the enzyme to the OE termini. Under the buffer conditions used by the inventors in the Examples, a pretreatment temperature of 30° C. was not adequate. A preferred temperature range is between 16° C. and 28° C. A most preferred pretreatment temperature is about 20° C. Under different buffer conditions, however, it may be possible to use other below-physiological temperatures for the binding step. After a short pretreatment period of time (which has not been optimized, but which may be as little as 30 minutes or as much as 2 hours, and is typically 1 hour), the reaction mixture is diluted with 2 volumes of a suitable reaction buffer and shifted to physiological conditions for several more hours (say 2–3 hours) to permit cleavage and strand transfer to occur. A temperature of 37° C., or thereabouts, is adequate. After about 3 hours, the rate of transposition decreases markedly. The reaction can be stopped by phenol-chloroform extraction and can then be desalted by ethanol precipitation.

When the DNA has been purified using conventional purification tools, it is possible to employ simpler reaction conditions in the in vitro transposition method. DNA of sufficiently high purity can be prepared by passing the DNA preparation through a resin of the type now commonly used in the molecular biology laboratory, such as the Qiagen resin of the Qiagen plasmid purification kit (Catalog No. 12162). When such higher quality DNA is employed, CHAPS can be omitted from the reaction buffer. When CHAPS is eliminated from the reaction buffer, the reactants need not be diluted in the manner described above. Also, the low temperature incubation step noted above can be eliminated in favor of a single incubation for cleavage and strand transfer at physiological conditions. A three hour incubation at 37° C. is sufficient.

Following the reaction and subsequent extraction steps, transposition can be assayed by introducing the nucleic acid reaction products into suitable bacterial host cells (e.g., *E. coli* K-12 DH5α cells (recA⁻); commercially available from Life Technologies (Gibco-BRL)) preferably by electroporation, described by Dower et al., *Nuc. Acids. Res.* 16:6127 (1988), and monitoring for evidence of transposition, as is described elsewhere herein.

Those persons skilled in the art will appreciate that apart from the changes noted herein, the transposition reaction can proceed under much the same conditions as would be found in an in vivo reaction. Yet, the modified transposase described herein so increases the level of transposition activity that it is now possible to carry out this reaction in vitro where this has not previously been possible. The rates of reaction are even greater when the modified transposase is coupled with an optimized buffer and temperature conditions noted herein.

In another aspect, the present invention is a preparation of a modified Tn5 transposase enzyme that differs from wild type Tn5 transposase in that it (1) binds to the repeat sequences of the donor DNA with greater avidity than wild type Tn5 transposase and (2) is less likely than the wild type protein to assume an inactive multimeric form. An enzyme having these requirements can be obtained from a bacterial host cell containing an expressible gene for the modified enzyme that is under the control of a promoter active in the host cell. Genetic material that encodes the modified Tn5 transposase can be introduced (e.g., by electroporation) into suitable bacterial host cells capable of supporting expression of the genetic material. Known methods for overproducing and preparing other Tn5 transposase mutants are suitably employed. For example, Weinreich, M. D., et al., supra, describes a suitable method for overproducing a Tn5 transposase. A second method for purifying Tn5 transposase was described in de la Cruz, N. B., et al., "Characterization of the Tn5 Transposase and Inhibitor Proteins: A Model for the Inhibition of Transposition," *J. Bact.* 175:6932–6938 (1993), also incorporated herein by reference. It is noted that induction can be carried out at temperatures below 37° C., which is the temperature used by de la Cruz, et al. Temperatures at least in the range of 33 to 37° C. are suitable. The inventors have determined that the method for preparing the modified transposase of the present invention is not critical to success of the method, as various preparation strategies have been used with equal success.

Alternatively, the protein can be chemically synthesized, in a manner known to the art, using the amino acid sequence attached hereto as SEQ ID NO:2 as a guide. It is also possible to prepare a genetic construct that encodes the modified protein (and associated transcription and translation signals) by using standard recombinant DNA methods familiar to molecular biologists. The genetic material useful for preparing such constructs can be obtained from existing Tn5 constructs, or can be prepared using known methods for introducing mutations into genetic material (e.g., random mutagenesis PCR or site-directed mutagenesis) or some combination of both methods. The genetic sequence that encodes the protein shown in SEQ ID NO:2 is set forth in SEQ ID NO:1.

The nucleic acid and amino acid sequence of wild type Tn5 transposase are known and published. N.C.B.I. Accession Number U00004 L19385, incorporated herein by reference.

In a preferred embodiment, the improved avidity of the modified transposase for the repeat sequences for OE termini (class (1) mutation) can be achieved by providing a lysine residue at amino acid 54, which is glutamic acid in wild type Tn5 transposase. The mutation strongly alters the preference of the transposase for OE termini, as opposed to inside end ("IE") termini. The higher binding of this mutation, known as EK54, to OE termini results in a transposition rate that is about 10-fold higher than is seen with wild type transposase. A similar change at position 54 to valine (mutant EV54) also results in somewhat increased binding/transposition for OE termini, as does a threonine-to-proline change at position 47 (mutant TP47; about 10-fold higher). It is believed that other, comparable transposase mutations (in one or more amino acids) that increase binding avidity for OE termini may also be obtained which would function as well or better in the in vitro assay described herein.

One of ordinary skill will also appreciate that changes to the nucleotide sequences of the short repeat sequences of the donor DNA may coordinate with other mutation(s) in or near the binding region of the transposase enzyme to achieve the same increased binding effect, and the resulting 5- to 50-fold increase in transposition rate. Thus, while the applicants have exemplified one case of a mutation that improves binding of the exemplified transposase, it will be understood that other mutations in the transposase, or in the short repeat sequences, or in both, will also yield transposases that fall within the scope and spirit of the present invention. A suitable method for determining the relative avidity for Tn5 OE termini has been published by Jilk, R. A., et al., "The Organization of the Outside end of Transposon Tn5,"*J. Bact.* 178:1671–79 (1996).

The transposase of the present invention is also less likely than the wild type protein to assume an inactive multimeric form. In the preferred embodiment, that class (2) mutation from wild type can be achieved by modifying amino acid 372 (leucine) of wild type Tn5 transposase to a proline (and, likewise by modifying the corresponding DNA to encode proline). This mutation, referred to as LP372, has previously been characterized as a mutation in the dimerization region of the transposase. Weinreich, et al., supra. It was noted by Weinreich et al. that this mutation at position 372 maps to a region shown previously to be critical for interaction with an inhibitor of Tn5 transposition. The inhibitor is a protein encoded by the same gene that encodes the transposase, but which is truncated at the N-terminal end of the protein, relative to the transposase. The approach of Weinreich et al. for determining the extent to which multimers are formed is suitable for determining whether a mutation falls within the scope of this element.

It is thought that when wild type Tn5 transposase multimerizes, its activity in trans is reduced. Presumably, a mutation in the dimerization region reduces or prevents multimerization, thereby reducing inhibitory activity and leading to levels of transposition 5- to 50-fold higher than are seen with the wild type transposase. The LP372 mutation achieves about 10-fold higher transposition levels than wild type. Likewise, other mutations (including mutations at a one or more amino acid) that reduce the ability of the transposase to multimerize would also function in the same manner as the single mutation at position 372, and would also be suitable in a transposase of the present invention. It may also be possible to reduce the ability of a Tn5 transposase to multimerize without altering the wild type sequence in the so-called dimerization region, for example by adding into the system another protein or non-protein agent that blocks the dimerization site. Alternatively, the dimerization region could be removed entirely from the transposase protein.

As was noted above, the inhibitor protein, encoded in partially overlapping sequence with the transposase, can interfere with transposase activity. As such, it is desired that the amount of inhibitor protein be reduced over the amount observed in wild type in vivo. For the present assay, the transposase is used in purified form, and it may be possible to separate the transposase from the inhibitor (for example, according to differences in size) before use. However, it is also possible to genetically eliminate the possibility of having any contaminating inhibitor protein present by removing its start codon from the gene that encodes the transposase.

An AUG in the wild type Tn5 transposase gene that encodes methionine at transposase amino acid 56 is the first codon of the inhibitor protein. However, it has already been shown that replacement of the methionine at position 56 has no apparent effect upon the transposase activity, but at the same time prevents translation of the inhibitor protein, thus resulting in a somewhat higher transposition rate. Weigand, T. W. and W. S. Reznikoff, "Characterization of Two Hypertransposing Tn5 Mutants," *J. Bact.* 174:1229–1239 (1992), incorporated herein by reference. In particular, the present inventors have replaced the methionine with an alanine in the preferred embodiment (and have replaced the methionine-encoding AUG codon with an alanine-encoding GCC). A preferred transposase of the present invention therefore includes an amino acid other than methionine at amino acid position 56, although this change can be considered merely technically advantageous (since it ensures the absence of the inhibitor from the in vitro system) and not essential to the invention (since other means can be used to eliminate the inhibitor protein from the in vitro system).

The most preferred transposase amino acid sequence known to the inventors differs from the wild type at amino acid positions 54, 56, and 372. The mutations at positions 54 and 372 separately contribute approximately a 10-fold increase to the rate of transposition reaction in vivo. When the mutations are combined using standard recombinant techniques into a single molecule containing both classes of mutations, reaction rates of at least about 100-fold higher than can be achieved using wild type transposase are observed when the products of the in vitro system are tested in vivo. The mutation at position 56 does not directly affect the transposase activity.

Other mutants from wild type that are contemplated to be likely to contribute to high transposase activity in vitro include, but are not limited to glutaminic acid-to-lysine at position 110, and glutamic acid to lysine at position 345.

It is, of course, understood that other changes apart from these noted positions can be made to the modified transposase (or to a construct encoding the modified transposase) without adversely affecting the transposase activity. For example, it is well understood that a construct encoding such a transposase could include changes in the third position of codons such that the encoded amino acid does not differ from that described herein. In addition, certain codon changes have little or no functional effect upon the transposition activity of the encoded protein. Finally, other changes may be introduced which provide yet higher transposition activity in the encoded protein. It is also specifically envisioned that combinations of mutations can be combined to encode a modified transposase having even higher transposition activity than has been exemplified herein. All of these changes are within the scope of the present invention. It is noted, however, that a modified transposase containing the EK110 and EK345 mutations (both described by Weigand and Reznikoff, supra, had lower transposase activity than a transposase containing either mutation alone.

After the enzyme is prepared and purified, as described supra, it can be used in the in vitro transposition reaction described above to introduce any desired transposable element from a donor DNA into a target DNA. The donor DNA can be circular or can be linear. If the donor DNA is linear, it is preferred that the repeat sequences flanking the transposable element should not be at the termini of the linear fragment but should rather include some DNA upstream and downstream from the region flanked by the repeat sequences.

As was noted above, Tn5 transposition requires a pair of eighteen or nineteen base long termini. The wild type Tn5 outside end (OE) sequence (5'-CTGACTCTTATACACAAGT-3') (SEQ ID NO: 7) has been described. It has been discovered that a transposase-catalyzed in vitro transposition frequency at least as high as that of wild type OE is achieved if the termini in a construct include bases ATA at positions 10, 11, and 12, respectively, as well as the nucleotides in common between wild type OE and IE (e.g., at positions 1–3, 5–9, 13, 14, 16, and optionally 19). The nucleotides at positions 4, 15, 17, and 18 can correspond to the nucleotides found at those positions in either wild type OE or wild type IE. It is noted that the transposition frequency can be enhanced over that of wild type OE if the nucleotide at position 4 is a T. The importance of these particular bases to transposition frequency has not previously been identified.

It is noted that these changes are not intended to encompass every desirable modification to OE. As is described elsewhere herein, these attributes of acceptable termini modifications were identified by screening mutants having randomized differences between IE and OE termini. While the presence in the termini of certain nucleotides is shown herein to be advantageous, other desirable terminal sequences may yet be obtained by screening a larger array of degenerate mutants that include changes at positions other than those tested herein as well as mutants containing nucleotides not tested in the described screening. In addition, it is clear to one skilled in the art that if a different transposase is used, it may still be possible to select other variant termini, more compatible with that particular transposase.

Among the mutants shown to be desirable and within the scope of the invention are two hyperactive mutant OE sequences that were identified in vivo. Although presented here as single stranded sequences, in fact, the wild type and mutant OE sequences include complementary second strands. The first hyperactive mutant, 5'-CTGTCTCTTATACACATCT-3' (SEQ ID NO: 8), differs from the wild type OE sequence at positions 4, 17, and 18, counting from the 5' end, but retains ATA at positions 10–12. The second, 5'-CTGTCTCTTATACAGATCT-3' (SEQ ID NO: 9), differs from the wild type OE sequence at positions 4, 15, 17, and 18, but also retains ATA at positions 10–12. These two hyperactive mutant OE sequences differ from one another only at position 15, where either G or C is present. OE-like activity (or higher activity) is observed in a mutant sequence when it contains ATA at positions 10, 11 and 12. It may be possible to reduce the length of the OE sequence from 19 to 18 nucleotide pairs with little or no effect.

When one of the identified hyperactive mutant OE sequences flanks a substrate DNA, the in vivo transposition frequency of EK54/MA56 transposase is increased approximately 40–60 fold over the frequency that is observed when wild type OE termini flank the transposable DNA. The EK54/MA56 transposase is already known to have an in vivo transposition frequency approximately an 8–10 fold higher than wild type transposase, using wild type OE termini. Tn5 transposase having the EK54/MA56 mutation is known to bind with greater avidity to OE and with lesser avidity to the Tn5 inside ends (IE) than wild type transposase.

A suitable mutant terminus in a construct for use in the assays of the present invention is characterized biologically as yielding more papillae per colony in a comparable time, say 68 hours, than is observed in colonies harboring wild type OE in a comparable plasmid. Wild type OE can yield about 100 papillae per colony when measured 68 hours after plating in a papillation assay using EK54/MA56 transposase, as is described elsewhere herein. A preferred mutant would yield between about 200 and 3000 papillae per colony, and a more preferred mutant between about 1000 and 3000 papillae per colony, when measured in the same assay and time frame. A most preferred mutant would yield between about 2000 and 3000 papillae per colony when assayed under the same conditions. Papillation levels may be even greater than 3000 per colony, although it is difficult to quantitate at such levels.

Transposition frequency is also substantially enhanced in the in vitro transposition assay of the present invention when substrate DNA is flanked by a preferred mutant OE sequence and a most preferred mutant transposase (comprising EK54/MA56/LP372 mutations) is used. Under those conditions, essentially all of the substrate DNA is converted into transposition products.

The rate of in vitro transposition observed using the hyperactive termini is sufficiently high that, in the experience of the inventors, there is no need to select for transposition events. All colonies selected at random after transformation for further study have shown evidence of transposition events.

This advance can represent a significant savings in time and laboratory effort. For example, it is particularly advantageous to be able to improve in vitro transposition frequency by modifying DNA rather than by modifying the transposase because as transposase activity increases in host cells, there is an increased likelihood that cells containing the transposase are killed during growth as a result of aberrant DNA transpositions. In contrast, DNA of interest containing the modified OE termini can be grown in sources completely separate from the transposase, thus not putting the host cells at risk.

Without intending to limit the scope of this aspect of this invention, it is apparent that the tested hyperactive termini do not bind with greater avidity to the transposase than do wild type OE termini. Thus, the higher transposition frequency brought about by the hyperactive termini is not due to enhanced binding to transposase.

The transposable element between the termini can include any desired nucleotide sequence. The length of the transposable element between the termini should be at least about 50 base pairs, although smaller inserts may work. No upper limit to the insert size is known. However, it is known that a donor DNA portion of about 300 nucleotides in length can function well. By way of non-limiting examples, the transposable element can include a coding region that encodes a detectable or selectable protein, with or without associated regulatory elements such as promoter, terminator, or the like.

If the element includes such a detectable or selectable coding region without a promoter, it will be possible to identify and map promoters in the target DNA that are uncovered by transposition of the coding region into a position downstream thereof, followed by analysis of the nucleic acid sequences upstream from the transposition site.

Likewise, the element can include a primer binding site that can be transposed into the target DNA, to facilitate sequencing methods or other methods that rely upon the use of primers distributed throughout the target genetic material. Similarly, the method can be used to introduce a desired restriction enzyme site or polylinker, or a site suitable for another type of recombination, such as a cre-lox, into the target.

Figure 9:
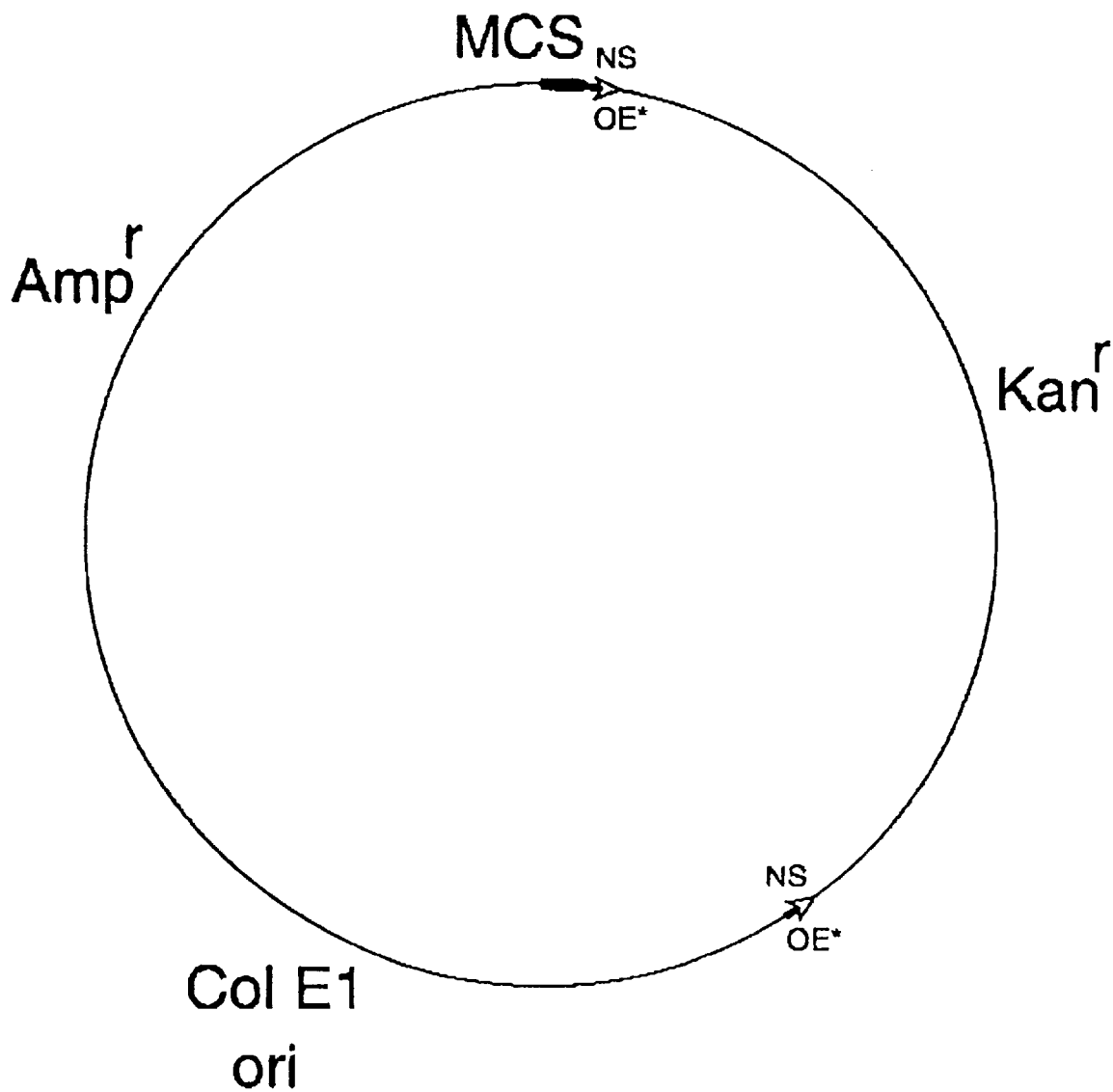
FIG. 9 shows plasmid pRZ7075, a plasmid into which a nucleic acid insert can be cloned. The plasmid includes an origin of replication, a pair of suitable OE termini, a pair of markers for selection/screening, a site into which an insert can be cloned, and stop codons in three reading frames adjacent to the OE termini for terminating translation of a coding sequence present on the plasmid.

The genetic construct for use in the method for intramolecular in vitro transposition, described below, includes a transposable portion and a donor backbone portion. The transposable portion includes a pair of terminal transposon outer ends (OE), depicted in FIG. 9 as arrowheads, which are present in inverted orientation relative to one another. Although wild type Tn5 OE termini are suitably used in the genetic construct, the OE termini are preferably modified from wild type in accordance with the invention for use with an active transposase. The modified OE termini selected for use with the mutant EK54-LP372 transposase, disclosed elsewhere herein, are suitable and are considered preferred components of the construct.

The transposable portion also encodes an origin of replication operable in a selected host cell and a first selectable marker operable in a host cell, nearby to the origin of replication. The origin should be compatible with a host cell in which the construct is replicated. A suitable origin of replication is the ColE1 origin of replication. The ColE1 origin is suitable for use in a variety of bacterial host cells, including DH5α E. coli cells, which are considered a preferred cell by the inventors. The selectable marker can be, for example, a gene that confers upon the host cells a resistance to an antibiotic. Exemplary antibiotic resistance genes are the genes that confer ampicillin resistance or kanamycin resistance.

The construct should also include one or more sites into which an insert of interest can be cloned. A multicloning site that provides desirable unique cleavage sites to the vector can be included to facilitate that process. The nucleotide sequences of many multicloning sites are well known in the art, The donor backbone portion (DBB) of the genetic construct includes the remainder of the genetic construct. The donor backbone portion encodes a second selectable marker that can be distinguished from the first selectable marker, or includes a gene whose presence or absence can be detected by a change in color of the host colonies. An exemplary color indicator gene is the β-galactosidase gene. By providing discrete markers on the donor backbone and on the excised transposable portion of the genetic construct, one can readily distinguish DNA molecules that have undergone a transposition event and lost the donor backbone, from those DNA molecules that have not.

The insert of interest, which can, but need not represent a protein-encoding sequence, is also provided in the transposable portion. The insert is not limited to any particular nucleotide sequence. The in vitro transposition system is target-sequence-independent, and can operate on any insert sequence, without regard to its origin or source. For example, the insert can derive from prokaryotic, eukaryotic or synthetic genetic material. There is no reason to believe that any nucleotide sequence would not function in the method of the present invention. The insert size can range up to at least about 15 or 20 kilobases. A practical lower limit on the size of the insert is a size that does not interfere with the ability of the genetic construct to bring the OE termini into proper orientation for transposition to occur. The lower size limit of the insert is thought to be about 150 to 200 base pairs in a genetic construct of the size described herein. The applicants have observed that the ends of the insert sequence are slightly favored as transposition target sites when the insert is larger than about 5000 base pairs.

If the construct is intended to encode a protein or polypeptide fragment, the construct can optionally include other modifications to facilitate purification and/or analysis of polypeptide or protein fragments generated. The modifications can be provided on the construct, on the insert, or in some combination of the two, as long as the insert-containing construct includes all required upstream regulatory signals, such as a regulated promoter and translation initiation signals. The insert has to be constructed to include a coding sequence provided in frame relative to the initiating AUG codon, which can itself be provided on the insert or in the region upstream from the insert. The modifications can include, but are not limited to, a tag sequence or a site for labeling an amino acid residue of a protein or polypeptide. The tag sequence can be multiple histidine residues encoded upstream of the insert, wherein the encoded histidine residues can bind to divalent cations ($Ni^{2+}$) immobilized on a resin. A histidine tag system for protein purification is available commercially from Novagen, Madison, Wis. The site for labeling can be a kinase site that can be provided upstream of the insert sequence so that any protein generated can be labeled in a kinase reaction. Protein kinase systems are commercially available from, for example, Novagen. The modification can also include a protease specific sequence for cleaving a portion of the encoded protein or polypeptide fragment, as desired.

It will be understood by those skilled in the art that it is desirable to minimize the overall size of the genetic construct into which the insert is provided because the likelihood that an intramolecular transposition event will occur in the inserted sequence increases with an increase in the proportion of the construct that is attributable to the insert. The exemplified genetic construct contains little extraneous material in the transposable portion, although it may be possible to further reduce the size of the genetic construct by reducing the size of one or both selectable marker genes.

Figure 10:
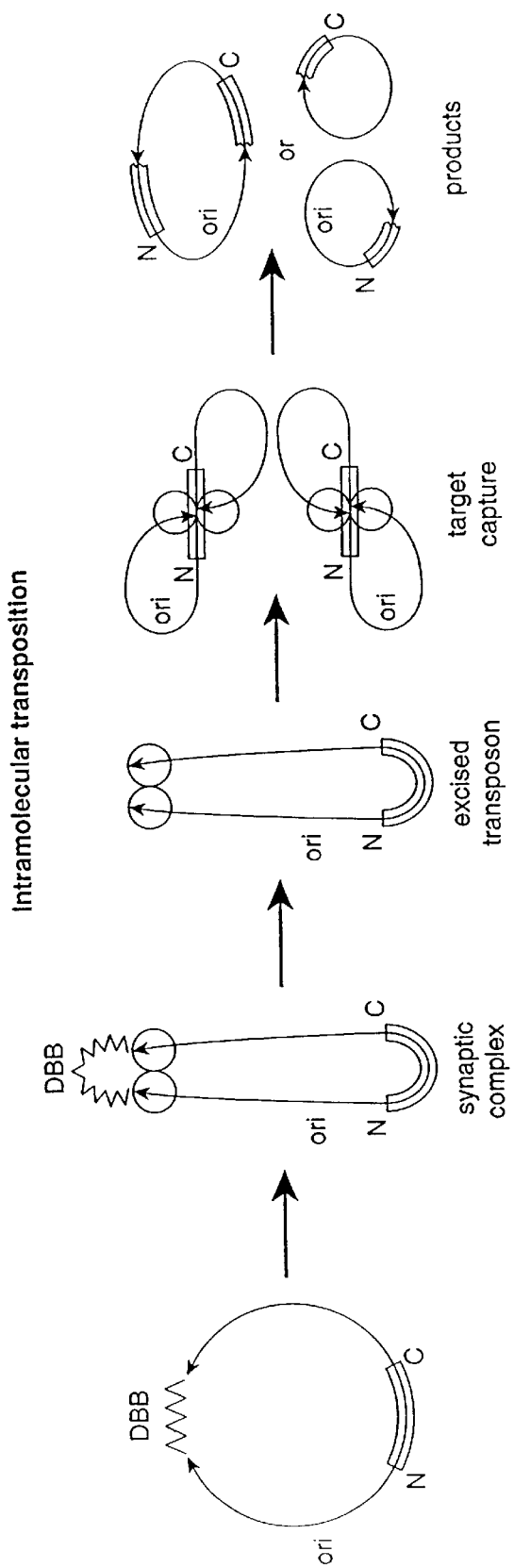
FIG. 10 schematically depicts the principle of intramolecular transposition to produce nested deletions and inversions.

FIG. 10 depicts the principle underlying the method of the present invention. In FIG. 10, a suitable vector containing an exemplary hypothetical polypeptide is shown. The N-terminus of the polypeptide corresponds to the 5' end of the polypeptide-encoding nucleotide insert sequence. The C-terminus corresponds to the 3' end of the polypeptide-encoding nucleotide insert sequence.

In the method for in vitro intramolecular transposition, a genetic construct for intramolecular transposition, as described above, is provided at low concentration, to encourage intramolecular, as opposed to intermolecular, transposition. The applicants have found a suitable amount of nucleic acid to be in the range of 0.05–0.005 $\mu g/\mu l$ of reaction mix. At 0.05 $\mu g/\mu l$, 95% of the transposition events are intramolecular. At 0.005 $\mu g/\mu l$, or lower, about 100% of the events are intramolecular transpositions.

As is shown in FIG. 10 as a pair of circles, a synaptic complex forms between the OE termini (arrowheads) and the transposase, and the transposable portion is excised from the donor backbone. In a target capture step, the two types of intramolecular transposition, deletion and inversion, can occur, the selection of transposition type being governed by the relative spatial relationship of the termini and the transposase. The product of the first type of transposition, shown in the upper structure, is an inversion of a portion of the genetic construct. In the example shown, the transposition site is in the coding region. In the product, the coding region is split, as shown. Where an inversion is generated, a nine base pair direct repeat follows each of the OE termini adjacent to the inversion end points.

In the second type of transposition, shown in the lower structure, the transposition products are a pair of plasmids, where each contains only a portion of the original target sequence. Notably, only one of the two products of this type of transposition includes an origin of replication. Thus, only one half of these products can persist after the transposition reaction mix is transformed into host cells.

One skilled in the art will appreciate that the intramolecular transposition is random, or nearly random, into any other point on the genetic construct. In practice, in a mixture of products of the described in vitro transposition, a wide variety of transposition end points will be represented. When the mixture is introduced into suitable host cells, the cells can be grown as individual colonies, each of which will contain a unique plasmid, some of which will contain deletions, others inversions. Some constructs will not have undergone a transformation event.

To determine which colonies contain constructs that have undergone transposition events, a selective marker scheme is employed. The cells are grown in the presence of a first selective agent. The only colonies that can grow in the presence of that agent are those that contain a construct having an origin of replication and the first selective marker that confers resistance to the first selective agent. Cells containing those plasmids that have lost the donor backbone are selected by rescreening the selected colonies for sensitivity to the second selective agent. If a color indicator is used, colonies that have lost the donor backbone (and the indicator gene between the OE termini) will be different in color from those that have not undergone intramolecular transposition. A suitable color assay employs the β-galactosidase gene between the OE termini on the donor backbone.

Colonies that meet the selection/screening criteria can be selected for analysis. The plasmids from each can be prepared according to known methods, and the nucleic acid sequence of the insert in each plasmid can be determined by utilizing suitable sequencing primers adjacent to the insert, in a manner known to the art. The collection of plasmids obtained will represent a battery of nested deletions from which it may be possible to determine the complete sequence of the original insert, if enough plasmids are evaluated. The sequencing of nested deletions is facilitated by preparing sequencing primers that correspond to a sequence in proximity to the OE terminus. Primers for sequencing the deletion products need only correspond to the one outside end that is juxtaposed to the deletion point. For inversion products, a primer corresponding to the second strand can be employed to obtain the sequence of the second strand.

As noted, deletion products produced in the in vitro transposition system can also be employed to transcribe and/or translate N-terminal protein or polypeptide fragments truncated at the C-terminal end in an in vitro transcription/translation system, or after transformation into a host cell. The insert should include appropriate transcriptional and/or translational control sequences (or such sequences can be provided upstream of the point at which the insert is introduced onto the genetic construct). The coding sequence located downstream from the control sequences can be expressed from the 5' (N-terminal) end to the transposition site. Sequences further 3' to the transposition point are absent from the deletion product. To ensure that the protein is properly truncated at the deletion site, the genetic construct can include nonsense codons in all three reading frames in the transposable portion, at positions adjacent to the OE termini.

C-terminal protein or polypeptide fragments truncated at their N-terminal end can be made in much the same manner using a similar genetic construct. The insert is positioned in the construct such that the 3' end of the coding sequence is "upstream" from the 5' end (i.e., in the reverse orientation from its position in the previously described case). The transcriptional and/or translational control sequences (which can include, e.g., a suitable promoter and a Shine-Delgarno sequence) are provided in the transposable portion of the construct near the OE so that when the OE attacks the insert sequence, the control sequences are operably engaged with the insert sequence at the transposition site. It is noted that, as a result of reading frame issues, genuine transcription and translation will occur in only one-third of the C-terminal fragment products obtained.

To ensure that deletion products are obtained, or to confirm that the deletion products cover a range of appropriate size DNA molecules, DNA can be isolated from individual colonies after transposition, and can be separated by size, for example, on a gel. It is noted that deletions are nested at only one end of the insert DNA; the second end is unaltered.

The invention can be better understood upon consideration of the following examples which are intended to be exemplary and not limiting on the invention.

EXAMPLES

To obtain the transposase modified at position 54, the first third of the coding region from an existing DNA clone that encodes the Tn5 transposase but not the inhibitor protein (MA56) was mutagenized according to known methods and DNA fragments containing the mutagenized portion were cloned to produce a library of plasmid clones containing a full length transposase gene. The clones making up the library were transformed into *E. coli* K-12 strain MDW320 bacteria which were plated and grown into colonies. Transposable elements provided in the bacteria on a separate plasmid contained a defective lacZ gene. The separate plasmid, pOXgen386, was described by Weinreich, M. et al., "A functional analysis of the Tn5 Transposase: Identification of Domains Required for DNA Binding and Dimerization," *J. Mol. Biol.* 241:166–177 (1993), incorporated herein by reference. Colonies having elevated transposase activity were selected by screening for blue (LacZ) spots in white colonies grown in the presence of X-gal. This papillation assay was described by Weinreich, et al. (1993), supra. The 5'-most third of Tn5 transposase genes from such colonies were sequenced to determine whether a mutation was responsible for the increase in transposase activity. It was determined that a mutation at position 54 to lysine (K) correlated well with the increase in transposase activity. Plasmid pRZ5412-EK54 contains lysine at position 54 as well as the described alanine at position 56.

The fragment containing the LP372 mutation was isolated from pRZ4870 (Weinreich et al (1994)) using restriction enzymes NheI and BglII, and were ligated into NheI-BglII cut pRZ5412-EK54 to form a recombinant gene having the mutations at positions 54, 56 and 372, as described herein and shown in SEQ ID NO:1. The gene was tested and shown to have at least about a one hundred fold increase in activity relative to wild type Tn5 transposase. Each of the mutants at positions 54 and 372 alone had about a 10-fold increase in transposase activity.

The modified transposase protein encoded by the triple-mutant recombinant gene was transferred into commercial T7 expression vector pET-21D (commercially available from Novagen, Madison, Wis.) by inserting a BspHI/SalI fragment into NhoI/XhoI fragment of the pET-21D vector. This cloning puts the modified transposase gene under the control of the T7 promoter, rather than the natural promoter of the transposase gene. The gene product was overproduced in BL21(DE3)pLysS bacterial host cells, which do not contain the binding site for the enzyme, by specific induction in a fermentation process after cell growth is complete. (See, Studier, F. W., et al., "Use of T7 RNA Polymerase to Direct Expression of Cloned Genes," *Methods Enzymol.* 185:60–89 (1990)). The transposase was partially purified using the method of de la Cruz, modified by inducing overproduction at 33 or 37° C. After purification, the enzyme preparation was stored at −70° C. in a storage buffer (10% glycerol, 0.7M NaCl, 20 mM Tris-HCl, pH 7.5, 0.1% TRITON-X100 and 10 mM CHAPS) until use. This storage buffer is to be considered exemplary and not optimized.

A single plasmid (pRZTL1, FIG. 1) was constructed to serve as both donor and target DNA in this Example. The complete sequence of the pRZTL1 plasmid DNA is shown and described in SEQ ID NO:3. Plasmid pRZTL1 contains two Tn5 19 base pair OE termini in inverted orientation to each other. Immediately adjacent to one OE sequence is a gene that would encode tetracycline resistance, but for the lack of an upstream promoter. However, the gene is expressed if the tetracycline resistance gene is placed downstream of a transcribed region (e.g., under the control of the promoter that promotes transcription of the chloramphenicol resistance gene also present on pRZTL1). Thus, the test plasmid pRZTL1 can be assayed in vivo after the in vitro reaction to confirm that transposition has occurred. The plasmid pRZTL1 also includes an origin of replication in the transposable element, which ensures that all transposition products are plasmids that can replicate after introduction in host cells.

The following components were used in typical 20 μl in vitro transposition reactions:

Modified transposase: 2 μl (approximately 0.1 μg enzyme/μl) in storage buffer (10% glycerol, 0.7M NaCl, 20 mM Tris-HCl, pH 7.5, 0.1% TRITON-X100 and 10 mM CHAPS)

Donor/Target DNA: 18 μl (approximately 1–2 μg) in reaction buffer (at final reaction concentrations of 0.1 M potassium glutamate, 25 mM Tris acetate, pH 7.5, 10 mM $Mg^{2+}$-acetate, 50 μg/ml BSA, 0.5 mM β-mercaptoethanol, 2 mM spermidine, 100 μg/ml tRNA).

At 20 °C., the transposase was combined with pRZTL1 DNA for about 60 minutes. Then, the reaction volume was increased by adding two volumes of reaction buffer and the temperature was raised to 37° C. for 2–3 hours whereupon cleavage and strand transfer occurred.

Efficient in vitro transposition was shown to have occurred by in vivo and in vitro methods. In vivo, many tetracycline-resistant colonies were observed after transferring the nucleic acid product of the reaction into DH5α bacterial cells. As noted, tetracycline resistance can only arise in this system if the transposable element is transposed downstream from an active promoter elsewhere on the plasmid. A typical transpositional frequency was 0.1% of cells that received plasmid DNA, as determined by counting chloramphenicol resistant colonies. However, this number underestimates the total transposition event frequency because the detection system limits the target to 1/16 of the total.

Moreover, in vitro electrophoretic (1% agarose) and DNA sequencing analyses of DNA osolated from purified colonies revealed products of true transposition events. Result of typical reaction using circular plasmid pRZTL1 sustrates are shown in Lanes 4 & 5. Lane 6 of FIG. 2 shows the results obtained using linear plasmid pRZTL1 substrates.

The bands were revealed on 1% agarose gels by staining with SYBR Green (FMC Bioproducts) and were scanned on a FLOURIMAGER SI (Molecular Dynamics). In FIG. 2, lane 1 shows relaxed circle, linear, and closed circle versions of pRZTL1. Lanes 2 and 3 show intramolecular and intermolecular transposition products after in vitro transposition of pRZTL1, respectively. The products were purified from electroporated DH5α cells and were proven by size and sequence analysis to be genuine transposition products. Lanes 4 and 5 represent products of two independent in vitro reactions using a mixture of closed and relaxed circular test plasmid substrates. In lane 6, linear pRZTL1 (XhoI-cut) was the reaction substrate. Lane 7 includes a BstEII digest of lambda DNA as a molecular weight standard.

Figure 2:
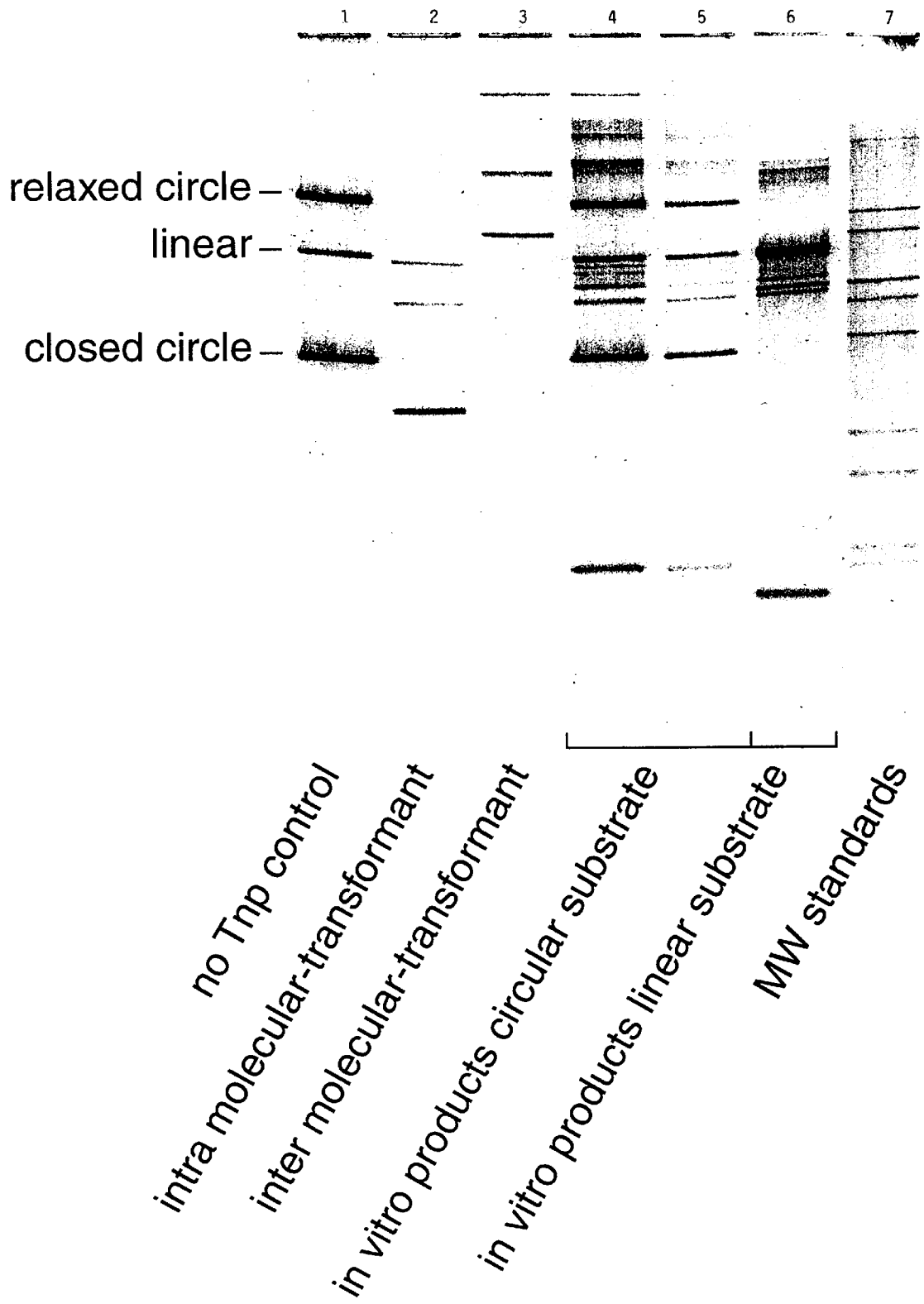
FIG. 2 depicts an electrophoretic analysis of plasmid pRZTL1 before and after in vitro transposition. Data obtained using both circular and linear plasmid substrates are shown.
Figure 3:
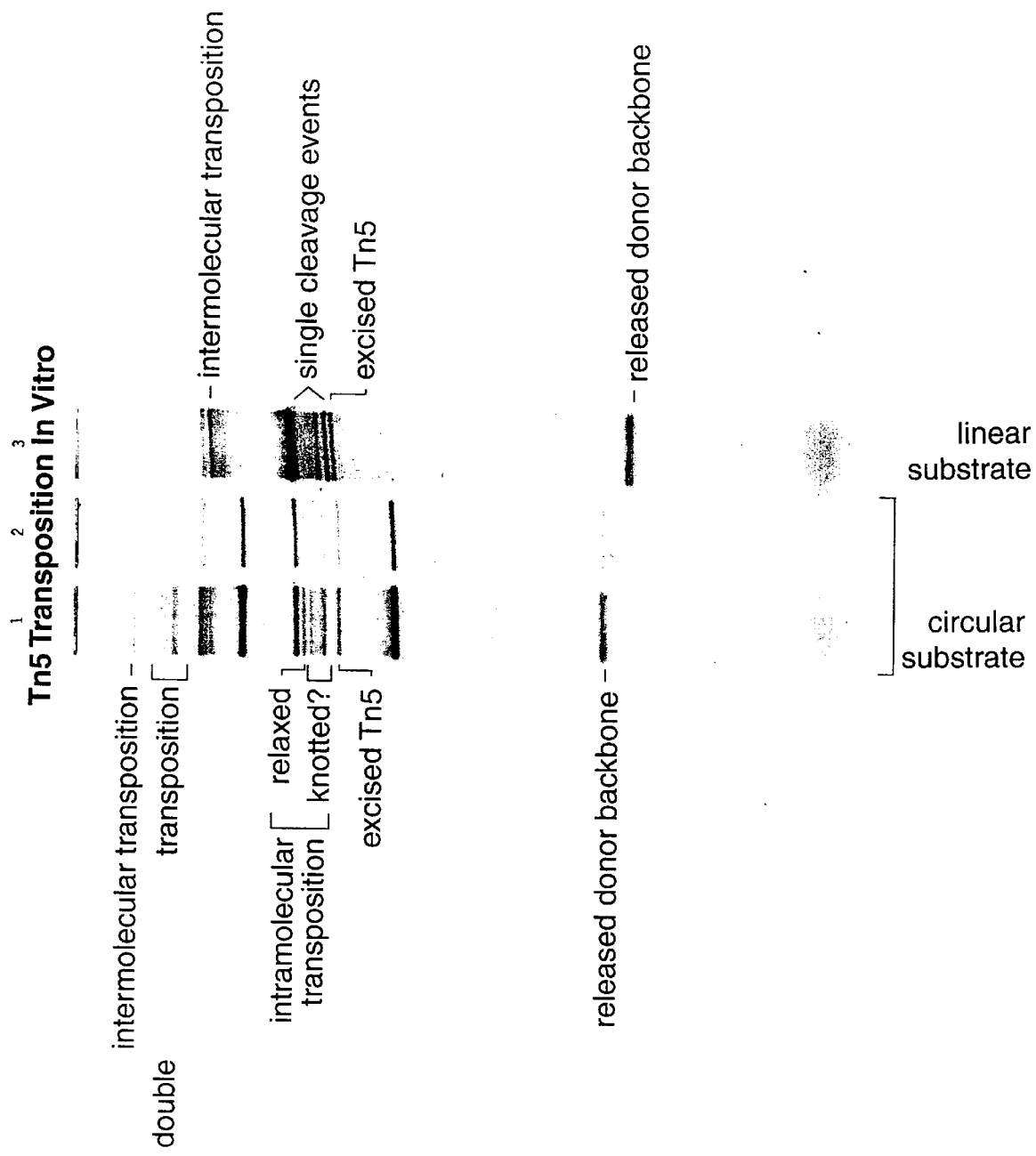
FIG. 3 is an electrophoretic analysis of plasmid pRZTL1 after in vitro transposition, including further analysis of the molecular species obtained using circular and linear plasmid substrates.

FIG. 3 reproduces lanes 4, 5, and 6 of FIG. 2 and shows an analysis of various products, based upon secondary restriction digest experiments and re-electroporation and DNA sequencing. The released donor DNA corresponds to the fragment of pRZTL1 that contains the kanamycin resistance gene between the two OE sequences, or, in the case of the linear substrate, the OE-XhoI fragment. Intermolecular transposition products can be seen only as relaxed DNA circles. Intramolecular transposition products are seen as a ladder, which results from conversion of the initial superhelicity of the substrate into DNA knots. The reaction is efficient enough to achieve double transposition events that are a combination of inter- and intramolecular events.

A preliminary investigation was made into the nature of the termini involved in a transposition reaction. Wild type Tn5 OE and IE sequences were compared and an effort was undertaken to randomize the nucleotides at each of the seven positions of difference. A population of oligonucleotides degenerate at each position of difference was created. Thus, individual oligonucleotides in the population randomly included either the nucleotide of the wild type OE or the wild type IE sequence. In this scheme, $2^7$ (128) distinct oligonucleotides were synthesized using conventional tools. These oligonucleotides having sequence characteristics of both OE and IE are referred to herein as OE/IE-like sequences. To avoid nomenclature issues that arise because the oligonucleotides are intermediate between OE and IE wild type sequences, the applicants herein note that selected oligonucleotide sequences are compared to the wild type OE rather than to wild type IE, unless specifically noted. It will be appreciated by one skilled in the art that if IE is selected as the reference point, the differences are identical but are identified differently.

The following depicts the positions (x) that were varied in this mutant production scheme. WT OE is shown also at SEQ ID NO: 7, WT IE at SEQ ID NO: 10.

```
5'-CTGACTCTTATACACAAGT-3'   (WT OE)
    x    xxx  x xx          (positions of difference)
5'-CTGTCTCTTGATCAGATCT-3'   (WT IE)
```

In addition to the degenerate OE/IE-like sequences, the 37- base long synthetic oligonucleotides also included terminal SphI and KpnI restriction enzyme recognition and cleavage sites for convenient cloning of the degenerate oligonucleotides into plasmid vectors. Thus, a library of randomized termini was created from population of $2^7$ (128) types of degenerate oligonucleotides.

Figure 4:
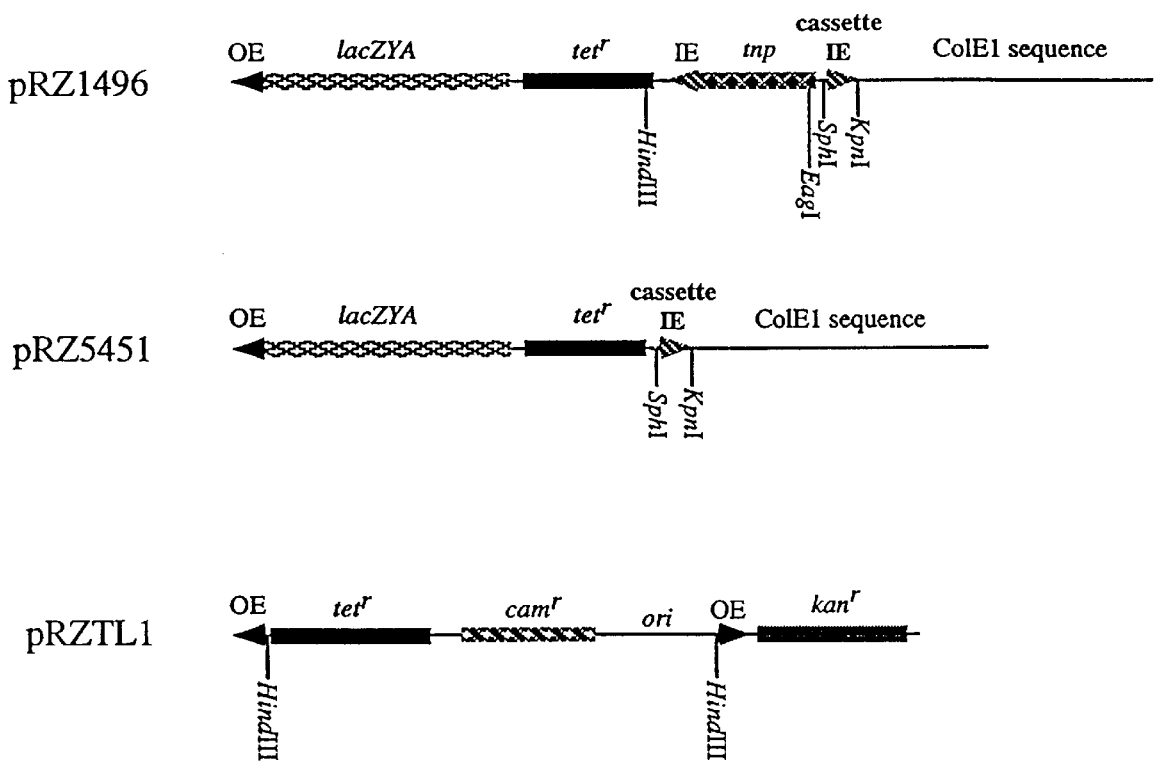
FIG. 4 shows plasmids pRZ1496, pRZ5451 and pRZTL1, which are detailed in the specification.

FIG. 4 shows pRZ1496, the complete sequence of which is presented as SEQ ID NO:11. The following features are noted in the sequence:

| Feature | Position |
|---|---|
| WT OE | 94–112 |
| LacZ coding | 135–3137 |
| LacY coding | 3199–4486 |
| LacA coding | 4553–6295 |
| tet$^r$ coding | 6669–9442 |
| transposase coding | 10683–12111 (Comp. Strand) |
| Cassette IE | 12184–12225 |
| colE1 sequence | 127732–19182 |

The IE cassette shown in FIG. 4 was excised using SphI and KpnI and was replaced, using standard cleavage and ligation methods, by the synthetic termini cassettes comprising OE/IE-like portions. Between the fixed wild type OE sequence and the OE/IE-like cloned sequence, plasmid pRZ1496 comprises a gene whose activity can be detected, namely LacZYA, as well as a selectable marker gene, tet$^r$. The LacZ gene is defective in that it lacks suitable transcription and translation initiation signals. The LacZ gene is transcribed and translated only when it is transposed into a position downstream from such signals.

The resulting clones were transformed using electroporation into dam$^-$, LacZ$^-$ bacterial cells, in this case JCM101/pOXgen cells which were grown at 37° C. in LB medium under standard conditions. A dam$^-$ strain is preferred because dam methylation can inhibit IE utilization and wild type IE sequences include two dam methylation sites. A dam$^-$ strain eliminates dam methylation as a consideration in assessing transposition activity. The Tet$^r$ cells selected were LacZ$^-$; transposition-activated Lac expression was readily detectable against a negative background. pOXgen is a non-essential F factor derivative that need not be provided in the host cells.

In some experiments, the EK54/MA56 transposase was encoded directly by the transformed pRZ1496 plasmid. In other experiments, the pRZ1496 plasmid was modified by deleting a unique HindIII/EagI fragment (nucleotides 9112–12083) from the plasmid (see FIG. 4) to prevent transposase production. In the latter experiments, the host cells were co-transformed with the HindIII/EagI-deleted plasmid, termed pRZ5451 (FIG. 4), and with an EK54/MA56 transposase-encoding chloramphenicol-resistant plasmid. In some experiments, a comparable plasmid encoding a wild type Tn5 transposase was used for comparison.

Transposition frequency was assessed by a papillation assay that measured the number of blue spots (Lac producing cells or "papillae") in an otherwise white colony. Transformed cells were plated (approx. 50 colonies per plate) on Glucose minimal Miller medium (Miller, J., Exeriments in Molecular Genetics, Cold Spring Harbor Laboratory, Cold Spring Harbor, N.Y. (1972)) containing 0.3% casamino acids, 5-bromo-4-chloro-3-indolyl-β-D-galactoside (40 µg/ml) and phenyl-β-D-galactoside (0.05%). The medium contained tetracycline (15 µg/ml) and, where needed, chloramphenicol (20 µg/ml). Colonies that survived the selection were evaluated for transposition frequency in vivo. Although colonies exhibiting superior papillation were readily apparent to the naked eye, the number of blue spots per colony were determined over a period of several days (approximately 90 hours post-plating).

To show that the high-papillation phenotype was conferred by the end mutations in the plasmids, colonies were re-streaked if they appeared to have papillation levels higher than was observed when wild type IE was included on the plasmid. Colonies picked from the streaked culture plates were themselves picked and cultured. DNA was obtained and purified from the cultured cells, using standard protocols, and was transformed again into "clean" JCM101/pOXgen cells. Papillation levels were again compared with wild type IE-containing plasmids in the above-noted assays, and consistent results were observed.

To obtain DNA for sequencing of the inserted oligonucleotide, cultures were grown from white portions of 117 hyperpapillating colonies, and DNA was prepared from each colony using standard DNA miniprep methods. The DNA sequence of the OE/IE-like portion of 117 clones was determined (42 from transformations using pRZ1496 as the cloning vehicle; 75 from transformations using pRZ5451 as the cloning vehicle). Only 29 unique mutants were observed. Many mutants were isolated multiple times. All mutants that showed the highest papillation frequencies contain OE-derived bases at positions 10, 11, and 12. When the OE-like bases at these positions were maintained, it was impossible to measure the effect on transposition of other changes, since the papillation level was already extremely high.

One thousand five hundred seventy five colonies were screened as described above. The likelihood that all 128 possible mutant sequences were screened was greater than 95%. Thus, it is unlikely that other termini that contribute to a greater transformation frequency will be obtained using the tested transposase.

TABLE I trans papillation level of hybrid end sequence with EK54 Tnp

| | mutant position | | | | | | | | | | | | | | | | | | | papillation level[a] | # of times isolated[b] |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | | |
| IE (SEQ ID NO:10) | c | t | g | T | c | t | c | t | t | G | A | T | c | a | G | a | T | C | t | VL | 0 |
| OE | | | | A | | | | | | A | T | A | | | C | | A | G | | M | 6 |
| 1 | | | | | | | | | | A | T | A | | | | | | | | H | 2 |
| 2 | | | | | | | | | | A | T | A | | | C | | | | | H | 3 |
| 3 | | | | | | | | | | A | T | A | | | | | A | | | H | 5 |
| 4 | | | | | | | | | | A | T | A | | | C | | A | | | H | 4 |
| 5 | | | | | | | | | | A | T | A | | | C | | | G | | H | 6 |
| 6 | | | | | | | | | | A | T | A | | | | | A | G | | H | 6 |
| 7 | | | | | | | | | | A | T | A | | | C | | A | G | | H | 4 |
| 8 | | | | | | | | | | A | T | A | | | | | | G | | M | 7 |
| 9 | | | | A | | | | | | A | T | A | | | | | | | | M | 3 |
| 10 | | | | A | | | | | | A | T | A | | | C | | | | | M | 2 |
| 11 | | | | A | | | | | | A | T | A | | | | | A | | | M | 1 |

TABLE I-continued trans papillation level of hybrid end sequence with EK54 Tnp

| | _____ mutant position _____ | | | | | | | | | | | | | | | | | | | papillation level[a] | # of times isolated[b] |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | | |
| 12 | | | | A | | | | | | A | T | A | | | | | | G | | | 0 |
| 13 | | | | A | | | | | | A | T | A | | | C | | A | | | | 0 |
| 14 | | | | A | | | | | | A | T | A | | | C | | | G | | M | 4 |
| 15 | | | | A | | | | | | A | T | A | | | | | A | G | | M | 4 |
| 16 | | | | | | | | | | A | T | | | | C | | A | | | L | 2 |
| 17 | | | | | | | | | | A | T | | | | | | A | G | | L | 1 |
| 18 | | | | | | | | | | A | T | | | | C | | A | G | | L | 2 |
| 19 | | | | | | | | | | A | | | | | C | | A | G | | L | 1 |
| 20 | | | | | | | | | | | T | | | | C | | A | G | | L | 1 |
| 21 | | | | | | | | | | | | | | | C | | A | G | | L | 1 |

All hybrid end sequences isolated on pRZ5451 that papillate more frequently than wt IE, when the EK54 Tnp is expressed from pFMA187, are listed.
[a] trans papillation levels of wt IE, wt OE and hybrid end sequences are classified as follows: VL-very low, L-low, M-medium, and H-high.
[b] Although mutants 12 and 13 were not found in this experiment, they were found in cis papillation screening (Table II).

TABLE II cis papillation level of hybrid end sequence with EK54 Tnp

| | _____ mutant position _____ | | | | | | | | | | | | | | | | | | | papillation level[a] | # of times isolated[b] |
|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | | |
| IE (SEQ ID NO:10) | c | t | g | T | c | t | c | t | t | G | A | T | c | a | G | a | T | C | t | L | 0 |
| OE | | | | A | | | | | | A | T | A | | | C | | A | G | | H | 2 |
| 1 | | | | | | | | | | A | T | A | | | | | | | | H | 2 |
| 2 | | | | | | | | | | A | T | A | | | C | | | | | | 0 |
| 3 | | | | | | | | | | A | T | A | | | | | A | | | H | 1 |
| 4 | | | | | | | | | | A | T | A | | | C | | A | | | H | 1 |
| 5 | | | | | | | | | | A | T | A | | | C | | | G | | H | 1 |
| 6 | | | | | | | | | | A | T | A | | | | | A | G | | H | 2 |
| 7 | | | | | | | | | | A | T | A | | | C | | A | G | | H | 3 |
| 8 | | | | | | | | | | A | T | A | | | | | | G | | H | 1 |
| 9 | | | | A | | | | | | A | T | A | | | | | | | | H | 1 |
| 10 | | | | A | | | | | | A | T | A | | | C | | | | | | 0 |
| 11 | | | | A | | | | | | A | T | A | | | | | A | | | H | 2 |
| 12 | | | | A | | | | | | A | T | A | | | | | | G | | MH | 3 |
| 13 | | | | A | | | | | | A | T | A | | | C | | A | | | MH | 1 |
| 14 | | | | A | | | | | | A | T | A | | | C | | | G | | | 0 |
| 15 | | | | A | | | | | | A | T | A | | | | | A | G | | H | 2 |
| 16 | | | | | | | | | | A | T | | | | C | | | | | M | 1 |
| 17 | | | | | | | | | | A | T | | | | | | A | G | | M | 1 |
| 18 | | | | A | | | | | | A | T | | | | C | | | | | M | 2 |
| 19 | | | | A | | | | | | A | T | | | | C | | A | | | M | 2 |
| 20 | | | | A | | | | | | A | T | | | | C | | A | G | | M | 1 |
| 21 | | | | | | | | | | A | | A | | | | | A | | | M | 4 |
| 22 | | | | | | | | | | A | | A | | | | | | G | | M | 1 |
| 23 | | | | | | | | | | A | | A | | | C | | A | G | | M | 1 |
| 24 | | | | | | | | | | A | | | | | C | | A | | | M | 1 |
| 25 | | | | | | | | | | A | | | | | C | | A | | | M | 1 |
| 26 | | | | | | | | | | | T | | | | C | | A | G | | M | 1 |
| 27 | | | | | | | | | | | | | | | C | | A | G | | M | 2 |

All hybrid end sequences isolated on pRZ1496 that papillate more frequently than wt IE, when the EK54 Tnp is expressed from the same plasmid, are listed.
[a] cis papillation levels of wt IE, wt OE and hybrid end sequences are classified as follows: L-low, M-medium, MH-medium high, and H-high.
[b] Although mutants 2, 10 and 14 were not found in this experiment, they were found in trans papillation screening (Tabe I).

Tables I and II report the qualitative papillation level of mutant constructs carrying the indicated hybrid end sequences or the wild type OE or IE end sequences. In the tables, the sequence at each position of the terminus corresponds to wild type IE unless otherwise noted. The applicants intend that, while the sequences are presented in shorthand notation, one of ordinary skill can readily determine the complete 19 base pair sequence of every presented mutant, and this specification is to be read to include all such complete sequences. Table I includes data from trials where the EK54 transposase was provided in trans; Table II, from those trials where the EK54 transposase was provided in cis. Although a transposase provided in cis is more active in absolute terms than a transposase provided in trans, the cis or trans source of the transposase does not alter the relative in vivo transposition frequencies of the tested termini.

Tables I and II show that every mutant that retains ATA at positions 10, 11, and 12, respectively, had an activity comparable to, or higher than, wild type OE, regardless of whether the wild type OE activity was medium (Table I, trans) or high (Table II, cis). Moreover, whenever that three-base sequence in a mutant was not ATA, the mutant exhibited lower papillation activity than wild type OE. It was also noted that papillation is at least comparable to, and tends to be significantly higher than, wild type OE when position 4 is a T.

Quantitative analysis of papillation levels was difficult, beyond the comparative levels shown (very low, low, medium, medium high, and high). However, one skilled in the art can readily note the papillation level of OE and can recognize those colonies having comparable or higher levels. It is helpful to observe the papillae with magnification.

Figure 5:
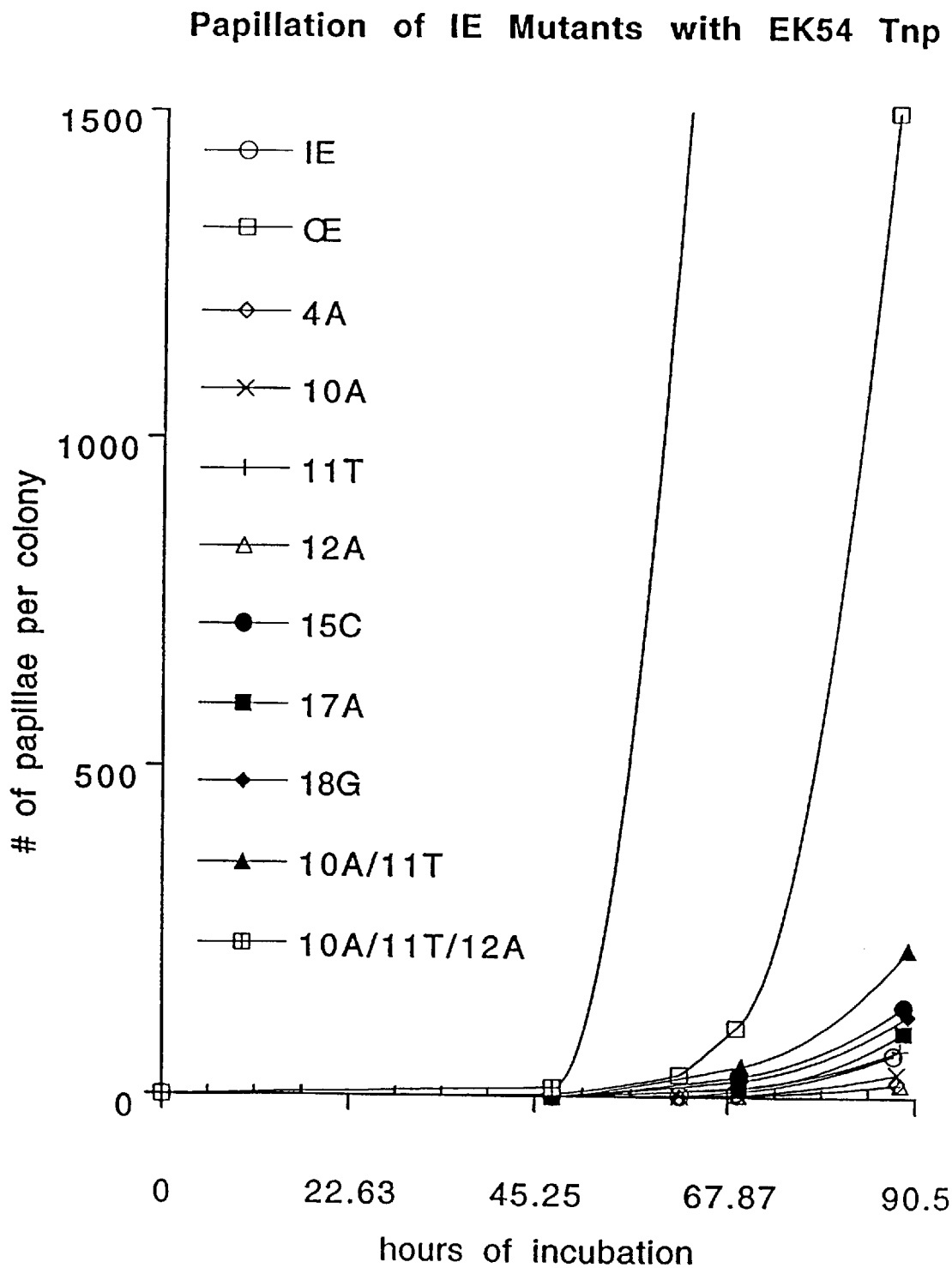
FIG. 5 shows a plot of papillae per colony over time for various mutant OE sequences tested in vivo against EK54/MA56 transposase.
Figure 6:
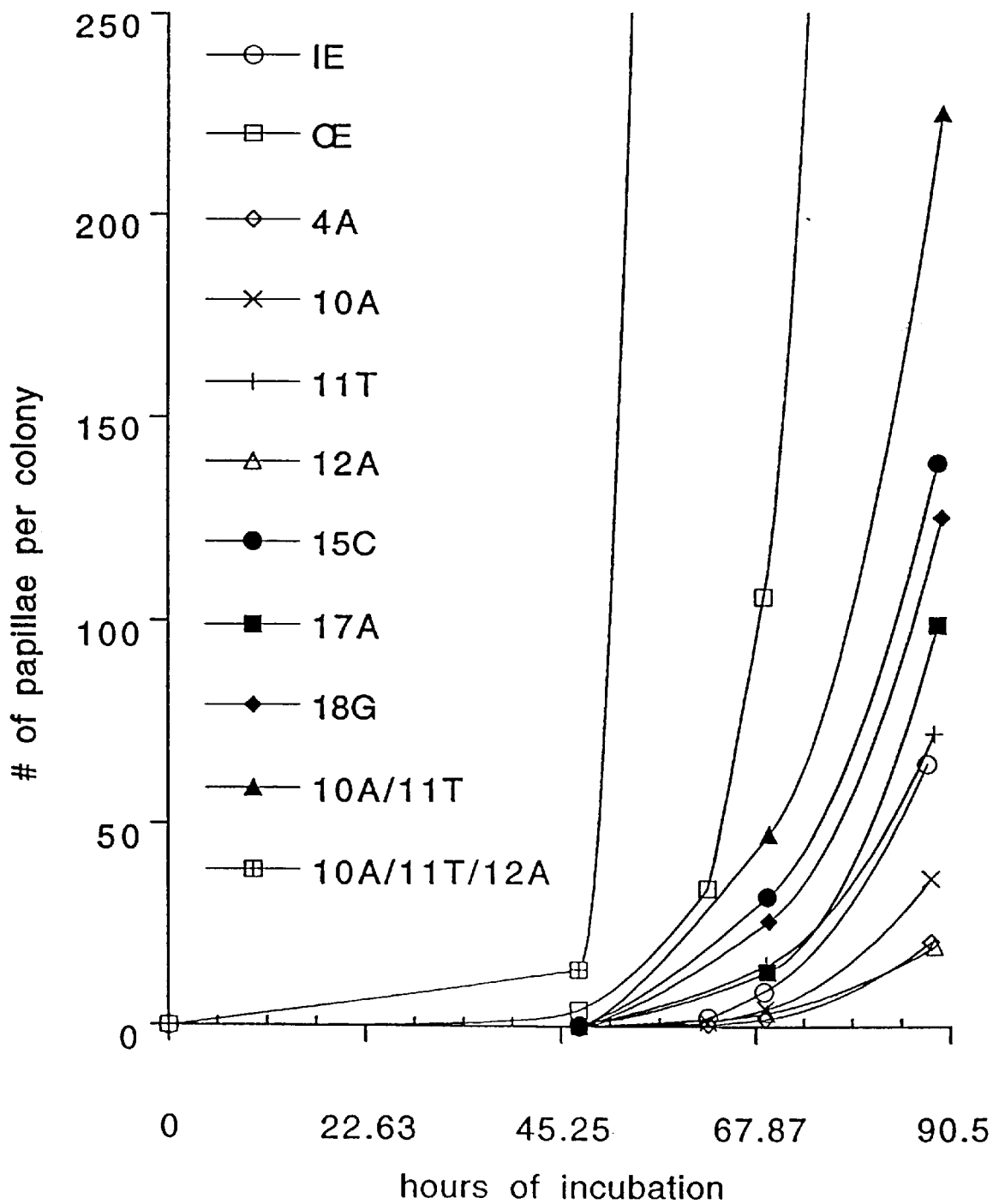
FIG. 6 shows a plot of papillae per colony over time for various mutant OE sequences with a smaller Y-axis than is shown in FIG. 5 tested against EK54/MA56 transposase.
Figure 7:
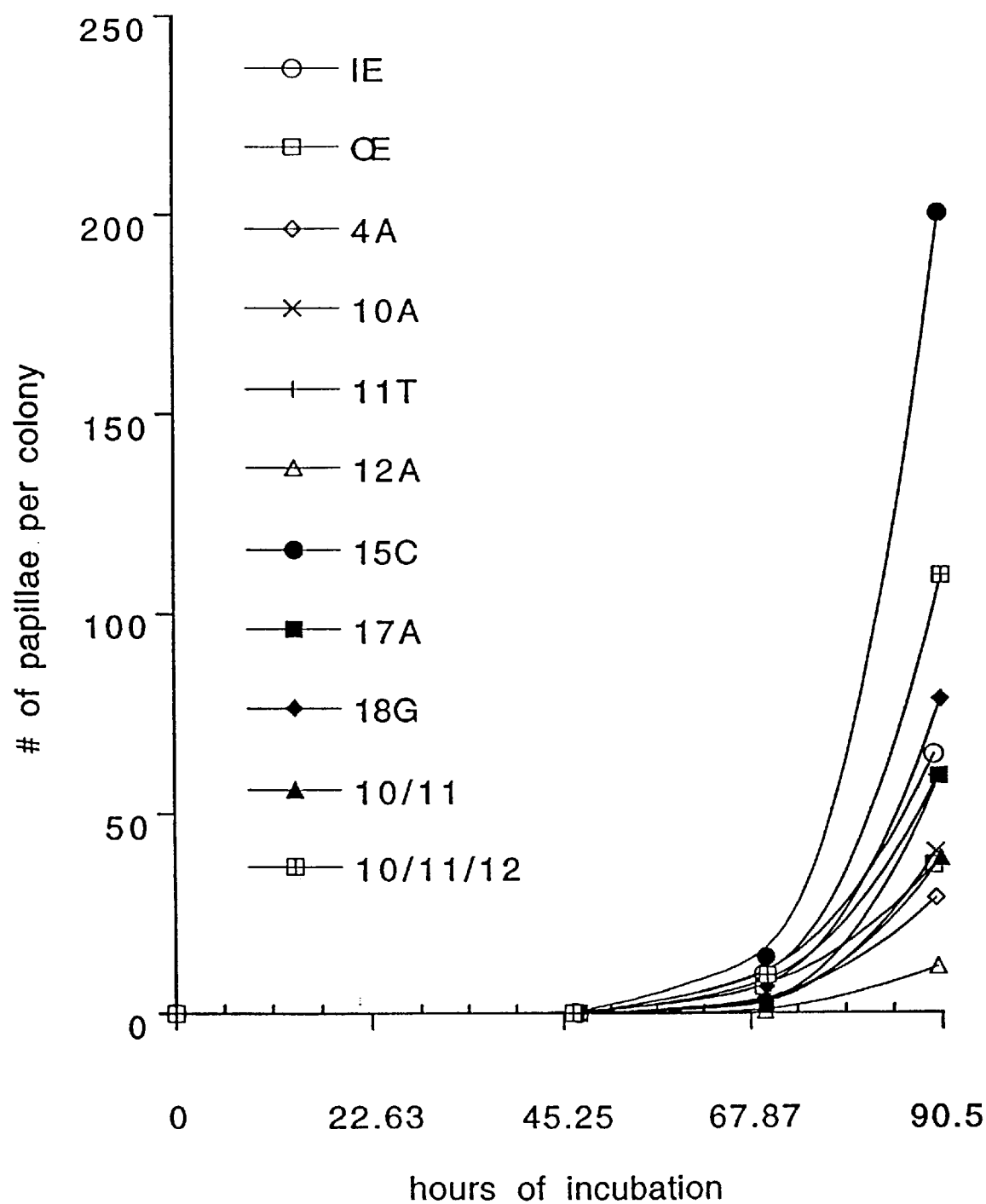
FIG. 7 shows a plot of papillae per colony over time for various mutant OE sequences tested against MA56 Tn5 transposase.

The number of observed papillae increased over time, as is shown in FIGS. 5–7 which roughly quantitate the papillation observed in cells transformed separately with 9 clones containing either distinct synthetic termini cassettes or wild type OE or IE termini. In these 3 figures, each mutant is identified by its differences from the wild type IE sequence. Note that, among the tested mutants, only mutant 10A/11T/12A had a higher transposition papillation level than wild type OE. That mutant, which would be called mutant 4/15/17/18 when OE is the reference sequence) was the only mutant of those shown in FIGS. 5–7 that retained the nucleotides ATA at positions 10, 11, and 12. FIGS. 5 (y-axis: 0–1500 papillae) and 6 (y-axis: 0–250 papillae) show papillation using various mutants plus IE and OE controls and the EK54/MA56 enzyme. FIG. 7 (y-axis: 0–250 papillae), shows papillation when the same mutant sequences were tested against the wild type (more properly, MA56) transposase. The 10A/11T/12A mutant (SEQ ID NO: 9) yielded significantly more papillae (approximately 3000) in a shorter time (68 hours) with ED54/MA56 transposase than was observed even after 90 hours with the WT OE (approximately 1500). A single OE-like nucleotide at position 15 on an IE-like background also increased papillation frequency.

In vivo transposition frequency was also quantitated in a tetracycline-resistance assay using two sequences having high levels of hyperpapillation. These sequences were 5'-CTGTCTCTTATACACATCT-3' (SEQ ID NO: 8), which differs from the wild type OE sequence at positions 4, 17, and 18, counting from the 5' end, and 5'-CTGTCTCTTATACAGATCT-3' (SEQ ID NO: 9), which differs from the wild type OE at positions 4, 15, 17, and 18. These sequences are considered the preferred mutant termini in an assay using a transposase that contains EK54/MA56 or a transposase that contains MA56. Each sequence was separately engineered into pRZTL1 in place of the plasmid's two wild type OE sequences. A PCR-amplified fragment containing the desired ends flanking the kanamycin resistance gene was readily cloned into the large HindIII fragment of pRZTL1. The resulting plasmids are identical to pRZTL1 except at the indicated termini. For comparison, pRZTL1 and a derivative of pRZTL1 containing two wild type IE sequences were also tested. In the assay, JCM101/pOXgen cells were co-transformed with a test plasmid (pRZTL1 or derivative) and a high copy number $amp^r$ plasmid that encoded either the EK54/MA56 transposase or wild type (MA56) transposase. The host cells become tetracycline resistant only when a transposition event brings the $Tet^r$ gene into downstream proximity with a suitable transcriptional promoter elsewhere on a plasmid or on the chromosome. The total number of cells that received the test plasmids was determined by counting chloramphenicol resistant, ampicillin resistant colonies. Transposition frequency was calculated by taking the ratio of $tet^r/cam^r amp^r$ colonies. Approximately 40 to 60 fold increase over wild type OE in in vivo transposition was observed when using either of the mutant termini and EK54/MA56 transposase. Of the two preferred mutant termini, the one containing mutations at three positions relative to the wild type OE sequence yielded a higher increase.

Figure 8:
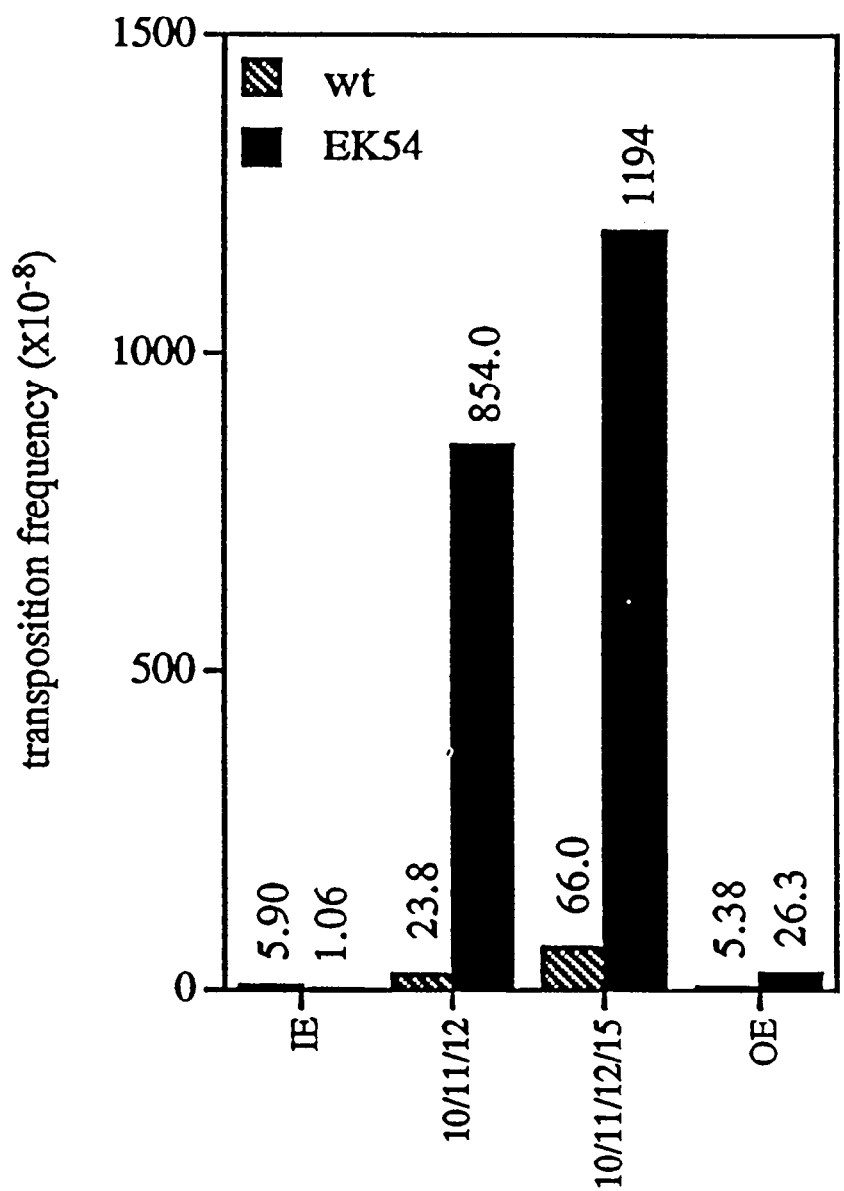
FIG. 8 shows in vivo transposition using two preferred mutants, tested against MA56 and EK54/MA56 transposase.

As is shown in FIG. 8, which plots the tested plasmid against the transposition frequency ($\times 10^{-8}$), little transposition was seen when the test plasmid included two IE termini. Somewhat higher transposition was observed when the test plasmid included two OE termini, particularly when the EK54/MA56 transposase was employed. In striking contrast, the combination of the EK54/MA56 transposase with either of the preferred selected ends (containing OE-like bases only at positions 10, 11, and 12, or positions 10, 11, 12, and 15) yielded a great increase in in vivo transposition over wild type OE termini.

The preferred hyperactive mutant terminus having the most preferred synthetic terminus sequence 5'-CTGTCTCTTATACACATCT-3' (SEQ ID NO: 8) was provided in place of both WT OE termini in pRZTL1 (FIG. 4) and was tested in the in vitro transposition assay of the present invention using the triple mutant transposase described herein. This mutant terminus was chosen for further in vitro analysis because its transposition frequency was higher than for the second preferred synthetic terminus and because it has no dam methylation sites, so dam methylation no longer affects transposition frequency. In contrast the 4/15/17/18 mutant does have a dam methylation site.

In a preliminary experiment, CHAPS was eliminated from the reaction, but the pre-incubation step was used. The reaction was pre-incubated for 1 hour at 20° C., then diluted two times, and then incubated for 3 hours at 37° C. About 0.5 µg of DNA and 0.4 µg of transposase was used. The transposition products were observed on a gel. With the mutant termini, very little of the initial DNA was observed. Numerous bands representing primary and secondary transposition reaction products were observed. The reaction mixtures were transformed into DH5α cells and were plated on chloramphenicol-, tetracycline-, or kanamycin-containing plates.

Six hundred forty chloramphenicol-resistant colonies were observed. Although these could represent unreacted plasmid, all such colonies tested (n=12) were sensitive to kanamycin, which indicates a loss of donor backbone DNA. All twelve colonies also included plasmids of varied size; 9 of the 12 were characterized as deletion-inversions, the remaining 3 were simple deletions. Seventy nine tetracycline-resistant colonies were observed, which indicated an activation of the $tet^r$ gene by transposition.

Eleven kanamycin resistant colonies were observed. This indicated a low percentage of remaining plasmids carrying the donor backbone DNA.

In a second, similar test, about 1 µg of plasmid DNA and 0.2 µg transposase were used. In this test, the reaction was incubated without CHAPS at 37° C. for 3 hours without preincubation or dilution. Some initial DNA was observed in the gel after the 3 hour reaction. After overnight incubation, only transposition products were observed.

The 3 hour reaction products were transformed into DH5α cells and plated as described. About 50% of the chloramphenicol resistant colonies were sensitive to kanamycin and were presumably transposition products.

The invention is not intended to be limited to the foregoing examples, but to encompass all such modifications and variations as come within the scope of the appended claims. It is envisioned that, in addition to the uses specifically noted herein, other applications will be apparent to the skilled molecular biologist. In particular, methods for introducing desired mutations into prokaryotic or eukaryotic DNA are very desirable. For example, at present it is difficult to knock out a functional eukaryotic gene by homologous recombination with an inactive version of the gene that resides on a plasmid. The difficulty arises from the need to flank the gene on the plasmid with extensive upstream and downstream sequences. Using this system, however, an inactivating transposable element containing a selectable marker gene (e.g., neo) can be introduced in vitro into a plasmid that contains the gene that one desires to inactivate. After transposition, the products can be introduced into suitable host cells. Using standard selection means, one can recover only cell colonies that contain a plasmid having the transposable element. Such plasmids can be screened, for example by restriction analysis, to recover those that contain a disrupted gene. Such clones can then be introduced directly into eukaryotic cells for homologous recombination and selection using the same marker gene.

Also, one can use the system to readily insert a PCR-amplified DNA fragment into a vector, thus avoiding traditional cloning steps entirely. This can be accomplished by (1) providing suitable a pair of PCR primers containing OE termini adjacent to the sequence-specific parts of the primers, (2) performing standard PCR amplification of a desired nucleic acid fragment, (3) performing the in vitro transposition reaction of the present invention using the double-stranded products of PCR amplification as the donor DNA.

Construction of pRZ7075 for In Vitro Deletions and Inversions

Plasmid pBR322 was digested with EcoRV and AflIII. The ends were filled in with DNA Polymerase, Klenow Fragment. A 2,077 base pair fragment containing the ColE1 origin and the Ampicillin resistance gene was isolated and was religated to form a circular delta pBR322 plasmid (pRZ7073). This plasmid was digested with EcoRI and HindIII and the large vector fragment was isolated and combined with a multicloning site from pUC19 (isolated as an EcoRI/HindIII fragment) in a ligation reaction. The resulting plasmid was designated pRZ7074.

Separately, a cassette containing a Kanamycin resistance gene flanked by the above-noted preferred OE/IE hybrids substituted at positions 10, 11, 12 and 15 relative to IE (SEQ ID NO:8) was prepared by PCR amplifying an appropriate portion of the above-described pRZTL1-derivative plasmid having the substituted OE/IE hybrids. That pRZTL1 derivative is known as pRZTL4. In the amplification, the primers included tails encoding stop codons in all three reading frames and a terminal SphI site. Thus, when the OE/IE hybrids were amplified, the cassette included the Kanamycin gene flanked on either side by the OE/IE hybrids, stop codons in all three reading frames, and terminal SphI sites. The cassette was cleaved with SphI and was cloned into the SphI site of pRZ7074 to create pRZ7075. The complete nucleotide sequence of pRZ7075 is shown as SEQ ID NO: 12.

In Vitro Transposition Using pRZ7075 With Inserts

Plasmid pRZ7075 was modified to contain either a transposase gene under the control of the T7 promoter (cloned into pRZ7075 at the BamHI site of the multi-cloning site) or an 11 KB segment of genomic DNA (cloned in at the EcoRI site). These modified constructs were used in an in vitro reaction as follows:

0.2–1 μg of DNA

4 μl of 5× reaction buffer 0.3 μg of EK54-LP372 transposase protein water to 20 μl After incubation for two hours at 37° C., the reaction was extracted with phenol and the DNA was precipitated. Half of the resuspended reaction was run on a 1% agarose gel with size markers. The other half was transformed into competent DH5α cells. A 1/1000 dilution of the transformed cells were plated onto Ampicillin plates (100 μg/ml). Individual colonies from the Ampicillin plates were replica plated onto plates containing both Ampicillin and Kanamycin (20 μg/ml). 30%–50% of the Ampicillin colonies were found to be Kanamycin-sensitive, an indication of a transposition event. Kanamycin-sensitive, Ampicillin-resistant colonies were selected for further analysis.

Figure 11:
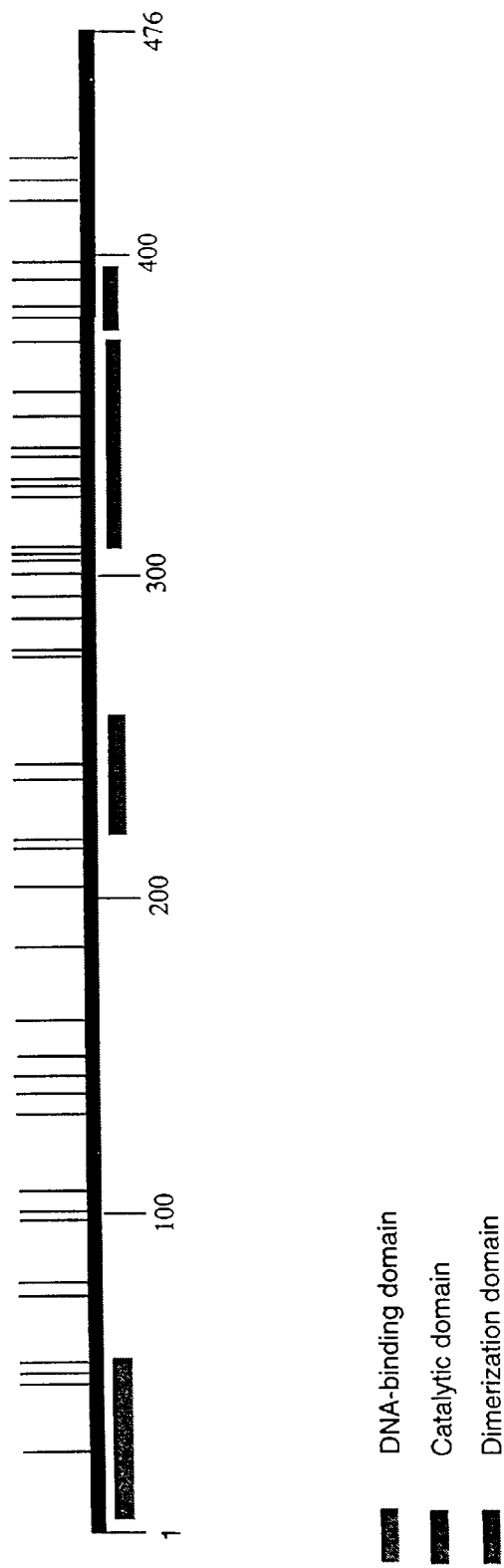
FIG. 11 shows the end points of a battery of deletions that truncated the transposase gene after the in vitro intramolecular transposition method was applied to a derivative of pRZ7075 containing an insert that corresponded to a Tn5 transposase gene.
Figure 12:
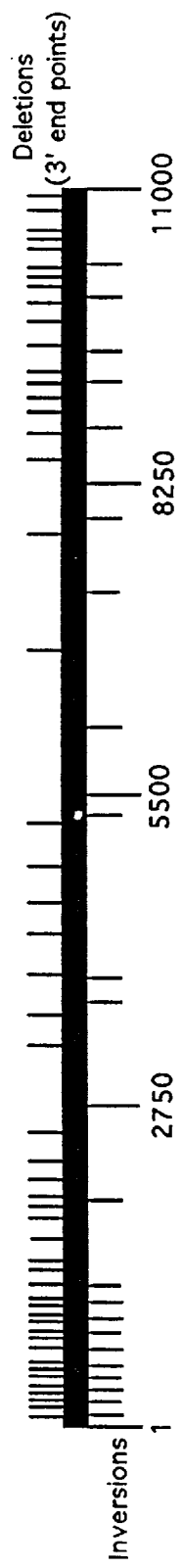
FIG. 12 shows the end points of a battery of deletions that truncated the transposase gene after the in vitro intramolecular transposition method was applied to a derivative of pRZ7075 containing an insert that corresponded to an 11 kbp piece of genomic DNA.

Nucleic acid sequence analysis of numerous transposition products using sequencing primer 5'-CGCAAGAGGCCCGGCAGTAC'3' (SEQ ID NO:13) demonstrated a generally random array of deletion end points in the transposase gene. SEQ ID NO: 13 corresponds to a site near the EcoRV site of pBR322. The end points of deletions that truncated the transposase gene toward the carboxy-terminal end of the coding sequence are shown schematically in FIG. 11. Likewise, when nested deletions were evaluated in the 11 KB genomic DNA insert, as shown in FIG. 12, a generally random distribution of deletion endpoints was observed, although with this larger target a preference for the terminal portions of the insert was noted.

These data demonstrate the powerful use of this intramolecular in vitro transposition construct, method and system to generate nested deletions and inversions for use in subsequent nucleic acid and protein analysis.

The present invention is not intended to be limited to the foregoing embodiments, but to encompass all such modifications and variations as come within the scope of the appended claims.

We claim:

1. A method for in vitro transposition in a genetic construct that comprises a transposable portion and a donor backbone portion, the transposable portion comprising an origin of replication, a nucleotide sequence of interest, and a pair of wild-type or modified Tn5 transposon outside end termini flanking the donor backbone portion, the method comprising the steps of:
    combining, in an in vitro reaction mix, a modified Tn5 transposase enzyme with the genetic construct at a low concentration, to generate reaction products;
    transforming the reaction products into a host cell;
    growing the transformed cells; and
    selecting from among the transformed cells for cells that comprise a DNA molecule that has lost the donor backbone portion and that comprises a transposition in the nucleotide sequence of interest.

2. A method as claimed in claim 1 wherein the transposable portion comprises a first selectable marker that confers resistance to a first selective agent and the donor backbone portion comprises a second selectable marker that confers resistance to a second selective agent, and wherein the selecting step comprises the step of:
    selecting cells that grow in the presence of the first selective agent but which are sensitive to the second selectable marker.

3. A method as claimed in claim 1 wherein the transposable portion comprises a first selectable marker that confers resistance to a first selective agent and the donor backbone portion comprises a marker whose presence is detectable by color, and wherein the selecting step comprises the step of:

selecting cells that grow in the presence of the first selective agent but which lack the color marker.

4. A method as claimed in claim 1 wherein the transposition is selected from a group consisting of a deletion and an inversion.

5. A method as claimed in claim 4 wherein the transposition results in a truncated coding sequence in the nucleotide insert of interest.

6. A method for obtaining a product of in vitro transposition, the method comprising the steps of:

providing a genetic construct that comprises a transposable portion and a donor backbone portion, the transposable portion comprising an origin of replication, a nucleotide sequence of interest, and a pair of wild-type or modified Tn5 transposon outside end termini flanking the donor backbone portion;

combining, in an in vitro reaction mix, a modified Tn5 transposase enzyme with the genetic construct at a low concentration, to generate reaction products;

transforming the reaction products into host cells;

growing the transformed cells;

selecting from among the transformed cells for cells that comprise a DNA molecule that has lost the donor backbone portion and that comprises a transposition in the nucleotide sequence of interest; and isolating DNA from the selected cells.

7. A method as claimed in claim 6, wherein the nucleotide sequence of interest encodes a polypeptide, the method further comprising the steps of:

transcribing the isolated DNA to produce mRNA; and translating the mRNA to produce a polypeptide.

8. A method as claimed in claim 6 wherein the intramolecular transposition is selected from a group consisting of a deletion and an inversion.

9. A method as claimed in claim 8 wherein the transposition results in a truncated coding sequence in the nucleotide insert of interest.

10. A genetic construct comprising:

a transposable portion; a donor backbone portion; and a site for receiving an insert of interest, the transposable portion comprising an origin of replication, a first selectable marker, and a pair of wild-type or modified Tn5 transposon outside end termini flanking the donor backbone portion, the donor backbone portion comprising a selectable gene selected from a group consisting of a second selectable marker and a marker whose presence in a cell is indicated by color.

11. A genetic construct as claimed in claim 10 further comprising a regulated promoter and a translation initiation signal.

12. A genetic construct as claimed in claim 10 further comprising a nucleic acid sequence that encodes an amino acid sequence for tagging an encoded polypeptide.

13. A genetic construct as claimed in claim 10 further comprising a nucleic acid sequence that encodes an amino acid sequence for labeling an encoded polypeptide.

14. A genetic construct as claimed in claim 10 further comprising a nucleic acid sequence that encodes an amino acid sequence for cleaving an encoded polypeptide.

15. A genetic construct as claimed in claim 10 wherein the outside end termini comprise an 18 or 19 base pair sequence that comprises nucleotide A at position 10, nucleotide T at position 11, and nucleotide A at position 12.

16. A genetic construct as claimed in claim 10 having a nucleotide sequence as shown in SEQ ID NO:12.

17. A kit for in vitro intramolecular transposition, the kit comprising:

a genetic construct comprising a transposable portion; a donor backbone portion; and a site for receiving an insert of interest, the transposable portion comprising an origin of replication, a first selectable marker, and a pair of wild-type or modified Tn5 transposon outside end termini flanking the donor backbone portion, the donor backbone portion comprising a selectable gene selected from a group consisting of a second selectable marker and a marker whose presence in a cell is indicated by color; and a modified Tn5 transposase enzyme for use with the transposon outside end termini.

18. A kit as claimed in claim 17 wherein the outside end termini comprise an 18 or 19 base pair sequence that comprises nucleotide A at position 10, nucleotide T at position 11, and nucleotide A at position 12.

19. A kit as claimed in claim 17 wherein the genetic construct has a nucleotide sequence as shown in SEQ ID NO:12.

20. A kit as claimed in claim 17 wherein the transposase enzyme is mutant Tn5 transposase that comprises mutations EK54 and LP372.

* * * * *